(12) United States Patent
Takemura et al.

(10) Patent No.: US 8,450,352 B2
(45) Date of Patent: May 28, 2013

(54) THIAZOLE COMPOUNDS AND THEIR USE FOR INHIBITING PHOSPHODIESTERASE 4, TNF-α, AND IL-4

(75) Inventors: Isao Takemura, Naruto (JP); Kenji Watanabe, Naruto (JP); Kunio Oshima, Tokushima (JP); Nobuaki Ito, Tokushima (JP); Junpei Haruta, Ako (JP); Hidetaka Hiyama, Ako (JP); Masatoshi Chihiro, Naruto (JP); Hideki Kawasome, Naruto (JP); Yoko Sakamoto, Tokushima (JP); Hironobu Ishiyama, Tokushima (JP); Takumi Sumida, Tokushima (JP); Kazuhiko Fujita, Aioi (JP); Hideki Kitagaki, Ako (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 319 days.

(21) Appl. No.: 12/638,143

(22) Filed: Dec. 15, 2009

(65) Prior Publication Data

US 2010/0094002 A1    Apr. 15, 2010

Related U.S. Application Data

(62) Division of application No. 11/587,862, filed as application No. PCT/JP2005/008873 on May 16, 2005, now Pat. No. 7,655,680.

(30) Foreign Application Priority Data

May 17, 2004    (JP) .................. 2004-146834

(51) Int. Cl.
*A61K 31/425*    (2006.01)
(52) U.S. Cl.
USPC .......................... 514/365; 548/202
(58) Field of Classification Search
USPC .......................... 514/365; 548/202
See application file for complete search history.

(56) References Cited

U.S. PATENT DOCUMENTS

| 4,012,495 | A |   | 3/1977 | Schmiechen et al. |
| 4,193,926 | A |   | 3/1980 | Schmiechen et al. |
| 4,826,990 | A |   | 5/1989 | Musser |
| 5,643,932 | A |   | 7/1997 | Chihiro |
| 5,814,651 | A |   | 9/1998 | Duplanter |
| 6,080,764 | A | * | 6/2000 | Chihiro et al. ............ 514/342 |

FOREIGN PATENT DOCUMENTS

| EP | 1 396 487 A1 | 3/2004 |
| EP | 1400515 A1 | 3/2004 |
| JP | 1-143856 A | 6/1989 |
| JP | 5-51318 A | 3/1993 |
| JP | 8-501318 | 2/1996 |
| WO | WO 94/12461 A1 | 6/1994 |
| WO | WO 98/08830 A1 | 3/1998 |
| WO | WO 03/002540 A1 | 1/2003 |
| WO | WO 2004/014903 A1 | 2/2004 |

OTHER PUBLICATIONS

Jordan, V. C. Nature Reviews: Drug Discovery, 2, 2003, 205.*
Hackam, et al. JAMA, 296(14), 2006, 1731-1732.*
Teixeira, M.M. et al., "Phosphodiesterase (PDE) 4 inhibitors: anti-inflammatory drugs of the future?" *Trends Pharmacol. Sci* 18:164-70 (1997).
Souness, J.E. et al., "Immunosuppressive and anti-inflammatory effects of cyclic AMP phosphodiesterase (PDE) type 4 inhibitors," *Immunopharmacology* 47:127-62 (2000).
Essayan, D.M. "Cyclic nucleotide phosphodiesterases," *J. Allergy. Clin. Immunol.* 108:671-80 (2001).
Maurice, D.H. et al., Cyclic nucleotide phosphodiesterase activity, expression, and targeting in cells of cardiovascular system, *Mol. Pharmacol.* 64:533-46 (2003).
Torphy, T.J. "Phosphodiesterase isozymes: Molecular targets for novel antiasthma agents," *Am. J. Respir. Crit. Care. Med.* 157:351-70 (1998).
Giembycz, M.A. "Development status of second generation PDE 4 inhibitors for asthma and COPD: the story so far," *Monaldi. Arch. Chest. Dis.* 57:48-64 (2002).
Krause, W. et al., "Anti-inflammatory activity of rolipram in a rat ear edema model," *Arzneimittelforschung* 44:163-65 (1994).
Revel, L. et al., "CR 2039, a new bis-(1H-tetrazol-5-yl)phenylbenzamide derivative with potential for the topical treatment of asthma," *Eur. J. Pharmacol.* 229:45-53 (1992).
Newsholme, S.J. et al., "CAMP-specific phosphodiesterase inhibitor, rolipram, reduces eosinophil infiltration evoked by leukotrienes or by histamine in guinea pig conjunctiva," *Inflammation* 17: 25-31 (1993).
Sommer, N. et al., "The antidepressant rolipram suppresses cytokine production and prevents autoimmune encephalomyelitis," *Nat. Med.* 1:244-48 (1995).
Sommer, N. et al., "Therapeutical potential of phosphodiesterase type 4-inhibition in chronic autoimmune demyelinating disease," *J. Neuroimmunol.* 79:54-61 (1997).
Sekut, L. et al., "Anti-inflammatory activity of phosphodiesterase (PDE)-IV inhibitors in acute and chronic models of inflammation," *Clin. Exp. Immunol.* 100:126-32 (1995).
Nyman, U. et al., "Amelioration of collagen II-induced arthritis in rats by the type IV phosphodiesterase inhibitor rolipram," *Clin. Exp. Immunol.* 108:415-19 (1997).

(Continued)

Primary Examiner — Douglas M Willis
(74) Attorney, Agent, or Firm — Finnegan, Henderson, Farabow, Garrett & Dunner, L.L.P.

(57) ABSTRACT

Thiazole compounds for inhibiting the activity of phosphodiesterase 4, the production of tumor necrosis factor alpha, and the production of interleukin 4. The compounds of the invention are represented by general formula (1):

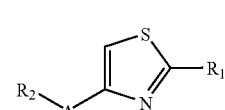

(1)

wherein A is any one of the following groups (i)-(iii): (i) —CH(OH)—B— wherein B is a $C_{1-6}$ alkylene group; (ii) —COCH(COOR3)-Bb- wherein R3 is a $C_{1-6}$ alkyl group and Bb is a $C_{1-6}$ alkylene group; and (iii) -Bc- wherein Bc is a $C_{2-6}$ alkylene group, and include optical isomers and salts of the compounds.

7 Claims, No Drawings

OTHER PUBLICATIONS

Ross, S.E. et al., "Suppression of TNF-α expression, inhibition of Th1 activity and amelioration of collagen-induced arthritis by rolipram," *J. Immunol.* 159:6253-259 (1997).

Beavo, J.A. "Cyclic Nucleotide Phosphodiesterase: Functional Implications of Multiple Isoforms," *Physiol. Rev.* 75:725-48 (1995).

Renauld, J-C "New insights into the role of cytokines in asthma," *J. Clin. Pathol.* 54:577-89 (2001).

Reimold, A.M. "TNF-α as therapeutic target: New drugs, more applications," *Curr. Drug Targets Inflamm. Allergy* 1 377-92 (2002).

Jarnicki, A.G. et al., "T helper type-2 cytokine responses: potential therapeutic targets," *Curr. Opin. Pharmacol.* 3:449-55 (2003).

Vizcarra, C. "New Perspectives and Emerging Therapies for Immune-mediated Inflammatory Disorders," *J. Infus. Nurs.* 26:319-25 (2003).

Malamas, M.S. et al., "Azole Phenoxy Hydroxyureas as Selective and Orally Active Inhibitors of 5-Lipoxygenase," *J. Med. Chem.*, 39:237-45 (1996).

Jordan, V.C., "Tamoxifen: a most unlikely pioneering medicine," *Nat. Rev. Drug Discov.* 2:205-13 (2003).

Zaragoza, D.F. Side Reactions in Organic Synthesis: A Guide to Successful Synthesis Design, Weinheim: *Wiley-VCH Verlag GmbH & Co. KGaA*, Preface (2005).

International Search Report, mailed Jun. 14, 2005, in International Patent Application No. PCT/JP2005/008873.

Hinegardner, W.S. et al., "The Synthesis of Thiazole Amines Possessing Pharmacological Interest. VI," Journal of the American Chemical Society, vol. 52, pp. 4141-4144 (1930).

Examination Report for Indian Patent Application No. 6587/DELNP/2006 dated Jan. 24, 2012.

* cited by examiner

THIAZOLE COMPOUNDS AND THEIR USE FOR INHIBITING PHOSPHODIESTERASE 4, TNF-α, AND IL-4

CROSS-REFERENCE TO RELATED APPLICATIONS

This application is a division of U.S. patent application Ser. No. 11/587,862, filed Jul. 5, 2007, now U.S. Pat. No. 7,655,680, which is the U.S. national stage application of PCT/JP2005/008873, filed May 16, 2005, which claims the benefit of Japanese patent application JP-2004-146834, filed May 17, 2004, all of which are incorporated herein by reference.

FIELD OF THE INVENTION

The present invention relates to a novel thiazole compound. The present invention further relates to a pharmaceutical composition comprising the thiazole compound.

BACKGROUND OF THE INVENTION

Researchers have recently discovered that cyclic adenosine 3',5'-monophosphate (cAMP), which acts as an intracellular second messenger, controls the activity of inflammatory cells, such as lymphocytes, neutrophils, eosinophils, mast cells, etc. It is known that cAMP is degraded to 5'-AMP, which does not act as a messenger, by the action of phosphodiesterase (PDE), and that PDE adjusts the intracellular cAMP concentration. Since PDE has such a close relationship with the intracellular cAMP concentration, controlling PDE activity is believed to be effective against diseases for which therapeutic effects are expected to be exhibited by controlling the increase or decrease of the cAMP concentration (see *Trends Pharmacol. Sci.* 18: 164-170, 1997 and *Immunopharmacology* 47: 127-162, 2000).

Eleven types of PDE isozymes (PDEs 1 to 11) are known, and their in vivo distributions are known to vary among different tissues (see *J. Allergy. Clin. Immunol.* 108: 671-680, 2001 and *Mol. Pharmacol.* 64: 533-546, 2003). Reportedly, inhibitors specific to PDE4 suppress the functions of inflammatory cells, and are believed to be useful against conjunctivitis, asthma and like inflammatory allergic diseases, and multiple sclerosis, articular rheumatism and like autoimmune diseases (see *Am. J. Respir. Crit. Care. Med.* 157:351-370, 1998; *Monaldi. Arch. Chest. Dis.* 57: 48-64, 2002; *Arzneimittelforschung* 44: 163-165, 1994; *Eur. J. Pharmacol.* 229: 45-53, 1992; *Inflammation* 17: 25-31, 1993; *Nat. Med.* 1: 244-248, 1995; *J. Neuroimmunol.* 79: 54-61, 1997; *Clin. Exp. Immunol.* 100: 126-132, 1995; *Clin. Exp. Immunol.* 108: 415-419, 1997; and *J. Immunol.* 159: 6253-6259, 1997).

Theophylline has been hitherto used as a PDE inhibitor for treating asthma. However, theophylline is known to nonspecifically inhibit various PDE isozymes, and thus inhibits not only PDE4 but also PDE3 and other isozymes. The inhibition of PDE3 is suspected of causing cardiotonic action and/or central action and producing positive inotropic and chronotropic effects in the heart (see *Physiol. Rev.* 76: 725-748, 1995). Therefore, the use of theophylline as a PDE inhibitor poses the problem of side effects.

Some compounds with specific inhibitory activity against PDE 4 have been reported (see Japanese Unexamined Patent Publication No. 1975-157360 and Japanese Unexamined Patent Publication No. 2003-64057). However, such PDE4 inhibitors have problems in that they bind to the high affinity rolipram binding site (HARBS) in the central nervous system and the alimentary canal and produce side effects, such as emesis induction and nausea, or have drawbacks in that they show insufficient PDE4 inhibitory activity. Thus, heretofore known PDE4 inhibitors have not been used clinically as therapeutic agents.

In view of this prior art, the development of a compound that effectively exhibits, without side effects, specific inhibitory activity against PDE4 is desired.

SUMMARY OF THE INVENTION

An object of the present invention is to solve the above problems of the prior art. Specifically, an object of the present invention is to provide a novel thiazole compound that has specific inhibitory activity against PDE4, and a pharmaceutical composition comprising the compound. Another object of the present invention is to provide a PDE4 inhibitor that exhibits specific inhibitory activity against PDE4. A further object of the present invention is to provide a preventive or therapeutic agent for atopic dermatitis, and a method for treating atopic dermatitis.

The present inventors searched for a new compound that has PDE4 inhibitory activity, and found that a thiazole compound with a new structure has strong PDE4 inhibitory activity that is highly specific and dissociated from HARBS binding activity. The inventors further found that the thiazole compound exhibits preventive or therapeutic effects against atopic dermatitis because of its PDE4 inhibitory activity.

The inventors further found that the thiazole compound also exhibits TNF-α production inhibitory activity and IL-4 production inhibitory activity. In chronic inflammatory diseases, such as autoimmune diseases and allergic diseases, cytokines produced by immunocompetent cells are known as important inflammatogenic mediators. Among such cytokines, tumor necrosis factor (TNF)-α and interleukin (IL)-4 are believed to play important roles (see *J. Clin. Pathol.* 54: 577-589, 2001; *Curr. Drug Targets Inflamm. Allergy* 1:377-392, 2002; *Curr. Opin. Pharmacol.* 3: 449-455, 2003; and *J. Infus. Nurs.* 26: 319-325, 2003). Accordingly, compounds with TNF-α production inhibitory activity or IL-4 production inhibitory activity are clinically useful.

The present invention was accomplished by conducting further research based on the above findings.

The present invention provides the following thiazole compounds.

1. A compound represented by Formula (1), an optical isomer thereof, or a salt thereof:

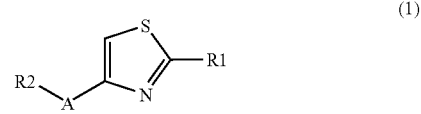

(1)

wherein R1 is a di-$C_{1-6}$ alkoxyphenyl group;
R2 is any one of the following groups (a) to (t):
(a) a phenyl group in which the phenyl ring may be substituted with one or more members selected from the group consisting of (a-1) hydroxy groups, (a-2) halogen atoms, (a-3) unsubstituted or halogen-substituted $C_{1-6}$ alkyl groups, (a-4) unsubstituted or halogen-substituted $C_{1-6}$ alkoxy groups, (a-5) $C_{1-6}$ alkoxy-$C_{1-6}$ alkoxy groups, (a-6) amino-$C_{1-6}$ alkoxy groups which may be substituted with a $C_{1-6}$ alkyl group or groups, (a-7) methylenedioxy groups, (a-8) carboxyl groups, (a-9) phenoxy groups, (a-10) $C_{1-6}$ alkoxycarbonyl groups, (a-11) $C_{1-6}$ alkanoyloxy groups, (a-12) $C_{1-6}$ alkanoyl groups, (a-13) cyano groups, (a-14) nitro groups, (a-15) $C_{1-6}$ alkylcarbamoyl groups, (a-16) aminosulfonyl groups, (a-17) amino groups which may be substituted with a $C_{1-6}$ alkyl group or groups, (a-18) $C_{1-6}$ alkanoylamino groups, (a-19) $C_{1-6}$ alkylthio groups, (a-20) phenyl groups, (a-21) pyrazolyl groups, (a-22) imidazolyl groups, (a-23) triazolyl groups, (a-24) morpholino groups, (a-25) pyrrolidinyl groups, (a-26) piperazinylcarbonyl groups which may be substituted with a $C_{1-6}$ alkyl group or groups, and (a-27) phenyl-$C_{1-6}$ alkoxy groups;

(b) a naphthyl group;

(c) a pyridyl group in which the pyridine ring may be substituted with one or more members selected from the group consisting of (c-1) hydroxy groups, (c-2) $C_{1-6}$ alkyl groups, (c-3) $C_{1-6}$ alkoxy groups, (c-4) phenyl-$C_{1-6}$ alkoxy groups, and (c-5) $C_{1-6}$ alkoxycarbonyl groups;

(d) a furyl group in which the furan ring may be substituted with a $C_{1-6}$ alkyl group or groups;

(e) a thienyl group in which the thiophene ring may be substituted with one or more members selected from the group consisting of (e-1) halogen atoms, (e-2) $C_{1-6}$ alkyl groups, and (e-3) $C_{1-6}$ alkoxy groups;

(f) an isoxazolyl group in which the isoxazolyl ring may be substituted with a $C_{1-6}$ alkyl group or groups;

(g) a thiazolyl group in which the thiazole ring may be substituted with one or more members selected from the group consisting of (g-1) $C_{1-6}$ alkyl groups, and (g-2) phenyl groups which may be substituted with a $C_{1-6}$ alkoxy group or groups;

(h) a pyrrolyl group in which the pyrrole ring may be substituted with a $C_{1-6}$ alkyl group or groups;

(i) an imidazolyl group in which the imidazole ring may be substituted with a $C_{1-6}$ alkyl group or groups;

(j) a tetrazolyl group;

(k) a pyrazinyl group;

(l) a thienothienyl group;

(m) a benzothienyl group;

(n) an indolyl group in which the indole ring may be substituted with a $C_{1-6}$ alkoxy group or groups;

(o) a benzimidazolyl group in which the benzimidazole ring may be substituted with a $C_{1-6}$ alkyl group or groups;

(p) an indazolyl group;

(q) a quinolyl group;

(r) a 1,2,3,4-tetrahydroquinolyl group in which the 1,2,3,4-tetrahydroquinoline ring may be substituted with an oxo group or groups;

(s) a quinoxalinyl group; and (t) a 1,3-benzodioxolyl group; and

A is any one of the following groups (i) to (v):

(i) —CO—B— wherein B is a $C_{1-6}$ alkylene group;

(ii) —CO—Ba— wherein Ba is a $C_{2-6}$ alkenylene group;

(iii) —CH(OH)—B— wherein B is as defined above;

(iv) —COCH(COOR3)-Bb- wherein R3 is a $C_{1-6}$ alkyl group and Bb is a $C_{1-6}$ alkylene group; and (v) -Bc- wherein Bc is a $C_{2-6}$ alkylene group.

2. A compound according to Item 1, wherein, in Formula (1), R1 is a 3,4-di-$C_{1-6}$ alkoxyphenyl group; an optical isomer thereof; or a salt thereof.

3. A compound according to Item 1, wherein, in Formula (1), R1 is a 3,4-dimethoxyphenyl group or a 3,4-diethoxyphenyl group; an optical isomer thereof; or a salt thereof.

4. A compound according to any one of Items 1 to 3, wherein, in Formula (1), R2 is (a) a phenyl group in which the phenyl ring may be substituted with one or more members selected from the group consisting of (a-1) hydroxy groups, (a-2) halogen atoms, (a-3) unsubstituted or halogen-substituted $C_{1-6}$ alkyl groups, (a-4) unsubstituted or halogen-substituted $C_{1-6}$ alkoxy groups, (a-5) $C_{1-6}$ alkoxy-$C_{1-6}$ alkoxy groups, (a-6) amino-$C_{1-6}$ alkoxy groups which may be substituted with a $C_{1-6}$ alkyl group or groups, (a-7) methylenedioxy groups, (a-8) carboxyl groups, (a-9) phenoxy groups, (a-10) $C_{1-6}$ alkoxycarbonyl groups, (a-11) $C_{1-6}$ alkanoyloxy groups, (a-12) $C_{1-6}$ alkanoyl groups, (a-13) cyano groups, (a-14) nitro groups, (a-15) $C_{1-6}$ alkylcarbamoyl groups, (a-16) aminosulfonyl groups, (a-17) amino groups which may be substituted with a $C_{1-6}$ alkyl group or groups, (a-18) $C_{1-6}$ alkanoylamino groups, (a-19) $C_{1-6}$ alkylthio groups, (a-20) phenyl groups, (a-21) pyrazolyl groups, (a-22) imidazolyl groups, (a-23) triazolyl groups, (a-24) morpholino groups, (a-25) pyrrolidinyl groups, (a-26) piperazinylcarbonyl groups which may be substituted with a $C_{1-6}$ alkyl group or groups, and (a-27) phenyl-$C_{1-6}$ alkoxy groups;

(c) a pyridyl group in which the pyridine ring may be substituted with one or more members selected from the group consisting of (c-1) hydroxy groups, (c-2) $C_{1-6}$ alkyl groups, (c-3) $C_{1-6}$ alkoxy groups, (c-4) phenyl-$C_{1-6}$ alkoxy groups, and (c-5) $C_{1-6}$ alkoxycarbonyl groups;

(d) a furyl group in which the furan ring may be substituted with a $C_{1-6}$ alkyl group or groups;

(e) a thienyl group in which the thiophene ring may be substituted with one or more members selected from the group consisting of (e-1) halogen atoms, (e-2) $C_{1-6}$ alkyl groups, and (e-3) $C_{1-6}$ alkoxy groups;

(g) a thiazolyl group in which the thiazole ring may be substituted with one or more members selected from the group consisting of (g-1) $C_{1-6}$ alkyl groups, and (g-2) phenyl groups which may be substituted with a $C_{1-6}$ alkoxy group or groups;

(h) a pyrrolyl group in which the pyrrole ring may be substituted with a $C_{1-6}$ alkyl group or groups; or (i) an imidazolyl group in which the imidazole ring may be substituted with a $C_{1-6}$ alkyl group or groups; an optical isomer thereof; or a salt thereof.

5. A compound according to any one of Items 1 to 3, wherein, in Formula (1), R2 is (a) a phenyl group in which the phenyl ring may be substituted with one or more members selected from the group consisting of (a-1) hydroxy groups, (a-2) halogen atoms, (a-3) unsubstituted or halogen-substituted $C_{1-6}$ alkyl groups, (a-4) unsubstituted or halogen-substituted $C_{1-6}$ alkoxy groups, (a-5) $C_{1-6}$ alkoxy-$C_{1-6}$ alkoxy groups, (a-6) amino-$C_{1-6}$ alkoxy groups which may be substituted with a $C_{1-6}$ alkyl group or groups, (a-7) methylenedioxy groups, (a-8) carboxyl groups, (a-9) phenoxy groups, (a-10) $C_{1-6}$ alkoxycarbonyl groups, (a-11) $C_{1-6}$ alkanoyloxy groups, (a-12) $C_{1-6}$ alkanoyl groups, (a-13) cyano groups, (a-14) nitro groups, (a-15) $C_{1-6}$ alkylcarbamoyl groups, (a-16) aminosulfonyl groups, (a-17) amino groups which may be substituted with a $C_{1-6}$ alkyl group or groups, (a-18) $C_{1-6}$ alkanoylamino groups, (a-19) $C_{1-6}$ alkylthio groups, (a-20) phenyl groups, (a-21) pyrazolyl groups, (a-22) imidazolyl groups, (a-23) triazolyl groups, (a-24) morpholino groups, (a-25) pyrrolidinyl groups, (a-26) piperazinylcarbonyl groups which may be substituted with a $C_{1-6}$ alkyl group or groups, and (a-27) phenyl-$C_{1-6}$ alkoxy groups;

(c) a pyridyl group in which the pyridine ring may be substituted with one or more members selected from the group consisting of (c-1) hydroxy groups, (c-2) $C_{1-6}$ alkyl groups, (c-3) $C_{1-6}$ alkoxy groups, (c-4) phenyl-$C_{1-6}$ alkoxy groups, and (c-5) $C_{1-6}$ alkoxycarbonyl groups; or (g) a thiazolyl group in which the thiazole ring may be substituted with one or more members selected from the group consisting of (g-1) $C_{1-6}$ alkyl groups, and (g-2) phenyl groups which may be substituted with a $C_{1-6}$ alkoxy group or groups; an optical isomer thereof; or a salt thereof.

6. A compound according to any one of Items 1 to 5, wherein, in Formula (1), A is (i) —CO—B— wherein B is a methylene group, an ethylene group or a trimethylene group; (ii) —CO—Ba— wherein Ba is a vinylidene group; (iii)

—CH(OH)—B— wherein B is a methylene group or an ethylene group; (iv) —COCH(COOR3)-Bb- wherein R3 is a methyl group, an ethyl group or a tert-butyl group and Bb is a methylene group or an ethylene group; or (v) -Bc- wherein Bc is an ethylene group, a trimethylene group or a tetramethylene group; an optical isomer thereof; or a salt thereof.

7. A compound according to any one of Items 1 to 5, wherein, in Formula (1), A is (i) —CO—B— wherein B is an ethylene group; (iii) —CH(OH)—B— wherein B is an ethylene group; (iv) —COCH(COOR3)-Bb- wherein R3 is a methyl group and Bb is a methylene group; or (v) -Bc- wherein Bc is a trimethylene group; an optical isomer thereof; or a salt thereof.

8. A compound according to Item 1, wherein, in Formula (1), R1 is a 3,4-di-$C_{1-6}$ alkoxyphenyl group;

R2 is (a) a phenyl group in which the phenyl ring may be substituted with one or more members selected from the group consisting of (a-1) hydroxy groups, (a-2) halogen atoms, (a-3) unsubstituted or halogen-substituted $C_{1-6}$ alkyl groups, (a-4) unsubstituted or halogen-substituted $C_{1-6}$ alkoxy groups, (a-5) $C_{1-6}$ alkoxy-$C_{1-6}$ alkoxy groups, (a-6) amino-$C_{1-6}$ alkoxy groups which may be substituted with a $C_{1-6}$ alkyl group or groups, (a-7) methylenedioxy groups, (a-8) carboxyl groups, (a-9) phenoxy groups, (a-10) $C_{1-6}$ alkoxycarbonyl groups, (a-11) $C_{1-6}$ alkanoyloxy groups, (a-12) $C_{1-6}$ alkanoyl groups, (a-13) cyano groups, (a-14) nitro groups, (a-15) $C_{1-6}$ alkylcarbamoyl groups, (a-16) aminosulfonyl groups, (a-17) amino groups which may be substituted with a $C_{1-6}$ alkyl group or groups, (a-18) $C_{1-6}$ alkanoylamino groups, (a-19) $C_{1-6}$ alkylthio groups, (a-20) phenyl groups, (a-21) pyrazolyl groups, (a-22) imidazolyl groups, (a-23) triazolyl groups, (a-24) morpholino groups, (a-25) pyrrolidinyl groups, (a-26) piperazinylcarbonyl groups which may be substituted with a $C_{1-6}$ alkyl group or groups, and (a-27) phenyl-$C_{1-6}$ alkoxy groups;
(c) a pyridyl group in which the pyridine ring may be substituted with one or more members selected from the group consisting of (c-1) hydroxy groups, (c-2) $C_{1-6}$ alkyl groups, (c-3) $C_{1-6}$ alkoxy groups, (c-4) phenyl-$C_{1-6}$ alkoxy groups, and (c-5) $C_{1-6}$ alkoxycarbonyl groups;
(d) a furyl group in which the furan ring may be substituted with a $C_{1-6}$ alkyl group or groups;
(e) a thienyl group in which the thiophene ring may be substituted with one or more members selected from the group consisting of (e-1) halogen atoms, (e-2) $C_{1-6}$ alkyl groups, and (e-3) $C_{1-6}$ alkoxy groups;
(g) a thiazolyl group in which the thiazole ring may be substituted with one or more members selected from the group consisting of (g-1) $C_{1-6}$ alkyl groups, and (g-2) phenyl groups which may be substituted with a $C_{1-6}$ alkoxy group or groups;
(h) a pyrrolyl group in which the pyrrole ring may be substituted with one or more $C_{1-6}$ alkyl groups;
(i) an imidazolyl group in which the imidazole ring may be substituted with a $C_{1-6}$ alkyl group or groups; and
A is (i) —CO—B— wherein B is as defined above; (ii) —CO—Ba wherein Ba is as defined above; (iii) —CH(OH)—B— wherein B is as defined above; (iv) —COCH(COOR3)-Bb- wherein R3 and Bb are as defined above; or (v) -Bc- wherein Bc is as defined above; an optical isomer thereof; or a salt thereof.

9. A compound according to Item 1, wherein, in Formula (1), R1 is a 3,4-di-$C_{1-6}$ alkoxyphenyl group;

R2 is (a) a phenyl group in which the phenyl ring may be substituted with one or more members selected from the group consisting of (a-1) hydroxy groups, (a-2) halogen atoms, (a-3) unsubstituted or halogen-substituted $C_{1-6}$ alkyl groups, (a-4) unsubstituted or halogen-substituted $C_{1-6}$ alkoxy groups, (a-5) $C_{1-6}$ alkoxy-$C_{1-6}$ alkoxy groups, (a-6) amino-$C_{1-6}$ alkoxy groups which may be substituted with a $C_{1-6}$ alkyl group or groups, (a-7) methylenedioxy groups, (a-8) carboxyl groups, (a-9) phenoxy groups, (a-10) $C_{1-6}$ alkoxycarbonyl groups, (a-11) $C_{1-6}$ alkanoyloxy groups, (a-12) $C_{1-6}$ alkanoyl groups, (a-13) cyano groups, (a-14) nitro groups, (a-15) $C_{1-6}$ alkylcarbamoyl groups, (a-16) aminosulfonyl groups, (a-17) amino groups which may be substituted with a $C_{1-6}$ alkyl group or groups, (a-18) $C_{1-6}$ alkanoylamino groups, (a-19) $C_{1-6}$ alkylthio groups, (a-20) phenyl groups, (a-21) pyrazolyl groups, (a-22) imidazolyl groups, (a-23) triazolyl groups, (a-24) morpholino groups, (a-25) pyrrolidinyl groups, (a-26) piperazinylcarbonyl groups which may be substituted with a $C_{1-6}$ alkyl group or groups, and (a-27) phenyl-$C_{1-6}$ alkoxy groups;
(c) a pyridyl group in which the pyridine ring may be substituted with one or more members selected from the group consisting of (c-1) hydroxy groups, (c-2) $C_{1-6}$ alkyl groups, (c-3) $C_{1-6}$ alkoxy groups, (c-4) phenyl-$C_{1-6}$ alkoxy groups, and (c-5) $C_{1-6}$ alkoxycarbonyl groups;
(d) a furyl group in which the furan ring may be substituted with a $C_{1-6}$ alkyl group or groups;
(e) a thienyl group in which the thiophene ring may be substituted with one or more members selected from the group consisting of (e-1) halogen atoms, (e-2) $C_{1-6}$ alkyl groups, and (e-3) $C_{1-6}$ alkoxy groups;
(g) a thiazolyl group in which the thiazole ring may be substituted with one or more members selected from the group consisting of (g-1) $C_{1-6}$ alkyl groups, and (g-2) phenyl groups which may be substituted with a $C_{1-6}$ alkoxy group or groups;
(h) a pyrrolyl group in which the pyrrole ring may be substituted with a $C_{1-6}$ alkyl group or groups; or
(i) an imidazolyl group in which the imidazole ring may be substituted with a $C_{1-6}$ alkyl group or groups; and
A is (i) —CO—B— wherein B is a methylene group, an ethylene group or a trimethylene group; (ii) —CO—Ba— wherein Ba is a vinylidene group; (iii) —CH(OH)—B— wherein B is a methylene group or an ethylene group; (iv) —COCH(COOR3)-Bb- wherein R3 is a methyl group, an ethyl group or a tert-butyl group and Bb is a methylene group or an ethylene group; or (v) -Bc- wherein Bc is an ethylene group, a trimethylene group or a tetramethylene group; an optical isomer thereof; or a salt thereof.

10. A compound according to Item 1, wherein, in Formula (1), R1 is a 3,4-di-$C_{1-6}$ alkoxyphenyl group;

R2 is (a) a phenyl group in which the phenyl ring may be substituted with one or more members selected from the group consisting of (a-1) hydroxy groups, (a-2) halogen atoms, (a-3) unsubstituted or halogen-substituted $C_{1-6}$ alkyl groups, (a-4) unsubstituted or halogen-substituted $C_1$ alkoxy groups, (a-5) $C_{1-6}$ alkoxy-$C_{1-6}$ alkoxy groups, (a-6) amino-$C_{1-6}$ alkoxy groups which may be substituted with a $C_{1-6}$ alkyl group or groups, (a-7) methylenedioxy groups, (a-8) carboxyl groups, (a-9) phenoxy groups, (a-10) $C_{1-6}$ alkoxycarbonyl groups, (a-11) $C_{1-6}$ alkanoyloxy groups, (a-12) $C_{1-6}$ alkanoyl groups, (a-13) cyano groups, (a-14) nitro groups, (a-15) $C_{1-6}$ alkylcarbamoyl groups, (a-16) aminosulfonyl groups, (a-17) amino groups which may be substituted with a $C_{1-6}$ alkyl group or groups, (a-18) $C_{1-6}$ alkanoylamino groups, (a-19) $C_{1-6}$ alkylthio groups, (a-20) phenyl groups, (a-21) pyrazolyl groups, (a-22) imidazolyl groups, (a-23) triazolyl groups, (a-24) morpholino groups, (a-25) pyrrolidinyl groups, (a-26) piperazinylcarbonyl groups which may be substituted with a $C_{1-6}$ alkyl group or groups, and (a-27) phenyl-$C_{1-6}$ alkoxy groups;
(c) a pyridyl group in which the pyridine ring may be substituted with one or more members selected from the group consisting of (c-1) hydroxy groups, (c-2) $C_{1-6}$ alkyl groups, (c-3) $C_{1-6}$ alkoxy groups, (c-4) phenyl-$C_{1-6}$ alkoxy groups, and (c-5) $C_{1-6}$ alkoxycarbonyl groups; or (g) a thiazolyl group in which the thiazole ring may be substituted with one or more members selected from the group consisting of (g-1) $C_{1-6}$ alkyl groups, and (g-2) phenyl groups which may be substituted with a $C_1$ alkoxy group or groups; and A is (i) —CO—B— wherein B is an ethylene group; (iii) —CH(OH)—B— wherein B is an ethylene group; (iv) —COCH(COOR3)-Bb- wherein R3 is a methyl group and Bb is a methylene group; or (v) -Bc- wherein Bc is a trimethylene group.

The present invention further provides the following uses of the above thiazole compounds.

11. A pharmaceutical composition comprising a compound according to any one of Items 1 to 10, an optical isomer thereof, or a salt thereof.

12. A phosphodiesterase 4 inhibitor comprising as an active ingredient a compound according to any one of Items 1 to 10, an optical isomer thereof, or a salt thereof.

13. A TNF-α production inhibitor comprising as an active ingredient a compound according to any one of Items 1 to 10, an optical isomer thereof, or a salt thereof.

14. An IL-4 production inhibitor comprising as an active ingredient a compound according to any one of Items 1 to 10, an optical isomer thereof, or a salt thereof.

15. A preventive or therapeutic agent for atopic dermatitis, comprising as an active ingredient a compound according to any one of Items 1 to 10, an optical isomer thereof, or a salt thereof.

16. A method for treating atopic dermatitis, comprising the step of administering to a human or non-human mammal an effective amount of a compound according to any one of Items 1 to 10, an optical isomer thereof, or a salt thereof.

17. Use of a compound according to any one of Items 1 to 10, an optical isomer thereof, or a salt thereof, for producing a preventive or therapeutic agent for atopic dermatitis.

18. Use of a compound according to any one of Items 1 to 10, an optical isomer thereof, or a salt thereof, for producing a phosphodiesterase 4 inhibitor.

19. Use of a compound according to any one of Items 1 to 10, an optical isomer thereof, or a salt thereof, for producing a TNF-α production inhibitor.

20. Use of a compound according to any one of Items 1 to 10, an optical isomer thereof, or a salt thereof, for producing an IL-4 production inhibitor.

DETAILED DESCRIPTION OF THE INVENTION

The present invention is described below in further detail.
(I) Compound Represented by Formula (1)

In Formula (1), R1 represents a di-$C_{1-6}$ alkoxyphenyl group, i.e., a phenyl group substituted with two $C_{1-6}$ straight- or branched-chain alkoxy groups. Specific examples include 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3-diethoxyphenyl, 2,4-diethoxyphenyl, 2,5-diethoxyphenyl, 2,6-diethoxyphenyl, 3,4-diethoxyphenyl, 3,5-diethoxyphenyl, 2,3-dipropoxyphenyl, 2,4-dipropoxyphenyl, 2,5-dipropoxyphenyl, 2,6-dipropoxyphenyl, 3,4-dipropoxyphenyl, 3,5-dipropoxyphenyl, 2,3-diisopropoxyphenyl, 2,4-diisopropoxyphenyl, 2,5-diisopropoxyphenyl, 2,6-diisopropoxyphenyl, 3,4-diisopropoxyphenyl, 3,5-diisopropoxyphenyl, 2,3-dibutoxyphenyl, 2,4-dibutoxyphenyl, 2,5-dibutoxyphenyl, 2,6-dibutoxyphenyl, 3,4-dibutoxyphenyl, 3,5-dibutoxyphenyl, 2,3-dipentoxyphenyl, 2,4-dipentoxyphenyl, 2,5-dipentoxyphenyl, 2,6-dipentoxyphenyl, 3,4-dipentoxyphenyl, 3,5-dipentoxyphenyl, 2,3-dihexyloxyphenyl, 2,4-dihexyloxyphenyl, 2,5-dihexyloxyphenyl, 2,6-dihexyloxyphenyl, 3,4-dihexyloxyphenyl, 3,5-dihexyloxyphenyl and the like. R1 in Formula (1) is preferably a 3,4-di-$C_{1-6}$ alkoxyphenyl group, more preferably a 3,4-di-$C_{1-3}$ alkoxyphenyl group, and especially preferably a 3,4-dimethoxyphenyl group or a 3,4-diethoxyphenyl group.

In Formula (1), R2 represents (a) a phenyl group, (b) a naphthyl group, (c) a pyridyl group, (d) a furyl group, (e) a thienyl group, (f) an isoxazolyl group, (g) a thiazolyl group, (h) a pyrrolyl group, (i) an imidazolyl group, (j) a tetrazolyl group, (k) a pyrazinyl group, (l) a thienothienyl group, (m) a benzothienyl group, (n) an indolyl group, (O) a benzimidazolyl group, (p) an imidazolyl group, (q) a quinolyl group, (r) a 3,4-dihydrocarbostyryl group, (s) a quinoxalinyl group, or (t) a 1,3-benzodioxolyl group.

When R2 is (a) a phenyl group, the phenyl ring of the phenyl group may be substituted with one or more members selected from the group consisting of (a-1) hydroxy groups, (a-2) halogen atoms, (a-3) unsubstituted or halogen-unsubstituted $C_{1-6}$ alkyl groups, (a-4) unsubstituted or halogen-substituted $C_{1-6}$ alkoxy groups, (a-5) $C_{1-6}$ alkoxy-$C_{1-6}$ alkoxy groups, (a-6) amino-$C_{1-6}$ alkoxy groups which may be substituted with a $C_{1-6}$ alkyl group or groups, (a-7) methylenedioxy groups, (a-8) carboxyl groups, (a-9) phenoxy groups, (a-10) $C_{1-6}$ alkoxycarbonyl groups, (a-11) $C_{1-6}$ alkanoyloxy groups, (a-12) $C_{1-6}$ alkanoyl groups, (a-13) cyano groups, (a-14) nitro groups, (a-15) $C_{1-6}$ alkylcarbamoyl groups, (a-16) aminosulfonyl groups, (a-17) amino groups which may be substituted with a $C_{1-6}$ alkyl group or groups, (a-18) $C_{1-6}$ alkanoylamino groups, (a-19) $C_{1-6}$ alkylthio groups, (a-20) phenyl groups, (a-21) pyrazolyl groups, (a-22) imidazolyl groups, (a-23) triazolyl groups, (a-24) morpholino groups, (a-25) pyrrolidinyl groups, and (a-26) piperazinylcarbonyl groups which may be substituted with a $C_{1-6}$ alkyl group or groups. When R2 is a substituted phenyl group, the number of substituents is not limited, and may be, for example, 1 to 5, and preferably 1 to 3.

When R2 is (c) a pyridyl group, the pyridine ring of the pyridyl group may be substituted with one or more members selected from the group consisting of (c-1) hydroxy groups, (c-2) $C_{1-6}$ alkyl groups, (c-3) $C_{1-6}$ alkoxy groups, and (c-4) phenyl-$C_{1-6}$ alkoxy groups. When R2 is a substituted pyridyl group, the number of substituents is not limited, and may be, for example, 1 to 4, and preferably 1 to 3.

When R2 is (d) a furyl group, the furan ring of the furyl group may be substituted with a $C_{1-6}$ alkyl group or groups. When R2 is a substituted furyl group, the number of substituents is not limited, and may be, for example, 1 to 3, and preferably 1 or 2.

When R2 is (e) a thienyl group, the thiophene ring of the thienyl group may be substituted with one or more members selected from the group consisting of (e-1) halogen atoms, (e-2) $C_{1-6}$ alkyl groups, and (e-3) $C_{1-6}$ alkoxy groups. When R2 is a substituted thienyl group, the number of substituents is not limited, and may be, for example, 1 to 3, and preferably 1 or 2.

When R2 is (f) an isooxazolyl group, the isooxazolyl ring of the isooxazolyl group may be substituted with a $C_{1-6}$ alkyl group or groups. When R2 is a substituted isooxazolyl group, the number of substituents is not limited, and may be, for example, 1 or 2.

When R2 is (g) a thiazolyl group, the thiazole ring of the thiazolyl group may be substituted with one or more members selected from the group consisting of (g-1) $C_{1-6}$ alkyl groups and (g-2) phenyl groups which may be substituted with a $C_{1-6}$ alkoxy group or groups. When R2 is a substituted thiazolyl group, the number of substituents is not limited, and may be, for example, 1 to 2.

When R2 is (h) a pyrrolyl group, the pyrrole ring of the pyrrolyl group may be substituted with a $C_{1-6}$ alkyl group or groups. When R2 is a substituted pyrrolyl group, the number of substituents is not limited, and may be, for example, 1 to 4, and preferably 1 or 2.

When R2 is (i) an imidazolyl group, the imidazole ring of the imidazolyl group may be substituted with a $C_{1-6}$ alkyl group or groups. When R2 is a substituted imidazolyl group, the number of substituents is not limited, and may be, for example, 1 to 3, and preferably 1 or 2.

When R2 is (o) a benzimidazolyl group, the benzimidazole ring of the benzimidazolyl group may be substituted with a $C_{1-6}$ alkyl group or groups. When R2 is a substituted benzimidazolyl group, the number of substituents is not limited, and may be, for example, 1 to 5, and preferably 1 to 3.

When R2 is (n) an indolyl group, the indole ring of the indolyl group may be substituted with a $C_{1-6}$ alkyl group or groups. When R2 is a substituted indolyl group, the number of substituents is not limited, and may be, for example, 1 to 6, and preferably 1 to 3.

When R2 is (r) a 1,2,3,4-tetrahydroquinolyl group, the 1,2,3,4-tetrahydroquinoline ring of the 1,2,3,4-tetrahydroquinolyl group may be substituted with an oxo group or groups. When R2 is an oxo-substituted 1,2,3,4-tetrahydroquinolyl group, the number of oxo groups is not limited, and may be, for example, 1 to 3, and preferably 1 or 2.

The terms used in the description of the groups represented by R2 in Formula (1) are defined as follows.

Halogen atoms include fluorine atoms, chlorine atoms, bromine atoms, iodine atoms and the like.

$C_{1-6}$ alkyl groups are straight- or branched-chain alkyl groups with 1 to 6 carbon atoms. Examples include methyl, ethyl, n-propyl, isopropyl, n-butyl, isobutyl, tert-butyl, sec-butyl, n-pentyl, neopentyl, n-hexyl, isohexyl, 3-methylpentyl, etc.

Unsubstituted or halogen-substituted $C_{1-6}$ alkyl groups are straight- or branched-chain alkyl groups with 1 to 6 carbon atoms as defined above, or such alkyl groups substituted with 1 to 7 halogen atoms. Examples include methyl, ethyl, n-propyl, isopropyl, n-butyl, isobutyl, tert-butyl, sec-butyl, n-pentyl, neopentyl, n-hexyl, isohexyl, 3-methylpentyl, fluoromethyl, difluoromethyl, trifluoromethyl, chloromethyl, dichloromethyl, trichloromethyl, bromomethyl, dibromomethyl, dichlorofluoromethyl, 2,2,2-trifluoroethyl, pentafluoroethyl, 2-chloroethyl, 3,3,3-trifluoropropyl, heptafluoropropyl, heptafluoroisopropyl, 3-chloropropyl, 2-chloropropyl, 3-bromopropyl, 4,4,4-trifluorobutyl, 4,4,4,3,3-pentafluorobutyl, 4-chlorobutyl, 4-bromobutyl, 2-chlorobutyl, 5,5,5-trifluoropentyl, 5-chloropentyl, 6,6,6-trifluorohexyl, 6-chlorohexyl, etc.

$C_{1-6}$ alkoxy groups are groups composed of a $C_{1-6}$ alkyl group as defined above and oxygen. Examples include methoxy, ethoxy, n-propoxy, isopropoxy, n-butoxy, isobutoxy, tert-butoxy, sec-butoxy, n-pentoxy, neopentoxy, n-hexyloxy, isohexyloxy, 3-methylpentoxy, etc.

Unsubstituted or halogen-substituted $C_{1-6}$ alkoxy groups are $C_{1-6}$ alkoxy groups as defined above, or such alkoxy groups substituted with 1 to 7 halogen atoms. Examples include methoxy, ethoxy, n-propoxy, isopropoxy, n-butoxy, isobutoxy, tert-butoxy, sec-butoxy, n-pentoxy, neopentoxy, n-hexyloxy, isohexyloxy, 3-methylpentoxy, fluoromethoxy, difluoromethoxy, trifluoromethoxy, chloromethoxy, dichloromethoxy, trichloromethoxy, bromomethoxy, dibromomethoxy, dichlorofluoromethoxy, 2,2,2-trifluoroethoxy, pentafluoroethoxy, 2-chloroethoxy, 3,3,3-trifluoropropoxy, heptafluoropropoxy, heptafluoroisopropoxy, 3-chloropropoxy, 2-chloropropoxy, 3-bromopropoxy, 4,4,4-trifluorobutoxy, 4,4,4,3,3-pentafluorobutoxy, 4-chlorobutoxy, 4-bromobutoxy, 2-chlorobutoxy, 5,5,5-trifluoropentoxy, 5-chloropentoxy, 6,6,6-trifluorohexyloxy, 6-chlorohexyloxy, etc.

$C_{1-6}$ alkoxy-$C_{1-6}$ alkoxy groups are $C_{1-6}$ alkoxy groups substituted with 1 to 7 $C_{1-6}$ alkoxy groups as defined above. Examples include methoxymethoxy, 2-methoxyethoxy, 3-methoxypropoxy, 4-methoxybutoxy, 5-methoxypentoxy, 6-methoxyhexyloxy, ethoxymethoxy, 1-ethoxyethoxy, 2-ethoxyethoxy, 3-ethoxypropoxy, 2-isopropoxyethoxy, tert-butoxymethoxy, 2-(tert-butoxy)ethoxy, 3-(tert-butoxy)propoxy, 6-(tert-butoxy)hexyloxy, 4-(tert-butoxy)butoxy, etc.

Amino-$C_{1-6}$ alkoxy groups which may be substituted with a $C_{1-6}$ alkyl group or groups are aminoalkoxy groups in which the alkoxy moiety is a $C_{1-6}$ straight- or branched-chain alkoxy group and in which 1 to 2 $C_{1-6}$ alkyl groups may be substituted on the nitrogen atom. Examples of such aminoalkoxy groups include aminomethoxy, 2-aminoethoxy, 1-aminoethoxy, 3-aminopropoxy, 4-aminobutoxy, 5-aminopentyloxy, 6-aminohexyloxy, 1,1-dimethyl-2-aminoethoxy, 2-methyl-3-aminopropoxy, methylaminomethoxy, 1-ethylaminoethoxy, 2-propylaminoethoxy, 3-isopropylaminopropoxy, 4-isopropylaminobutoxy, 4-butylaminobutoxy, 4-tert-butylaminobutoxy, 5-pentylaminopentyloxy, 6-hexylaminohexyloxy, dimethylaminomethoxy, 2-diethylaminoethoxy, 2-dimethylaminoethoxy, (N-ethyl-N-propylamino)methoxy, 2-(N-methyl-N-hexylamino)ethoxy, etc.

$C_{1-6}$ alkoxycarbonyl groups include, for example, methoxycarbonyl, ethoxycarbonyl, propoxycarbonyl, isopropoxycarbonyl, butoxycarbonyl, tert-butoxycarbonyl, pentyloxycarbonyl, hexyloxycarbonyl, and other $C_{1-6}$ straight- or branched-chain alkoxycarbonyl groups.

$C_{1-6}$ alkanoyloxy groups include, for example, formyloxy, acetyloxy, propionyloxy, butyryloxy, isobutyryloxy, pentanoyloxy, tert-butylcarbonyloxy, hexanoyloxy, and other $C_{1-6}$ straight- or branched-chain alkanoyloxy groups.

$C_{1-6}$ alkanoyl groups include, for example, formyl, acetyl, propionyl, butyryl, isobutyryl, pentanoyl, tert-butylcarbonyl, hexanoyl, and other $C_{1-6}$ straight- or branched-chain alkanoyl groups.

$C_{1-6}$ alkylcarbamoyl groups include, for example, methylcarbamoyl, ethylcarbamoyl, propylcarbamoyl, isopropylcarbamoyl, butylcarbamoyl, tert-butylcarbamoyl, pentylcarbamoyl, hexylcarbamoyl, and other $C_{1-6}$ straight- or branched-chain alkylcarbamoyl groups.

Amino groups which may be substituted with a $C_{1-6}$ alkyl group or groups include, for example, amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, and other amino groups which may have 1 or 2 $C_{1-6}$ straight- or branched-chain alkyl groups as substituents.

$C_{1-6}$ alkanoylamino groups include, for example, formylamino, acetylamino, propionylamino, butyrylamino, isobutyrylamino, pentanoylamino, tert-butylcarbonylamino, hexanoylamino, and other $C_{1-6}$ straight- or branched-chain alkanoylamino groups.

$C_{1-6}$ alkylthio groups include, for example, methylthio, ethylthio, propylthio, isopropylthio, butylthio, tert-butylthio, pentylthio, hexylthio, and other $C_{1-6}$ straight- or branched-chain alkylthio groups.

Piperazinylcarbonyl groups which may be substituted with a $C_{1-6}$ alkyl group or groups include, for example, piperazinylcarbonyl, methylpiperazinylcarbonyl, ethylpiperazinylcarbonyl, propylpiperazinylcarbonyl, isopropylpiperazinylcarbonyl, isopropylpiperazinylcarbonyl, butylpiperazinylcarbonyl, tert-butylpiperazinylcarbonyl, pentylpiperazinylcarbonyl, hexylpiperazinylcarbonyl, and other piperazinylcarbonyl groups which may have a $C_{1-6}$ straight- or branched-chain alkyl group or groups as substituents.

Phenyl-$C_{1-6}$ alkoxy groups include, for example, benzyloxy, phenethyloxy, 3-phenylpropoxy, 4-phenylbutoxy, 5-phenylpentoxy, 6-phenylhexyloxy, etc.

R2 in Formula (1) is preferably (a) a phenyl group, (c) a pyridyl group, (d) a furyl group, (e) a thienyl group, (g) a thiazolyl group, (h) a pyrrolyl group or (i) an imidazolyl group, and more preferably (a) a phenyl group, (c) a pyridyl group or (g) a thiazolyl group.

In Formula (1), A is (i) —CO—B— wherein B is a $C_{1-6}$ alkylene group, (ii) —CO—Ba— wherein Ba is a $C_{2-6}$ alkenylene group, (iii) —CH(OH)—B— wherein B is as defined above, (iv) —COCH(COOR3)-Bb- wherein R3 is a $C_{1-6}$ alkyl group and Bb is a $C_{1-6}$ alkylene group, or (v) -Bc- wherein Bc is a $C_{2-6}$ alkylene group. In A in Formula (1), B, Ba or Bb is bound to the thiazole ring.

The terms used in the description of the groups represented by A in Formula (1) are defined as follows.

$C_{1-6}$ alkylene groups include, for example, methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene and other $C_{1-6}$ straight- or branched-chain alkylene groups.

$C_{2-6}$ alkylene groups include, for example, ethylene, trimethylene, 2-methyltrimethylene, 2,2-dimethyltrimethylene, 1-methyltrimethylene, methylmethylene, ethylmethylene, tetramethylene, pentamethylene, hexamethylene and other $C_{1-6}$ straight- or branched-chain alkylene groups.

$C_{2-6}$ alkenylene groups include, for example, vinylidene, propylene, butenylene and other $C_{1-6}$ straight- or branched-chain alkenylene groups.

The term "$C_{1-6}$ alkyl group" used in the description of A in Formula (1) has the same definition as used in the description of R2.

A in Formula (1) is preferably (i) —CO—B— wherein B is a methylene group, an ethylene group or a trimethylene group; (ii) —CO—Ba— wherein Ba is a vinylidene group; (iii) —CH(OH)—B— wherein B is a methylene group or an ethylene group, (iv) —COCH(COOR3)-Bb- wherein R3 is a methyl group, an ethyl group or a tert-butyl group and Bb is a methylene group or a ethylene group; or (v) -Bc- wherein Bc is an ethylene group, a trimethylene group or a tetramethylene group; and more preferably, (i) —CO—B— wherein B is an ethylene group, (iii) —CH(OH)—B— wherein B is an ethylene group, (iv) —COCH(COOR3)-Bb- wherein R3 is a methyl group and Bb is a methylene group, or (v) -Bc- wherein Bc is a trimethylene group.

The compound represented by Formula (1) encompasses within its scope the following Compounds (1-1) to (1-3):

Compound (1-1)

A compound in which R1 is a 3,4-di-$C_{1-6}$ alkoxyphenyl group, and preferably a 3,4-dimethoxyphenyl group or a 3,4-diethoxyphenyl group;

R2 is (a) a phenyl group, (c) a pyridyl group, (d) a furyl group, (e) a thienyl group, (g) a thiazolyl group, (h) a pyrrolyl group or (i) an imidazolyl group; and A is (i) —CO—B—, (ii) —CO—Ba—, (iii) —CH(OH)—B—, (iv) —COCH(COOR3)-Bb- or (v) -Bc-.

Compound (1-2)

A compound in which R1 is a 3,4-di-$C_{1-6}$ alkoxyphenyl group, and preferably a 3,4-dimethoxyphenyl group or a 3,4-diethoxyphenyl group;

R2 is (a) a phenyl group, (c) a pyridyl group, (d) a furyl group, (e) a thienyl group, (g) a thiazolyl group, (h) a pyrrolyl group or (i) an imidazolyl group; and A is (i) —CO—B— wherein B is a methylene group, an ethylene group or a trimethylene group, (ii) —CO—Ba— wherein Ba is a vinylidene group, (iii) —CH(OH)—B— wherein B is a methylene group or an ethylene group, (iv) —COCH(COOR3)-Bb- wherein R3 is a methyl group, an ethyl group or a tert-butyl group, and Bb is a methylene group or an ethylene group, or (v) -Bc- wherein Bc is an ethylene group, a trimethylene group or a tetramethylene group.

Compound (1-3)

A compound in which R1 is a 3,4-di-$C_{1-6}$ alkoxyphenyl group, and preferably a 3,4-dimethoxyphenyl group or a 3,4-diethoxyphenyl group;

R2 is (a) a phenyl group, (c) a pyridyl group or (g) a thiazolyl group; and

A is (i) —CO—B— wherein B is ethylene, (iii) —CH(OH)—B— wherein B is ethylene, (iv) —COCH(COOR3)-Bb- wherein R3 is a methyl group and Bb is a methylene group, or (v) -Bc- wherein Bc is a trimethylene group.

Some of the compounds represented by Formula (1) have optical isomers. Some of the compounds represented by Formula (1) and optical isomers thereof form acid addition salts or salts with bases. The present invention encompasses optical isomers of the compounds represented by Formula (1), as well as salts of the compounds represented by Formula (1) and optical isomers thereof.

(II) Production Process for the Compound of Formula (1)

The compound of Formula (1), optical isomers thereof, and salts thereof can be prepared by various synthetic processes selected according to the basic skeleton, types of substituents, etc. Typical production processes for the compound of Formula (1) are described below.

<Process 1>

In Process 1, the compound of Formula (1) is produced by reacting the compound of Formula (2) with the compound of Formula (3).

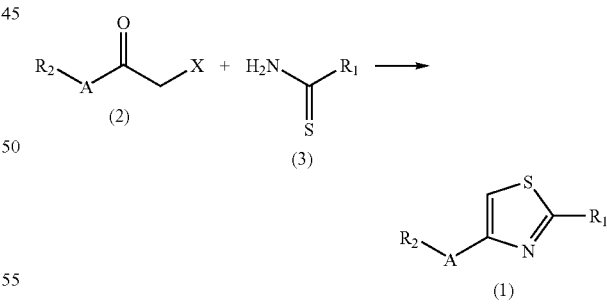

wherein R1, R2, and A are as defined above; and X is a halogen atom.

A suitable ratio of the compound of Formula (3) to the compound of Formula (2) is usually 0.5 to 5 mol, and preferably 0.5 to 3 mol, of the compound of Formula (3) per mol of the compound of Formula (2).

The reaction of the compound of Formula (2) with the compound of Formula (3) is usually carried out in a suitable solvent. A wide variety of known solvents can be used as long as they do not hinder the reaction. Examples of usable solvents include dimethylformamide (DMF), dimethylsulfoxide (DMSO), acetonitrile and other aprotic polar solvents; acetone, methyl ethyl ketone and other ketone solvents; benzene, toluene, xylene, tetralin, liquid paraffin and other hydrocarbon solvents; methanol, ethanol, isopropanol, n-butanol, tert-butanol and other alcohol solvents; tetrahydrofuran (THF), dioxane, dipropyl ether, diethyl ether, dimethoxyethane, diglyme and other ether solvents; ethyl acetate, methyl acetate and other ester solvents; mixtures thereof; etc. Such solvents may contain water.

The reaction of the compound of Formula (2) with the compound of Formula (3) is usually performed by continuing stirring at −20 to 200° C., and preferably at 0 to 150° C., for 30 minutes to 60 hours, and preferably for 1 to 30 hours.

The compound of Formula (3) used as a starting material is a known compound. Formula (2) encompasses novel compounds. Production processes for the compounds are described hereinafter.

The reaction mixture obtained by the above reaction is, for example, cooled and subjected to an isolation procedure, such as filtration, concentration, extraction and/or the like, to separate a crude reaction product, which is further subjected, as required, to a conventional purification procedure, such as column chromatography, recrystallization and/or the like, to thereby isolate and purify the compound of Formula (1).

<Process 2>

In Process 2, the compound of Formula (4) is reacted with the compound of Formula (5) in the presence of a basic compound, to produce the compound of Formula (1) wherein A is —COCH(COOR3)-Bb- (hereinafter referred to as "Compound (1a)").

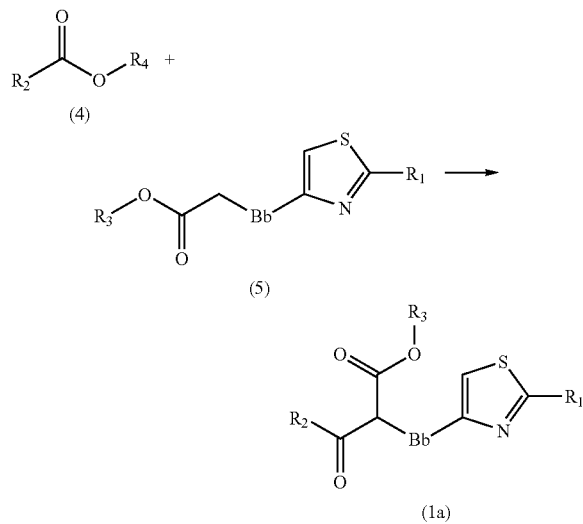

wherein R1, R2, R3 and Bb are as defined above; and R4 is a $C_{1-6}$ alkyl group.

The ratio of the compound of Formula (5) to the compound of Formula (4) is usually 0.5 to 5 mol, and preferably 0.5 to 3 mol, of the compound of Formula (5) per mol of the compound of Formula (4).

The reaction of the compound of Formula (4) with the compound of Formula (5) is usually carried out in a suitable solvent. A wide variety of known solvents can be used as long as they do not hinder the reaction. Examples of usable solvents include dimethylformamide (DMF), dimethylsulfoxide (DMSO), N-methylpyrrolidone (NMP) and other aprotic polar solvents; benzene, toluene, xylene, tetralin, liquid paraffin and other hydrocarbon solvents; methanol, ethanol, isopropanol, n-butanol, tert-butanol and other alcohol solvents; tetrahydrofuran (THF), dioxane, dipropyl ether, diethyl ether, dimethoxyethane, diglyme and other ether solvents; mixtures thereof; etc. Such solvents may contain water.

The reaction of the compound of Formula (4) with the compound of Formula (5) is usually carried out by continuing stirring at 0 to 200° C., and preferably at room temperature to 150° C., for 30 minutes to 60 hours, and preferably 1 to 50 hours.

A wide variety of known basic compounds are usable, including, for example, alkali metals, metal hydrides, metal alkoxides, carbonates, hydrogencarbonates and other inorganic basic compounds; acetate and other organic basic compounds; etc.

Examples of alkali metals include lithium, sodium, potassium, etc. Examples of metal hydrides include sodium hydride, potassium hydride, etc. Examples of metal alkoxides include sodium methoxide, sodium ethoxide, potassium tert-butoxide, sodium tert-butoxide, etc. Examples of carbonates include sodium carbonate, potassium carbonate, etc. Examples of hydrogencarbonates include sodium hydrogencarbonate, potassium hydrogencarbonate, etc. Inorganic basic compounds further include sodium amide, lithium diisopropylamide, lithium hexamethyldisilazide, sodium hexamethyldisilazide, n-butyl lithium, sec-butyl lithium, methyl lithium, etc.

Examples of acetates include sodium acetate, potassium acetate, etc. Other examples of organic basic compounds include triethylamine, trimethylamine, diisopropylethylamine, pyridine, dimethylaniline, 1-methylpyrrolidine, N-methylmorpholine, 1,5-diazabicyclo-[4.3.0]nonene-5 (DBN), 1,8-diazabicyclo[5.4.0]undecene-7 (DBU), 1,4-diazabicyclo[2.2.2]octane (DABCO), 2-tert-butylimino-2-diethylamino-1,3-dimethyl-perhydro-1,3,2-diazaphosphorine (BEMP), etc.

Such a basic compound is used in an amount of usually 0.1 to 5 mol, and preferably 0.5 to 3 mol per mol of the compound of Formula (5).

The reaction mixture obtained by the above reaction is, for example, cooled and subjected to an isolation procedure, such as filtration, concentration, extraction and/or the like, to separate a crude reaction product, which is further subjected, as required, to a conventional purification procedure, such as column chromatography, recrystallization and/or the like, to thereby isolate and purify the Compound (1a).

<Process 3>

In Process 3, the compound of Formula (1) in which A is —COCH(COOR3)-Bb- (Compound (1a)) is hydrolyzed and decarboxylated to produce the compound of Formula (1) in which A is —CO—B— (hereinafter referred to as "Compound (1b)").

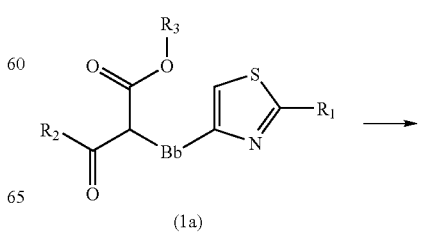

-continued

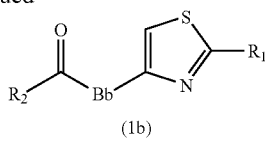

(1b)

wherein R1, R2, R3, B and Bb are as defined as above.

The hydrolysis and decarboxylation of Compound (1a) is carried out under acidic conditions. For example, an acid is added to a suspension or solution of Compound (1a) in a suitable solvent, and the resulting mixture was stirred at 0 to 120° C.

Usable solvents include water, alcohol solvents such as methanol, ethanol, isopropanol, ethylene glycol, etc., acetonitrile, acetone, toluene, DMF, DMSO, acetic acid, trifluoroacetic acid, mixtures thereof, etc. Usable acids include trifluoroacetic acid, acetic acid and other organic acids; hydrochloric acid, bromic acid, hydrobromic acid, sulfuric acid and other inorganic acids; etc. An organic acid such as trifluoroacetic acid, acetic acid or the like can also be used as a reaction solvent. The reaction temperature is usually 0 to 120° C., preferably room temperature to 100° C., and more preferably room temperature to 80° C. The reaction time is usually 30 minutes to 24 hours, preferably 30 minutes to 12 hours, and more preferably 1 to 8 hours.

The reaction mixture obtained by the above reaction is, for example, cooled and subjected to an isolation procedure, such as filtration, concentration, extraction and/or the like, to separate a crude reaction product, which is further subjected, as required, to a conventional purification procedure, such as column chromatography, recrystallization and/or the like, to thereby isolate and purify the Compound (1b).

<Process 4>

In Process 4, the compound of Formula (6) is reacted with the compound of Formula (7) to produce the compound of Formula (1) in which A is —CO—B— (hereinafter referred to as "Compound (1b)").

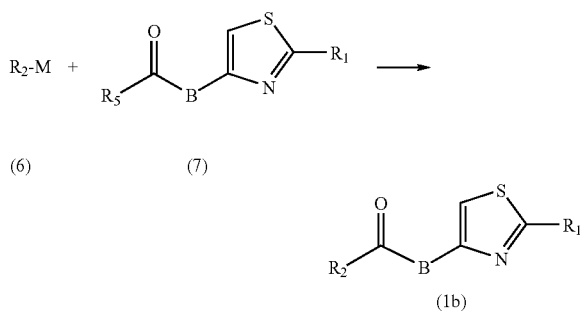

wherein R1, R2 and B are as defined above; R5 is a $C_{1-6}$ alkoxy group or $CH_3ON(CH_3)$—; M is a lithium atom or —MgX; and X is a halogen atom.

The ratio of the compound of Formula (7) to the compound of Formula (6) is usually 0.5 to 5 mol, and preferably 0.5 to 3 mol of the compound of Formula (7) per mol of the compound of Formula (6).

The reaction of the compound of Formula (6) with the compound of Formula (7) is usually performed in a suitable solvent, which can be selected from a wide variety of known solvents, as long as the solvent does not hinder the reaction. Examples of such solvents include benzene, toluene, xylene, tetralin, liquid paraffin and other hydrocarbon solvents; tetrahydrofuran (THF), dioxane, dipropyl ether, diethyl ether, dimethoxyethane, diglyme and other ether solvents; mixtures thereof; etc.

The reaction of the compound of Formula (6) with the compound of Formula (7) is usually performed by continuing stirring at −100 to 200° C., and preferably at −100 to 100° C., for 30 minutes to 60 hours, and preferably 1 to 50 hours.

The reaction mixture obtained by the above reaction is, for example, cooled and subjected to an isolation procedure, such as filtration, concentration, extraction and/or the like, to separate a crude reaction product, which is further subjected, as required, to a conventional purification procedure, such as column chromatography, recrystallization and/or the like, to thereby isolate and purify the Compound (1b).

<Process 5>

In Process 5, the compound of Formula (1b) is reacted in the presence of a reducing agent to produce the compound of Formula (1) in which A is —CH(OH)—B— (hereinafter referred to as "Compound (1c)").

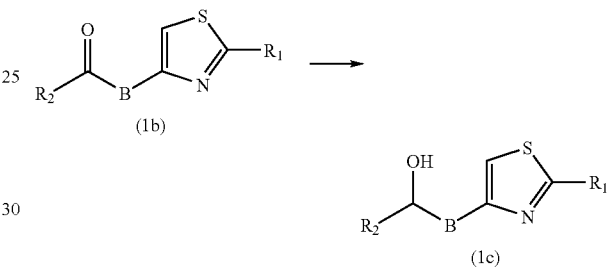

wherein R1, R2 and B are as defined above.

Examples of solvents usable in the above reaction include water; methanol, ethanol, isopropanol, butanol, tert-butanol, ethylene glycol and other lower alcohols; ethyl acetate, methyl acetate and other ester solvents; diethyl ether, tetrahydrofuran, dioxane, monoglyme, diglyme and other ethers; benzene, toluene, xylene and other aromatic hydrocarbons; dichloromethane, dichloroethane, chloroform, carbon tetrachloride and other halogenated hydrocarbons; mixtures thereof; etc.

Examples of usable reducing agents include sodium borohydride, lithium aluminium hydride, diisobutylaluminum hydride and other hydride reducing agents, and mixtures of such hydride reducing agents.

When a hydride reducing agent is used as a reducing agent, a suitable reaction temperature is usually about −80 to about 100° C., and preferably about −80 to about 70° C., and the reaction is completed in about 30 minutes to about 100 hours. The amount of the hydride reducing agent to be used is usually about 1 to about 20 mol, and preferably about 1 to about 6 mol per mol of Compound (1b). In particular, when lithium aluminium hydride is used as a reducing agent, it is preferred to use as a solvent an ether, such as diethyl ether, tetrahydrofuran, dioxane, monoglyme, diglyme or the like, or an aromatic hydrocarbon, such as benzene, toluene, xylene or the like.

The reaction mixture obtained by the above reaction is, for example, cooled and subjected to an isolation procedure, such as filtration, concentration, extraction and/or the like, to separate a crude reaction product, which is further subjected, as required, to a conventional purification procedure, such as column chromatography, recrystallization and/or the like, to thereby isolate and purify the Compound (1c).

<Process 6>

In Process 6, the compound of Formula (6) is reacted with the compound of Formula (8) to produce Compound (1c).

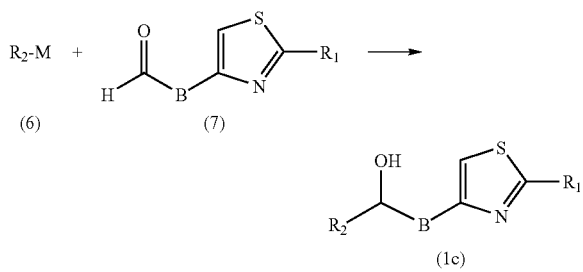

wherein R1, R2, B and M are as defined above.

The reaction in Process 6 is performed under the same reaction conditions as for the reaction in Process 4.

<Process 7>

In Process 7, Compound (1c) is reacted in a suitable solvent in the presence of an oxidizing agent to produce Compound (1b).

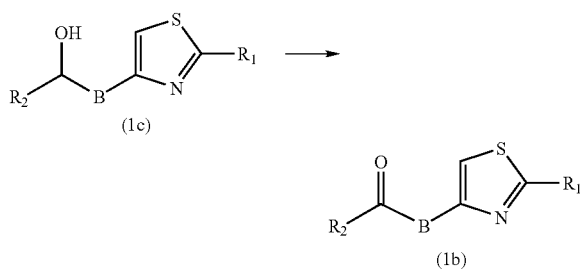

wherein R1, R2 and B are as defined above.

The solvent for use in Process 7 can be selected from a wide variety of known solvents, as long as it does not hinder the reaction. Examples of usable solvents include dimethylformamide (DMF), dimethyl sulfoxide (DMSO), N-methylpyrrolidone (NMP), acetonitrile and other aprotic polar solvents; benzene, toluene, xylene, tetralin, liquid paraffin and other hydrocarbon solvents; ethyl acetate, methyl acetate and other ester solvents; tetrahydrofuran (THF), dioxane, dipropyl ether, diethyl ether, dimethoxyethane, diglyme and other ether solvents; dichloromethane, dichloroethane, chloroform, carbon tetrachloride and other halogenated hydrocarbons; mixtures thereof; etc. Such solvents may contain water.

In Process 7, the oxidizing agent can selected from a wide variety of known oxidizing agents. Examples of usable oxidizing agents include dimethyl sulfoxide (DMSO)-sulfur trioxide-pyridine, dimethyl sulfoxide (DMSO)-oxalyl chloride-triethylamine, pyridinium chlorochromate (PCC), chromic acid, manganese dioxide, etc.

The amount of oxidizing agent to be used is usually about 1 about 20 mol, and preferably about 1 to about 6 mol per mol of Compound (1c).

The reaction mixture obtained by the above reaction is, for example, cooled and subjected to an isolation procedure, such as filtration, concentration, extraction and/or the like, to separate a crude reaction product, which is further subjected, as required, to a conventional purification procedure, such as column chromatography, recrystallization and/or the like, to thereby isolate and purify the Compound (1b).

<Process 8>

In Process 8, the compound of Formula (8) is reacted with the compound of Formula (9) in the presence of a basic compound to produce the compound of Formula (1) in which A is —CO—Ba— (hereinafter referred to as "Compound (1d)").

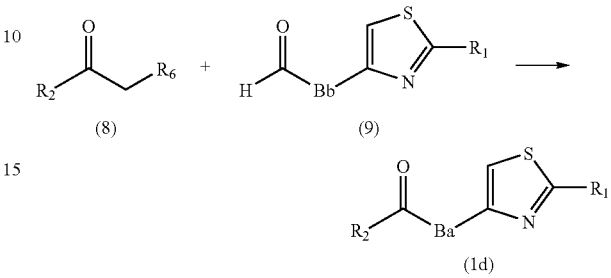

wherein R1, R2 and Ba are as defined above; R6 is a hydrogen atom or —PO(OR7)$_2$; Bd is —(CH$_2$)n-; n is an integer from 0 to 4; and R7 is a $C_{1-6}$ alkyl group.

The ratio of the compound of Formula (9) to the compound of Formula (8) is usually 0.5 to 5 mol, and preferably 0.5 to 3 mol of the compound of Formula (9) per mol of the compound of Formula (8).

The reaction of the compound of Formula (8) with the compound of Formula (9) is usually carried out in a suitable solvent. A wide variety of known solvents can be used as long as they do not hinder the reaction. Examples of usable solvents include dimethylformamide (DMF), dimethylsulfoxide (DMSO), N-methylpyrrolidone (NMP) and other aprotic polar solvents; benzene, toluene, xylene, tetralin, liquid paraffin and other hydrocarbon solvents; methanol, ethanol, isopropanol, n-butanol, tert-butanol and other alcohol solvents; tetrahydrofuran (THF), dioxane, dipropyl ether, diethyl ether, dimethoxyethane, diglyme and other ether solvents; mixtures thereof; etc. Such solvents may contain water.

The reaction of the compound of Formula (8) with the compound of Formula (9) is usually carried out by continuing stirring at 0 to 200° C., and preferably at room temperature to 150° C., for 30 minutes to 60 hours, and preferably 1 to 50 hours.

A wide variety of known basic compounds are usable, including, for example, alkali metals, metal hydrides, metal alkoxides, carbonates, hydrogencarbonates and other inorganic basic compounds; acetates and other organic basic compounds; etc.

Examples of alkali metals include lithium, sodium, potassium, etc. Examples of metal hydrides include sodium hydride, potassium hydride, etc. Examples of metal alkoxides include sodium methoxide, sodium ethoxide, potassium tert-butoxide, sodium tert-butoxide, etc. Examples of carbonates include sodium carbonate, potassium carbonate, etc. Examples of hydrogencarbonates include sodium hydrogencarbonate, potassium hydrogencarbonate, etc. Inorganic basic compounds include, in addition to the above compounds, sodium amide, lithium diisopropylamide, lithium hexamethyldisilazide, sodium hexamethyldisilazide, etc.

Examples of acetates include sodium acetate, potassium acetate, etc. Examples of organic basic compounds other than the above include triethylamine, trimethylamine, diisopropylethylamine, pyridine, dimethylaniline, 1-methylpyrrolidine, N-methylmorpholine, 1,5-diazabicyclo[4.3.0]nonene-5 (DBN), 1,8-diazabicyclo[5.4.0]-undecene-7 (DBU), 1,4-diazabicyclo[2.2.2]octane (DABCO), 2-tert-butylimino-2-diethylamino-1,3-dimethyl-perhydro-1,3,2-diazaphospholine (BEMP), etc.

It is suitable to use such a basic compound in an amount of 0.1 to 5 mol, preferably 0.5 to 3 mol per mol of the compound represented by Formula (8).

The reaction mixture obtained by the above reaction is, for example, cooled and subjected to an isolation procedure, such as filtration, concentration, extraction and/or the like, to separate a crude reaction product, which is further subjected, as required, to a conventional purification procedure, such as column chromatography, recrystallization and/or the like, to thereby isolate and purify the Compound (1d).

<Process 9>

In Process 9, Compound (1d) is reacted in the presence of a reducing agent to produce Compound (1b).

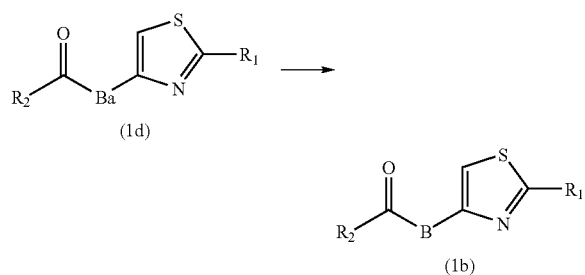

wherein R1, R2, Ba and B are as defined above.

Examples of reducing agents include hydrogen catalytic reducing agents, such as palladium-black, palladium-carbon, platinum oxide, platinum black, Raney nickel, etc.

When using a hydrogen catalytic reducing agent, it is usually suitable to perform the reaction in an hydrogen atmosphere at atmospheric normal pressure to about 20 atm, and preferably at atmospheric normal pressure to about 10 atm, or in the presence of a hydrogen donor, such as formic acid, ammonium formate, cyclohexene, hydrazine hydrate or the like, usually at about −30 to about 100° C., and preferably at about 0 to about 60° C. The reaction is usually completed in about 1 to about 12 hours. A suitable amount of the hydrogen catalytic reducing agent to be used is usually about 0.1 to about 40 parts by weight, and preferably about 1 to about 20 parts by weight, per 100 parts by weight of Compound (1d).

Examples of solvents usable in the reaction in Process 9 include water; methanol, ethanol, isopropanol, n-butanol, tert-butanol, ethylene glycol and other lower alcohols; ethyl acetate, methyl acetate and other ester solvents; dimethylformamide (DMF), N-methylpyrrolidone (NMP) and other aprotic polar solvents; diethyl ether, tetrahydrofuran, dioxane, monoglyme, diglyme and other ethers; benzene, toluene, xylene and other aromatic hydrocarbons; mixtures thereof; etc.

The reaction mixture obtained by the above reaction is, for example, cooled and subjected to an isolation procedure, such as filtration, concentration, extraction and/or the like, to separate a crude reaction product, which is further subjected, as required, to a conventional purification procedure, such as column chromatography, recrystallization and/or the like, to thereby isolate and purify the Compound (1b).

<Process 10>

In Process 10, Compound (1b) is subjected to a reduction reaction to produce the compound of Formula (1e) (hereinafter referred to as "Compound (1e)").

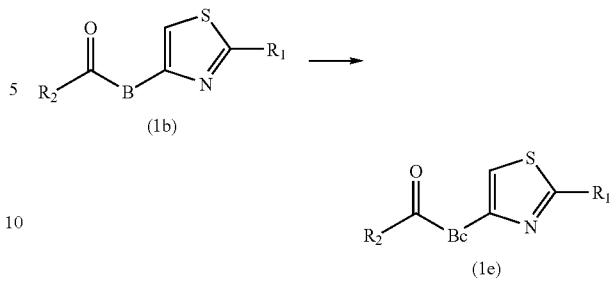

wherein R1, R2 and B are as defined above; and Bc is a C$_{2-6}$ alkylene group.

A wide variety of known reduction reactions can be employed as the above reduction reaction. For example, the reduction reaction can be performed by heating the compound in the presence of hydrazine and a basic compound in a suitable solvent.

Examples of usable solvents include water; methanol, ethanol, isopropanol, butanol, tert-butanol, ethylene glycol, diethylene glycol and other lower alcohols; dimethylformamide (DMF), N-methylpyrrolidone (NMP) and other aprotic polar solvents; diethyl ether, tetrahydrofuran, dioxane, monoglyme, diglyme and other ethers; benzene, toluene, xylene and other aromatic hydrocarbons; mixtures thereof; etc.

A wide variety of known basic compounds are usable, which include, for example, metal hydrides, metal alkoxides, hydroxides, carbonates, hydrogencarbonates and other inorganic basic compounds, etc.

Examples of metal hydrides include sodium hydride, potassium hydride, etc. Examples of metal alkoxides include sodium methoxide, sodium ethoxide, potassium tert-butoxide, etc. Examples of hydroxides include sodium hydroxide, potassium hydroxide, etc. Examples of carbonates include sodium carbonate, potassium carbonate, etc. Examples of hydrogencarbonates include sodium hydrogencarbonate, potassium hydrogencarbonate, etc. Inorganic basic compounds include, besides the above compounds, sodium amide and the like.

It is usually suitable to use such a basic compound in an amount of 0.1 to 2 mol, preferably 0.1 to 1 mol, and more preferably 0.1 to 0.5 mol per mol of Compound (1b).

A suitable reaction temperature is usually about 50 to about 250° C., and preferably about 100 to about 200° C., and the reaction is completed usually in about 30 minutes to about 10 hours.

The reaction mixture thus obtained is, for example, cooled and subjected to an isolation procedure, such as filtration, concentration, extraction and/or the like, to separate a crude reaction product, which is further subjected, as required, to a conventional purification procedure, such as column chromatography, recrystallization and/or the like, to thereby isolate and purify the Compound (1e).

<Process 11>

In Process 11, a halogen atom in the compound of Formula (1f) (hereinafter referred to as "Compound (1f)") is substituted by cyano to produce the compound of Formula (1g) (hereinafter referred to as "Compound (1g)").

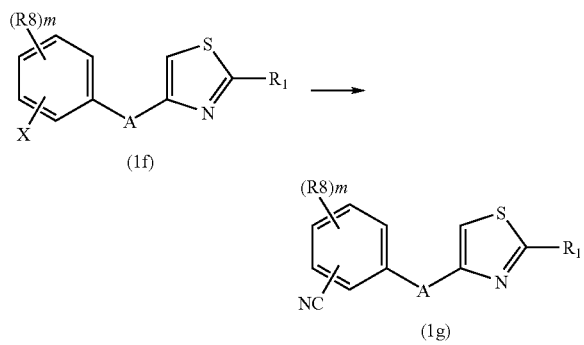

(1f)

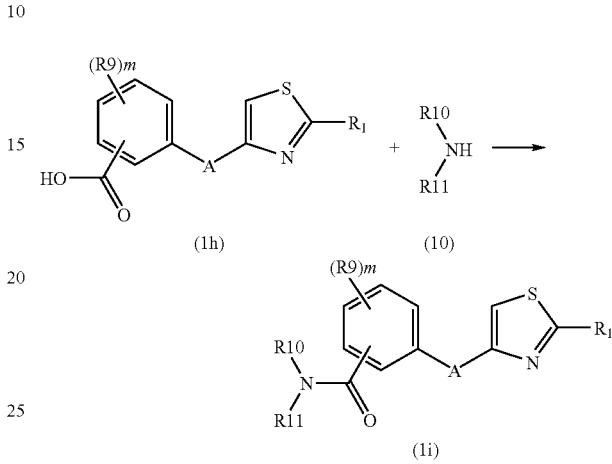

wherein R1, A and X are as defined above; R8 is a hydroxy group, an unsubstituted or halogen-substituted $C_{1-6}$ alkyl group, an unsubstituted or halogen-substituted $C_{1-6}$ alkoxy group, a $C_{1-6}$ alkoxy-$C_{1-6}$ alkoxy group, a phenyl-$C_{1-6}$ alkoxy group, an amino-$C_{1-6}$ alkoxy group which may be substituted with a $C_{1-6}$ alkyl group, a methylenedioxy group, a carboxyl group, a phenoxy group, a $C_{1-6}$ alkoxycarbonyl group, $C_{1-6}$ alkanoyloxy group, a $C_{1-6}$ alkanoyl group, a cyano group, a nitro group, a $C_{1-6}$ alkylcarbamoyl group, an aminosulfonyl group, an amino group which may be substituted with a $C_{1-6}$ alkyl group or groups, a $C_{1-6}$ alkanoylamino group, a $C_{1-6}$ alkylthio group, a phenyl group, a pyrazolyl group, an imidazolyl group, a triazolyl group, a morpholino group, a pyrrolidinyl group, or a piperazinylcarbonyl group which may be substituted with a $C_{1-6}$ alkyl group or groups; and m is an integer from 0 to 4.

A wide variety of known substitution reactions can be employed as the above substitution reaction. For example, the substitution reaction can be performed by heating the compound with a cyanide in the presence of a palladium catalyst in a suitable solvent.

Examples of palladium catalysts include tetrakistriphenylphosphine palladium and the like. A suitable amount of palladium catalyst is usually about 0.001 to about 0.4 mol, and preferably about 0.001 to about 0.2 mol per mol of Compound (10.

Examples of cyanides include zinc (II) cyanide and the like. It is usually suitable to use such a cyanide in an amount of 0.1 to 5 mol, preferably 0.5 to 3 mol, and more preferably 0.5 to 1 mol per mol of Compound (1f).

The solvent can be selected from a wide variety of known solvents, as long as it does not hinder the reaction. Examples of usable solvents include dimethylformamide (DMF), dimethylsulfoxide (DMSO), acetonitrile and other aprotic polar solvents; acetone, methyl ethyl ketone and other ketone solvents; benzene, toluene, xylene, tetralin, liquid paraffin and other hydrocarbon solvents; methanol, ethanol, isopropanol, n-butanol, tert-butanol and other alcohol solvents; tetrahydrofuran (THF), dioxane, dipropyl ether, diethyl ether, diglyme and other ether solvents; ethyl acetate, methyl acetate and other ester solvents; mixtures thereof; etc. Such solvents may contain water.

The reaction of the Compound (1f) with a cyanide is usually carried out at −100 to 200° C., and preferably at −100 to 100° C., for 30 minutes to 60 hours, and preferably 1 to 50 hours.

The reaction mixture thus obtained is, for example, cooled and subjected to an isolation procedure, such as filtration, concentration, extraction and/or the like, to separate a crude reaction product, which is further subjected, as required, to a conventional purification procedure, such as column chromatography, recrystallization and/or the like, to thereby isolate and purify the Compound (1g).

<Process 12>

In Process 12, the carboxylic acid moiety of the compound of Formula (1h) (hereinafter referred to as "Compound (1h)") is subjected to an amide bond formation reaction with the compound of Formula (10) (hereinafter referred to as "Compound 10") to produce the compound of Formula (1i) (hereinafter referred to as "Compound (1i)").

wherein R1, A and m are as defined above; R9 is a hydroxy group, a halogen atom, an unsubstituted or halogen-substituted $C_{1-6}$ alkyl group, an unsubstituted or halogen-substituted $C_{1-6}$ alkoxy group, a $C_{1-6}$ alkoxy-$C_{1-6}$ alkoxy group, a phenyl-$C_{1-6}$ alkoxy group, an amino-$C_{1-6}$ alkoxy group which may be substituted with a $C_{1-6}$ alkyl group or groups, a methylenedioxy group, a phenoxy group, a $C_{1-6}$ alkoxycarbonyl group, a $C_{1-6}$ alkanoyloxy group, a $C_{1-6}$ alkanoyl group, a cyano group, a nitro group, a $C_{1-6}$ alkylcarbamoyl group, an aminosulfonyl group, an amino group which may be substituted with a $C_{1-6}$ alkyl group, a $C_{1-6}$ alkanoylamino group, a $C_{1-6}$ alkylthio group, a phenyl group, a pyrazolyl group, an imidazolyl group, a triazolyl group, a morpholino group, a pyrrolidinyl group or a piperazinylcarbonyl group which may be substituted by a $C_{1-6}$ alkyl group or groups; m is an integer from 0 to 4; and R10 and R11 are independently each a hydrogen atom or a $C_{1-6}$ alkyl group, and may be bonded to each other via the adjacent nitrogen atom and a carbon atom or atoms or another nitrogen atom, to form a piperazine ring which may be substituted with a $C_{1-6}$ alkyl group or groups.

Conditions for known amide bond formation reactions can be employed in the amide formation reaction in Process 12. For example, the following reaction methods can be employed: (A) a mixed acid anhydride method, in which carboxylic acid (1h) is reacted with an alkyl halocarboxylate to form a mixed acid anhydride, which is then reacted with Compound (10); (B) an active ester method, in which carboxylic acid (1h) is converted to an activated ester, such as a phenyl ester, p-nitrophenyl ester, N-hydroxysuccinimide ester, 1-hydroxybenzotriazole ester or the like, or an activated amide with benzoxazoline-2-thione, and the activated ester or amide is reacted with Compound (10); (C) a carbodiimide method, in which carboxylic acid (1h) is subjected to a condensation reaction with Compound (10) in the presence of an activating agent, such as dicyclohexylcarbodiimide, 1-(3-dimethylaminopropyl)-3-ethylcarbodiimide (WSC), carbonyldiimidazole or the like; (D) other methods, for example, a method in which carboxylic acid (1h) is converted to a carboxylic anhydride using a dehydrating agent such as acetic anhydride, and the carboxylic anhydride is then reacted with Compound (10), or a method in which an ester of carboxylic acid (1h) with a lower alcohol is reacted with Compound (10) at a high pressure and a high temperature, a method in which an acid halide of carboxylic acid (1h), i.e., a carboxylic acid halide, is reacted with Compound (10); etc.

The mixed acid anhydride used in the mixed acid anhydride method (A) can be obtained by the known Schotten-Baumann reaction, and the obtained mixed acid anhydride is reacted with Compound (10), usually without being isolated, to thereby produce the Compound (1i). The Schotten-Baumann reaction is performed in the presence of a basic compound. Usable basic compounds include compounds conventionally used in the Schotten-Baumann reaction, such as triethylamine, trimethylamine, pyridine, dimethylaniline, N-ethyldiisopropylamine, dimethylaminopyridine, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO) and other organic bases; sodium carbonate, potassium carbonate, sodium hydrogencarbonate, potassium hydrogencarbonate and other carbonates; sodium hydroxide, potassium hydroxide, calcium hydroxide and other metal hydroxides; potassium hydride, sodium hydride, potassium, sodium, sodium amide, metal alkoxides such as sodium methoxide and sodium ethoxide, and other inorganic bases; etc. The reaction is usually performed at about −20 to about 100° C., and preferably at about 0 to about 50° C., usually for about 5 minutes to about 10 hours, and preferably for about 5 minutes to about 2 hours. The reaction of the obtained mixed acid anhydride with Compound (10) is usually carried out at about −20 to about 150° C., and preferably at about 10 to about 50° C., usually for about 5 minutes to about 10 hours, and preferably for about 5 minutes to about 5 hours. Generally, the mixed acid anhydride method is performed in a solvent. Solvents used for conventional mixed acid anhydride methods are usable. Examples of usable solvents include chloroform, dichloromethane, dichloroethane, carbon tetrachloride and other halogenated hydrocarbons; benzene, toluene, xylene and other aromatic hydrocarbons; diethyl ether, diisopropyl ether, tetrahydrofuran, dimethoxyethane and other ethers; methyl acetate, ethyl acetate, isopropyl acetate and other esters; N,N-dimethylacetamide, N,N-dimethylformamide, dimethylsulfoxide, hexamethylphosphoric triamide and other aprotic polar solvents; mixtures thereof; etc. Examples of alkyl halocarboxylates usable in the mixed acid anhydride method include methyl chloroformate, methyl bromoformate, ethyl chloroformate, ethyl bromoformate, isobutyl chloroformate, etc. In this method, Compound (1h), an alkyl halocarboxylate and Compound (10) are preferably used in equimolar amounts, but each of the alkyl halocarboxylate and Compound (1h) can also be used in an amount of about 1 to about 1.5 mol per mol of Compound (10).

Method (C), in which a condensation reaction is carried out in the presence of an activating agent, can be performed in a suitable solvent in the presence or absence of a basic compound. Solvents and basic compounds usable in this method include those mentioned hereinafter as solvents and basic compounds usable in the method in which a carboxylic acid halide is reacted with Compound (10) mentioned above as one of the other methods (D). A suitable amount of activating agent is at least 1 mol, and preferably 1 to 5 mol per mol of Compound (10). When using WSC as an activating agent, addition of 1-hydroxybenzotriazol to the reaction system enables the reaction to proceed advantageously. The reaction is usually performed at about −20 to about 180° C., and preferably at about 0 to about 150° C., and is usually completed in about 5 minutes to about 90 hours.

When the method in which a carboxylic acid halide is reacted with Compound (10), mentioned above as one of the other methods (D), is employed, the reaction is performed in the presence of a basic compound in a suitable solvent. Usable basic compounds include a wide variety of known basic compounds, such as those for use in the Schotten-Baumann reaction described above. Usable solvents include, in addition to those usable in the mixed acid anhydride method, methanol, ethanol, isopropanol, propanol, butanol, 3-methoxy-1-butanol, ethylcellosolve, methylcellosolve and other alcohols; acetonitrile; pyridine; acetone; water; etc. The ratio of the carboxylic acid halide to Compound (10) is not limited and can be suitably selected from a wide range. It is usually suitable to use, for example, at least about 1 mol, and preferably about 1 to about 5 mol of the carboxylic acid halide per mol of Compound (10). The reaction is usually performed at about −20 to about 180° C., and preferably at about 0 to about 150° C., and usually completed in about 5 minutes to about 50 hours.

The amide bond formation reaction in Process 12 can also be performed by reacting Compound (1 h) with Compound (10) in the presence of a phosphorus compound serving as a condensing agent, such as triphenylphosphine, diphenylphosphinyl chloride, phenyl-N-phenylphosphoramide chloridate, diethyl chlorophosphate, diethyl cyanophosphate, diphenylphosphoric azide, bis(2-oxo-3-oxazolidinyl)phosphinic chloride or the like.

The reaction is carried out in the presence of a solvent and a basic compound usable for the method in which a carboxylic acid halide is reacted with Compound (10), usually at about −20 to about 150° C., and preferably at about 0 to about 100° C., and is usually completed in about 5 minutes to about 30 hours. It is suitable to use each of the condensing agent and Compound (1h) in amounts of at least about 1 mol, and preferably about 1 to about 2 mol per mol of Compound (10).

<Process 13>

In Process 13, the carboxylic acid moiety of Compound (1h) is subjected to an ester bond formation reaction with the compound of Formula (11) (hereinafter referred to as "Compound (11)") to produce the compound of Formula (1j) (hereinafter referred to as "Compound 1j").

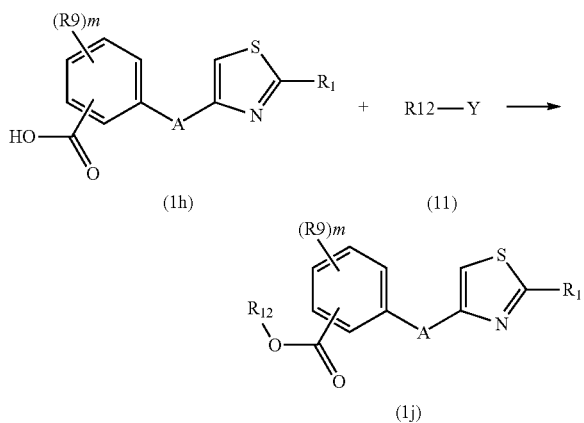

wherein R1, R9, A and m are as defined above; R12 is a $C_{1-6}$ alkyl group; and Y is a hydroxy group or a halogen atom.

Conditions for known ester bond formation reactions can be employed. For example, when Y in Compound (11) is a hydroxy group, the ester bond formation reaction can be performed by heating Compound (1h) and Compound (11) in a suitable solvent in the presence of acid. Examples of usable solvents include chloroform, dichloromethane, dichloroethane, carbon tetrachloride and other halogenated hydrocarbons; benzene, toluene, xylene and other aromatic hydrocarbons; diethyl ether, diisopropyl ether, tetrahydrofuran, dioxane, dimethoxyethane and other ethers; methyl acetate, ethyl acetate, isopropyl acetate and other esters; N,N-dimethylacetamide, N,N-dimethylformamide, dimethylsulfoxide, hexamethylphosphoric triamide and other aprotic polar solvents; mixtures thereof; etc. Compound (11) can also be used as a solvent. Examples of usable acids include trifluoroacetic acid and other organic acids; hydrochloric acid, bromic acid, hydrobromic acid, sulfuric acid and other inorganic acids; etc. The reaction is usually performed at about 0 to about 150° C., and preferably at about room temperature to about 100° C., and is usually completed in about 0.5 to about 30 hours.

When Y in Compound (11) is a halogen atom, the reaction in Process 13 is performed by reacting Compound (11) with Compound (1h) in a suitable solvent in the presence of a basic compound. Examples of usable solvents include methanol, ethanol, isopropanol, butanol, tert-butanol, ethylene glycol, diethylene glycol and other lower alcohols; chloroform, dichloromethane, dichloroethane, carbon tetrachloride and other halogenated hydrocarbons; benzene, toluene, xylene and other aromatic hydrocarbons; diethyl ether, diisopropyl ether, tetrahydrofuran, dioxane, dimethoxyethane and other ethers; methyl acetate, ethyl acetate, isopropyl acetate and other esters; N,N-dimethylacetamide, N,N-dimethylformamide, dimethylsulfoxide, hexamethylphosphoric triamide and other aprotic polar solvents; mixtures thereof; etc.

Examples of usable basic compounds include triethylamine, trimethylamine, pyridine, dimethylaniline, N-ethyldiisopropylamine, dimethylaminopyridine, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO) and other organic bases; sodium carbonate, potassium carbonate, sodium hydrogencarbonate, potassium hydrogencarbonate and other carbonates; sodium hydroxide, potassium hydroxide, calcium hydroxide and other metal hydroxides; potassium hydride, sodium hydride, potassium, sodium, sodium amide, metal alkoxides such as sodium methoxide and sodium ethoxide, and other inorganic bases; etc. A suitable ratio of Compound (1h) to Compound (11) is at least 1 mol, and preferably 1 to 5 mol of Compound (1h) per mol of Compound (11). The reaction is usually performed at about 0 to about −150° C., and preferably at about room temperature to about 100° C., and is usually completed in about 0.5 hours to about 30 hours.

<Process 14>

In Process 14, the compound of Formula (1k) (hereinafter referred to as "Compound (1k)") is alkylated with the compound of Formula (12) (hereinafter referred to as "Compound (12)") to produce the compound of Formula (1l) (hereinafter referred to as "Compound 1l").

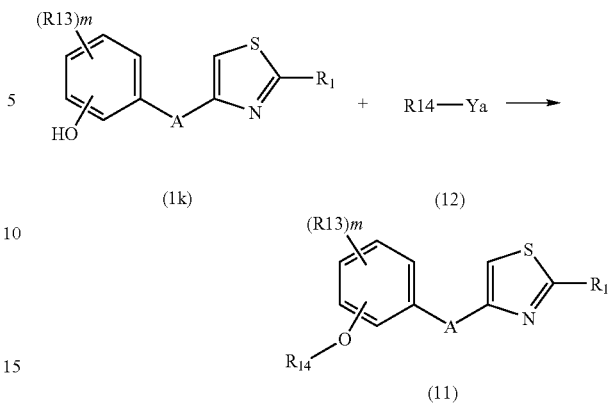

wherein R1, A and m are as defined above; R13 is a halogen atom, an unsubstituted or halogen-substituted $C_{1-6}$ alkyl group, an unsubstituted or halogen-substituted $C_{1-6}$ alkoxy group, a $C_{1-6}$ alkoxy-$C_{1-6}$ alkoxy group, a phenyl-$C_{1-6}$ alkoxy group, an amino-$C_{1-6}$ alkoxy group which may be substituted with a $C_{1-6}$ alkyl group, a methylenedioxy group, a carboxyl group, a phenoxy group, a $C_{1-6}$ alkoxycarbonyl group, a $C_{1-6}$ alkanoyloxy group, $C_{1-6}$ alkanoyl group, a cyano group, a nitro group, a $C_{1-6}$ alkylcarbamoyl group, an aminosulfonyl group, an amino group which may be substituted with a $C_{1-6}$ alkyl group or groups, a $C_{1-6}$ alkanoylamino group, a $C_{1-6}$ alkylthio group, a phenyl group, a pyrazolyl group, an imidazolyl group, a triazolyl group, a morpholino group, a pyrrolidinyl group, or a piperazinylcarbonyl group which may be substituted with a $C_{1-6}$ alkyl group or groups; R12 is a $C_{1-6}$ alkyl group; Y is a hydroxy group, a halogen atom or —$OSO_2$—R13; R13 is a $C_{1-6}$ alkyl group or a phenyl group in which the phenyl ring may be substituted with a $C_{1-6}$ alkyl group or groups, a halogen atom or atoms or a nitro group or groups; R14 is a $C_{1-6}$ alkyl group or a $C_{1-6}$ alkoxy-$C_{1-6}$ alkoxy group; and Ya is a halogen atom.

In Process 14, the alkylation reaction can be performed by reacting Compound (1k) with Compound (12), for example, in a suitable solvent in the presence of a basic compound. Examples of usable solvents include methanol, ethanol, isopropanol, butanol, tert-butanol, ethylene glycol, diethylene glycol and other lower alcohols; chloroform, dichloromethane, dichloroethane, carbon tetrachloride and other halogenated hydrocarbons; benzene, toluene, xylene and other aromatic hydrocarbons; diethyl ether, diisopropyl ether, tetrahydrofuran, dioxane, dimethoxyethane and other ethers; methyl acetate, ethyl acetate, isopropyl acetate and other esters; N,N-dimethylacetamide, N,N-dimethylformamide, dimethylsulfoxide, hexamethylphosphoric triamide and other aprotic polar solvents; mixtures thereof; etc.

Examples of basic compounds include triethylamine, trimethylamine, pyridine, dimethylaniline, N-ethyldiisopropylamine, dimethylaminopyridine, N-methylmorpholine, 1,5-diazabicyclo[4.3.0]nonene-5 (DBN), 1,8-diazabicyclo[5.4.0]-undecene-7 (DBU), 1,4-diazabicyclo[2.2.2]octane (DABCO) and other organic bases; sodium carbonate, potassium carbonate, sodium hydrogencarbonate, potassium hydrogencarbonate and other carbonates; metal hydroxides such as sodium hydroxide, potassium hydroxide and calcium hydroxide; potassium hydride, sodium hydride, potassium, sodium, sodium amide, metal alkoxides such as sodium methoxide and sodium ethoxide, and other inorganic bases; etc. A suitable ratio of Compound (12) to Compound (1k) is at least 1 mol, and preferably 1 to 5 mol of Compound (12) per mol of Compound (1k). The reaction is usually performed at about 0 to about 150° C., and preferably at about room temperature to about 100° C., and is usually completed in about 0.5 to about 30 hours.

(III) Production Process for Compound of Formula (2)

The compound of Formula (2) (hereinafter referred to as "Compound (2)") for use as a starting material can be produced by, for example, the following Process 15 or 16.

<Process 15>

In Process 15, the compound represented by Formula (13) (hereinafter referred to as "Compound (13)") is halogenated to produce Compound (2).

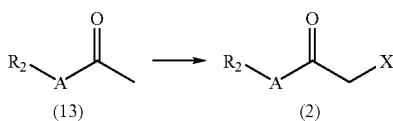

wherein R2, A and X are as defined above. The halogenation reaction of Compound (13) can be performed in a suitable solvent in the presence of a halogenating agent. Examples of usable halogenating agents include bromine, chlorine and other molecular halogens; iodine chloride; sulfuryl chloride; cupric bromide and other copper compounds; N-bromosuccinimide, N-chlorosuccinimide and other N-halogenated succinimides; etc. Examples of usable solvents include dichloromethane, dichloroethane, chloroform, carbon tetrachloride and other halogenated hydrocarbons; acetic acid; propionic acid and other fatty acids; carbon disulfide; etc. A suitable amount of halogenating agent is usually about 1 to about 10 mol, and preferably about 1 to about 5 mol per mol of Compound (13). The reaction is usually performed at about 0° C. to about the boiling point of the solvent, and preferably at about 0 to about 100° C., and is usually completed in about 5 minutes to about 20 hours.

<Process 16>

In Process 16, the compound represented by Formula (14) (hereinafter referred to as "Compound (14)") is halogenated in the presence of water under acidic conditions to produce Compound (2).

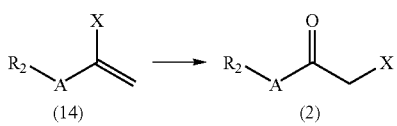

wherein R2, A and X are as defined above. The halogenation reaction of Compound (14) is performed in a suitable solvent in the presence of a halogenating agent. Examples of usable halogenating agents include bromine, chlorine and other molecular halogens; iodine chloride; sulfuryl chloride; N-bromosuccinimide, N-chlorosuccinimide and other N-halogenated succinimides; etc. Examples of usable solvents include hydrous acetonitrile. Examples of usable acids include hydrochloric acid, bromic acid, hydrobromic acid, sulfuric acid and other inorganic acids, and the like. A suitable amount of the halogenating agent is usually about 1 to about 10 mol, and preferably about 1 to about 5 mol per mol of Compound (14). The reaction is usually performed at 0° C. to the boiling temperature of the solvent, and preferably at about 0 to about 100° C., and is usually completed in about 5 minutes to about 20 hours.

(IV) Medicinal Effects and Uses

The compounds represented by Formula (1), optical isomers thereof and salts thereof (hereinafter collectively referred to as "the compound of the present invention") exhibit specific inhibitory activity against PDE4, and thus are useful as active ingredients of PDE4 inhibitors.

The compound of the present invention, based on its specific inhibitory activity against PDE4, can be used as an active ingredient of a pharmaceutical composition for use as a preventive or therapeutic agent for various diseases. Examples of diseases on which preventive or therapeutic effects are exhibited based on the specific inhibitory activity against PDE4 include acute or chronic (in particular, inflammatory and allergen-induced) respiratory tract diseases (e.g., bronchial asthma and chronic obstructive pulmonary diseases) of various origins; dermatoses (in particular, proliferative, inflammatory and allergic types) (e.g., psoriasis vulgaris, toxic and allergic contact eczemas, atopic dermatitis, alopecia greata and other proliferative, inflammatory and allergic dermatoses); diseases related to nervous dysfunctions, such as of learning, memory and cognition disorders, caused due to Alzheimer's disease, Parkinson's disease, etc.; diseases related to mental dysfunctions (e.g., manic-depressive psychosis, schizophrenia and anxiety syndrome); systemic or local joint diseases (e.g., knee osteoarthrosis and articular rheumatism); diffuse inflammation in the gastrointestinal region (e.g., Crohn's disease and ulcerative colitis); allergic and/or chronic diseases in the upper respiratory tract (pharyngeal cavity, nose) region and adjacent regions (paranasal sinus, eye) caused by improper immunological reactions (e.g., allergic rhinitis/sinusitis, chronic rhinitis/sinusitis and allergic conjunctivitis); and other diseases. Among these, for atopic dermatitis, the compound of the present invention exhibits particularly high preventive or therapeutic effects, and therefore can be suitably applied to prevent or treat this disease.

When the compound of the present invention is employed as a PDE 4 inhibitor or a preventive or therapeutic agent for diseases as mentioned above, the compound can be used as an oral preparation, an injection, an external preparation or like preparation.

When used as an oral preparation, the compound can be formulated into a powder, tablets, granules, capsules, a syrup, films, troches, a liquid or like forms. The oral preparation may contain a pharmaceutically acceptable base and/or carrier, and pharmaceutically acceptable additives, such as binders, disintegrators, lubricants, humectants, buffers, preservatives, flavors, etc., as required.

When used as an injection, the compound can be formulated into an aqueous solution or suspension obtained by dissolving or suspending the compound in physiological saline, an aqueous glucose solution or the like.

When used as an external preparation, the compound can be formulated into a liquid, oily preparation, lotion, liniment, milky lotion, suspension, cream, ointment or like forms. The external preparation may contain a carrier, a base and/or additives that are conventionally used in external preparations, as required. Examples of usable additives include water, oils, surfactants, solubilizing components, emulsifiers, colorants (dyes, pigments), flavors, preservatives, antiseptics, thickeners, antioxidants, sequestering agents, pH modifiers, deodorizers, etc.

When the compound of the present invention is employed as a PDE4 inhibitor or a preventive or therapeutic agent for the above diseases, the effective dosage amount and number of doses of the compound of the present invention vary depending on the type of the compound, the age and weight of the subject to be given the compound, the symptom, the purpose of use and other factors, and cannot generally be defined. For example, for an adult per day, an amount corresponding 0.1 to 1000 mg of the compound of the present invention can be administered or applied in a single dose or in two or more divided doses.

Another aspect of the present invention provides a method for treating the above-mentioned diseases, the method comprising the step of administering an effective amount of the compound of the present invention to a human or non-human mammal.

Further, the compound of the present invention has TNF-α production inhibitory activity and IL-4 production inhibitory activity, and thus is useful as an active ingredient in a TNF-α production inhibitor or an IL-4 production inhibitor. The form, route of administration, dosage amount and the like of a TNF-α production inhibitor or an IL-4 production inhibitor comprising the compound of the present invention are the same as those of the above-mentioned PDE4 inhibitor and preventive or therapeutic agent.

EXAMPLES

The following Examples are given to illustrate the present invention, and are not intended to limit the scope of the invention.

Reference Example 1

Production of ethyl 2-benzoyl-4-bromo-4-pentenoate

Sodium hydride (0.26 g, 6.0 mmol) was added under ice cooling to a solution (10 ml) of ethyl benzoylacetate (1.0 ml, 5.77 mmol) in DMF, followed by stirring for 30 minutes, and then 2,3-dibromopropene (0.63 ml, 5.77 mmol) was added. The resulting mixture was stirred at room temperature for 1.5 hours, water was added to the reaction mixture, and extraction with ethyl acetate was performed three times. The organic layer was dried over anhydrous sodium sulfate, the solvent was distilled off under reduced pressure, and the residue was purified by silica gel column chromatography (eluent: n-hexane/ethyl acetate=4/1). The solvent was distilled off under reduced pressure, to thereby obtain 1.55 g (yield: 86%) of ethyl 2-benzoyl-4-bromo-4-pentenoate as a colorless oil.

NMR δ ppm (CDCl3); 8.06-8.04 (2H, m), 7.63-7.60 (1H, m), 7.52-7.49 (2H, m), 5.71 (1H, d, J=1.8 Hz), 5.46 (1H, d, J=1.8 Hz), 4.81-4.79 (2H, m), 4.16 (2H, q, J=7.1 Hz), 3.15-3.11 (2H, m), 1.18 (3H, t, J=7.1 Hz)

Reference Example 2

Production of ethyl 2-benzoyl-5-bromo-4-oxopentanoate

N-bromosuccinimide (0.95 g, 5.3 mmol) and a drop of hydrobromic acid were added to a solution of ethyl 2-benzoyl-4-bromo-4-pentenoate (1.5 g, 4.82 mmol) in acetonitrile (16 ml) and water (4 ml), followed by stirring at room temperature for 3 hours and 40 minutes. The reaction mixture was diluted with diethyl ether, and a 5% aqueous sodium thiosulfate solution was added to separate the mixture into layers. The organic layer was washed twice with a saturated aqueous sodium hydrogencarbonate solution, washed with a saturated salt solution, and dried over anhydrous sodium sulfate. The solvent was distilled off under reduced pressure, and the residue was purified by silica gel column chromatography (eluent: n-hexane/ethyl acetate=4/1). The solvent was distilled off under reduced pressure, to thereby obtain 0.91 g (yield: 58%) of ethyl 2-benzoyl-5-bromo-4-oxopentenoate as a colorless oil.

NMR δ ppm (CDCl3); 8.03-8.01 (2H, m), 7.63-7.59 (1H, m), 7.51-7.48 (2H, m), 4.93 (1H, dd, J=6.4 Hz, 7.5 Hz), 4.15 (2H, q, J=7.1 Hz), 4.05 (2H, dd, J=13.0 Hz, 21.7 Hz), 3.43 (1H, dd, J=7.5 Hz, 18.1 Hz), 3.36 (1H, dd, J=6.4 Hz, 18.1 Hz), 1.16 (3H, t, J=7.1 Hz)

Reference Example 3

Production of 4-chloromethyl-2-(3,4-diethoxyphenyl)thiazole 3,4-diethoxythiobenzamide (30.0 g, 133 mmol) was suspended in ethanol (300 ml), and 1,3-dichloroacetone (12.8 ml, 135 mmol) was added, followed by heating under reflux for 4 hours. After cooling to room temperature, the solvent was distilled off under reduced pressure, and the residue was subjected to extraction with ethyl acetate. The organic layer was washed with a saturated aqueous sodium hydrogencarbonate solution, and dried over anhydrous sodium sulfate. The solvent was distilled off under reduced pressure, and the residue was purified by silica gel column chromatography (eluent: ethyl acetate/n-hexane=1/3). The solvent was distilled off under reduced pressure, and the residue was recrystallized from an ethyl acetate/n-hexane mixed solvent, to thereby obtain 26.9 g (yield: 68%) of 4-chloromethyl-2-(3,4-diethoxyphenyl)thiazole as yellow prisms.

Melting point: 81.5-82.3° C.

Reference Example 4

Production of 2-(3,4-diethoxyphenyl)thiazole-4-carboxaldehyde

N-methylmorpholine-N-oxide (16.5 g, 141 mmol) was added to a solution (200 ml) of 4-chloromethyl-2-(3,4-diethoxyphenyl)thiazole (13.99 g, 47 mmol) in acetonitrile, followed by heating under reflux for 1.5 hours. After cooling to room temperature, the solvent was distilled off under reduced pressure, and the residue was subjected to extraction with ethyl acetate. The organic layer was washed with a saturated salt solution, and dried over anhydrous sodium sulfate. The solvent was distilled off under reduced pressure, and the residue was purified by silica gel column chromatography (eluent: ethyl acetate/n-hexane=1/2). The solvent was distilled off under reduced pressure, to thereby obtain 11.2 g (yield: 86%) of 2-(3,4-diethoxyphenyl)thiazole-4-carboxaldehyde as a yellow solid.

Melting point: 84.0-87.0° C.

Reference Example 5

Production of 3-[2-(3,4-diethoxyphenyl)thiazole-4-yl]propionic acid

Bromine (55 ml, 1.07 mol) was added dropwise under ice cooling to a solution (1.2 l) of dimethyl acetyl succinate (200 g, 1.06 mol) in diethyl ether. The resulting mixture was stirred at room temperature overnight, and the solvent was distilled off under reduced pressure. Acetic acid (0.4 l) and concentrated hydrochloric acid (0.4 l) were added to the residue, and the resulting mixture was stirred at room temperature for 4.5 hours and further at 80° C. for 3.5 hours. The solvent was distilled off under reduced pressure, and 3,4-diethoxythiobenzamide (215.5 g, 0.96 mol), dimethoxyethane (0.8 l) and water (0.4 l) were added to the residue, followed by stirring at 80° C. for 1 hour. After cooling to room temperature, the precipitated crystals were collected by filtration, washed with water, and dried at 60° C. to thereby obtain 305.15 g (yield: 83%) of 3-[2-(3,4-diethoxyphenyl)thiazole-4-yl]propionic acid as a light brown powder.

Melting point: 111.3-113.5° C.

Reference Example 6

Production of methyl 3-[2-(3,4-diethoxyphenyl)thiazole-4-yl]propionate

A solution (2.3 l) of 3-[2-(3,4-diethoxyphenyl)thiazole-4-yl]propionic acid (254.5 g) in methanol was ice-cooled, and 58 ml of thionyl chloride was added dropwise. After completion of the addition, the resulting mixture was heated under reflux for 2 hours and cooled to room temperature. The solvent was distilled off under reduced pressure, and the residue was subjected to extraction with ethyl acetate. The organic layer was washed with a saturated aqueous sodium hydrogencarbonate solution, and dried over anhydrous sodium sulfate. The solvent was distilled off under reduced pressure, and the residue was purified by silica gel column chromatography (eluent: ethyl acetate/n-hexane=1/3). The solvent was distilled off under reduced pressure, and the residue was recrystallized from an ethyl acetate/n-hexane mixed solvent, to thereby obtain 219.35 g (yield: 68%) of methyl 3-[2-(3,4-diethoxyphenyl)thiazole-4-yl]propionate as a white powder.

Melting point; 58.1-58.3° C.

Reference Example 7

Production of 3-[2-(3,4-diethoxyphenyl)]thiazole-4-yl]-N-methoxy-N-methylpropionamide 1-hydroxybenzotriazole (22.91 g, 149.6 mmol), 1-(3-dimethylaminopropyl)-3-ethylcarbodiimide hydrochloride (WSC) (28.68 g, 149.6 mmol), N,O-dimethylhydroxylamine hydrochloride (13.93 g, 136 mmol) and triethylamine (41.7 ml, 299.2 mmol) were added to a solution (1.0 l) of 3-[2-(3,4-diethoxyphenyl)thiazole-4-yl]propionic acid (43.71 g, 136 mmol) in dichloromethane, followed by stirring at room temperature for 4 hours. Water was added to separate the reaction mixture into layers, and the aqueous layer was further subjected to extraction with dichloromethane. The organic layer was dried over anhydrous sodium sulfate. The solvent was distilled off under reduced pressure, and the residue was purified by silica gel column chromatography (eluent: ethyl acetate/n-hexane=1/3). The solvent was distilled off under reduced pressure, and the residue was recrystallized from an ethyl acetate/n-hexane mixed solvent, to thereby obtain 42.4 g (yield: 68%) of 3-[2-(3,4-diethoxyphenyl)thiazole-4-yl]-N-methoxy-N-methylpropionamide as colorless prisms.

Melting point: 72.0-73.0° C.

Example 1

Production of (E)-3-[2-(3,4-diethoxyphenyl)thiazole-4-yl]-1-(2-methoxyphenyl)propenone 2-methoxyacetophenone (0.16 ml, 1.2 mmol) was added to a solution (5 ml) of 2-(3,4-diethoxyphenyl)thiazole-4-carboxaldehyde (310.5 mg, 1.12 mmol) in ethanol at room temperature. A 1M aqueous potassium hydroxide solution (2.24 ml, 2.24 mmol) was then added dropwise at the same temperature. After stirring at room temperature for 1 hour, water was added to the reaction mixture, followed by extraction with dichloromethane. The extract was dried over anhydrous sodium sulfate, and the solvent was distilled off under reduced pressure. The residue was recrystallized from ethyl acetate/n-hexane, to thereby obtain 400 mg (yield: 94%) of (E)-3-[2-(3,4-diethoxyphenyl)thiazole-4-yl]-1-(2-methoxyphenyl)propenone as a yellow powder.

Melting point: 130-131° C.

Example 2

Production of (E)-3-[2-(3,4-diethoxyphenyl)thiazole-4-yl]-1-(2-methoxyphenyl)propenone Sodium hydride (353.3 mg, 8.83 mmol) was added to a solution (80 ml) of diethyl [2-(2-methoxyphenyl)-2-oxoethyl]phosphonate (2.30 g, 8.03 mmol) in THF at room temperature. After stirring at the same temperature for 30 minutes, 2-(3,4-diethoxyphenyl)thiazole-4-carboxaldehyde (2.15 g, 7.75 mmol) was added, and the resulting mixture was stirred at room temperature for 22 hours. The solvent was distilled off under reduced pressure, and the residue was purified by silica gel column chromatography (eluent: n-hexane/ethyl acetate=3/1 to 2/1). The solvent was distilled off under reduced pressure, and the residue was recrystallized from ethyl acetate/n-hexane, to thereby obtain 1.62 g (yield: 51%) of (E)-3-[2-(3,4-diethoxyphenyl)thiazole-4-yl]-1-(2-methoxyphenyl)propenone as yellow prisms.

Melting point: 130-131° C.

Example 3

Production of (E)-3-[2-(3,4-dimethoxyphenyl)thiazole-4-yl]-1-(3,4-diacetoxyphenyl)propenone 2-(3,4-dimethoxyphenyl)thiazole-4-carboxaldehyde (450 mg, 1.81 mmol) and 3,4-diacetoxybenzoyl methylenetriphenylphosphorane (900 mg, 1.81 mmol) were suspended in THF (25 ml), and the suspension was heated under reflux for 20 hours. After cooling, the solvent was distilled off under reduced pressure, and the residue was purified by silica gel column chromatography (eluent: dichloromethane). The solvent was distilled off under reduced pressure, and the residue was recrystallized from ethyl acetate/n-hexane, to thereby obtain 380 mg (yield: 44.9%) of (E)-3-[2-(3,4-dimethoxyphenyl)thiazole-4-yl]-1-(3,4-diacetoxyphenyl)propenone as a yellow powder.

Melting point: 163-164° C.

Examples 4 to 34

According to the production process of Example 1, the following compounds of Examples 4 to 34 were produced (Table 1). Table 1 also shows the melting points of these compounds.

TABLE 1

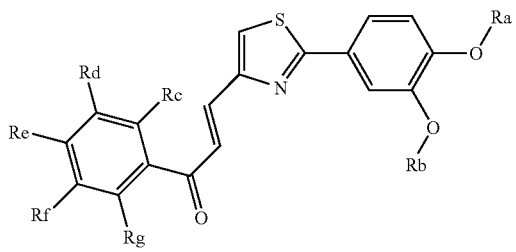

| Examples | Ra | Rb | Rc | Rd | Re | Rf | Rg | Melting point (° C.) | Salt |
|---|---|---|---|---|---|---|---|---|---|
| 4 | —C$_2$H$_5$ | —C$_2$H$_5$ | —OCH$_2$OCH$_3$ | —H | —OCH$_2$OCH$_3$ | —H | —OH | 140.3-143 | — |
| 5 | —C$_2$H$_5$ | —C$_2$H$_5$ | —H | —H | —OCH$_2$OCH$_3$ | —OCH$_2$OCH$_3$ | —H | 89.8-91.5 | — |
| 6 | —CH$_3$ | —CH$_3$ | —H | —OH | —H | —OH | —H | 164-168 (degrade) | hydrochloride |
| 7 | —CH$_3$ | —CH$_3$ | —H | —OH | —OH | —H | —H | 162-165 | hydrochloride |
| 8 | —C$_2$H$_5$ | —C$_2$H$_5$ | —H | —H | —OCOCH$_3$ | —OCOCH$_3$ | —H | 139-140 | — |
| 9 | —C$_2$H$_5$ | —C$_2$H$_5$ | —OH | —H | —OH | —H | —OH | 188-189 | — |
| 10 | —C$_2$H$_5$ | —C$_2$H$_5$ | —H | —H | —OH | —H | —H | 133-134 | — |
| 11 | —C$_2$H$_5$ | —C$_2$H$_5$ | —H | —OCH$_3$ | —OCH$_3$ | —OCH$_3$ | —H | 155-156 | — |
| 12 | —C$_2$H$_5$ | —C$_2$H$_5$ | —H | —Cl | —NH$_2$ | —Cl | —H | 165-168 | hydrochloride |
| 13 | —C$_2$H$_5$ | —C$_2$H$_5$ | —H | —H | —OCH$_3$ | —OCH$_3$ | —H | 152-153 | — |
| 14 | —C$_2$H$_5$ | —C$_2$H$_5$ | —H | —H | —H | —H | —H | 129-130 | — |
| 15 | —C$_2$H$_5$ | —C$_2$H$_5$ | —OH | —H | —H | —H | —H | 126-127 | hydrobromide |
| 16 | —C$_2$H$_5$ | —C$_2$H$_5$ | —H | —H | —H | —OH | —H | 144.5-146 | — |
| 17 | —C$_2$H$_5$ | —C$_2$H$_5$ | —H | —H | —CO$_2$CH$_3$ | —H | —H | 150-151 | — |
| 18 | —C$_2$H$_5$ | —C$_2$H$_5$ | —H | —H | —CN | —H | —H | 164-167 | — |
| 19 | —C$_2$H$_5$ | —C$_2$H$_5$ | —H | —H | —OH | —CO$_2$H | —H | 195-196 | — |
| 20 | —C$_2$H$_5$ | —C$_2$H$_5$ | —H | —H | —OH | —CO$_2$CH$_3$ | —H | 161.3-162.8 | — |
| 21 | —C$_2$H$_5$ | —C$_2$H$_5$ | —H | —H | —Cl | —H | —H | 131-133 | — |
| 22 | —CH$_3$ | —CH$_3$ | —H | —C(CH$_3$)$_3$ | —OH | —C(CH$_3$)$_3$ | —H | 228-230 | — |
| 23 | —C$_2$H$_5$ | —C$_2$H$_5$ | —H | —H | —COCH$_3$ | —H | —H | 128-129 | — |
| 24 | —C$_2$H$_5$ | —C$_2$H$_5$ | —H | —H | —H | —NO$_2$ | —H | 125-126 | — |
| 25 | —C$_2$H$_5$ | —C$_2$H$_5$ | —H | —H | —F | —H | —H | 116-121 | — |
| 26 | —C$_2$H$_5$ | —C$_2$H$_5$ | —H | —H | —CH$_3$ | —H | —H | 124-125.5 | — |
| 27 | —C$_2$H$_5$ | —C$_2$H$_5$ | —H | —H | —H | —H | —NO$_2$ | 142-143 | — |
| 28 | —C$_2$H$_5$ | —C$_2$H$_5$ | —H | —H | —NHCOCH$_3$ | —H | —H | 199.5-201.5 | — |
| 29 | —C$_2$H$_5$ | —C$_2$H$_5$ | —H | —H | —Cl | —Cl | —H | 138-139 | — |
| 30 | —C$_2$H$_5$ | —C$_2$H$_5$ | —H | —H | —NH$_2$ | —H | —H | 148-150 | — |
| 31 | —C$_2$H$_5$ | —C$_2$H$_5$ | —H | —H | —OC$_2$H$_5$ | —H | —H | 130-135 | — |
| 32 | —C$_2$H$_5$ | —C$_2$H$_5$ | —H | —H | —NO$_2$ | —H | —H | 125-127 | — |
| 33 | —C$_2$H$_5$ | —C$_2$H$_5$ | —H | —H | —H | —H | —CO$_2$CH$_3$ | 132-133 | — |
| 34 | —C$_2$H$_5$ | —C$_2$H$_5$ | —H | —H | —CON(CH$_3$)$_2$ | —H | —H | 110-112 | — |

Examples 35 to 36

According to the production process of Example 1, the following compounds of Examples 35 and 36 were produced (Table 2). Table 2 also shows physicochemical characteristics of these compounds.

TABLE 2

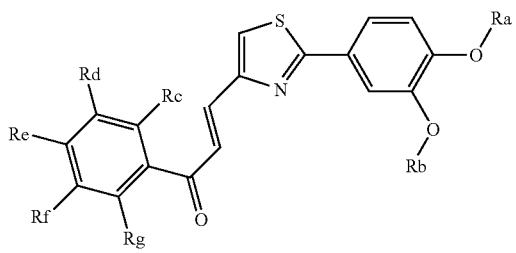

| Examples | Ra | Rb | Rc | Rd | Re | Rf | Rg | NMR δ ppm(CDCl$_3$) |
|---|---|---|---|---|---|---|---|---|
| 35 | —C$_2$H$_5$ | —C$_2$H$_5$ | —OCH$_2$OCH$_3$ | —H | —OCH$_2$OCH$_3$ | —H | —OCH$_2$OCH$_3$ | 7.58(1 H, d, 2.0 Hz), 7.47(1 H, dd, J = 2.0, 8.4 Hz), 7.35-7.33(3 H, m), 6.92(1 H, J = 8.4 Hz), 6.57(2 H, s), 5.19(2 H, s), 5.13(4 H, s), 4.21(2 H, |

TABLE 2-continued

| Examples | Ra | Rb | Rc | Rd | Re | Rf | Rg | NMR δ ppm(CDCl₃) |
|---|---|---|---|---|---|---|---|---|
| 36 | —CH₃ | —CH₃ | —H | —H | —OH | —CO₂CH₃ | —H | q, J = 7.0 Hz), 4.13(2 H, q, J = 7.0 Hz), 3.51(3 H, s), 3.41(6 H, s), 1.51(3 H, t, J = 7.0 Hz), 1.49(3 H, J = 7.0 Hz). 11.28(1 H, s), 8.67(1 H, d, J = 2.2 Hz), 8.28(1 H, dd, J = 2.4, 8.8 Hz), 8.00(1 H, d, J = 15.0 Hz), 7.79(1 H, d, J = 15.0 Hz), 7.61(1 H, d, J = 2.4 Hz), 7.59(1 H, dd, J = 2.2, 8.2 Hz), 7.49(1 H, s), 7.13(1 H, d, J = 8.8 Hz), 6.97(1 H, d, J = 8.2 Hz), 4.03(3 H, s), 4.02(3 H, s), 3.97(3 H, s) |

Examples 37 to 42

According to the production process of Example 1, the following compounds of Examples 37 to 42 were produced (Table 3). Table 3 also shows physicochemical characteristics of these compounds.

TABLE 3

| Examples | Ra | Rb | Rc | Rd | Re | Rf | Rg | Melting point (° C.) | Salt |
|---|---|---|---|---|---|---|---|---|---|
| 37 | —CH₃ | —CH₃ | —H | —H | —OH | —H | —H | 174-177 | — |
| 38 | —CH₃ | —CH₃ | —H | —H | —O(CH₂)₂N(C₂H₅)₂ | —H | —H | 178-183 | trihydrochloride |
| 39 | —CH₃ | —CH₃ | —H | —H | —OH | —CO₂H | —H | 227.4-228 | — |
| 40 | —CH₃ | —C₂H₅ | —OCH₃ | —H | —H | —OCH₃ | —H | 79-82 | — |
| 41 | —CH₃ | —CH₃ | —H | —H | N-methylpyrrolidinyl | —H | —H | 165-166 | — |
| 42 | —C₂H₅ | —C₂H₅ | —H | —H | 4-acetyl-N-methylpiperazinyl | —H | —H | 135 (degraded) | dihydrochloride |

Examples 43 to 57

According to the production process of Example 1, the following compounds of Examples 43 to 57 were produced (Table 4). Table 4 also shows physicochemical characteristics of these compounds.

TABLE 4

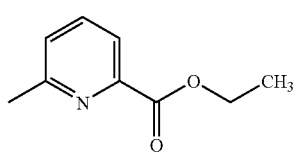

| Examples | Ra | Rb | Rh | Melting point (° C.) | Salt |
|---|---|---|---|---|---|
| 43 | —CH₃ | —CH₃ | -4-PYRIDYL | 167-168 | — |
| 44 | —CH₃ | —CH₃ | -3-PYRIDYL | 168-169 | — |
| 45 | —CH₃ | —CH₃ | -2-PYRIDYL | 137-139 | — |
| 46 | —CH₃ | —CH₃ | -2-FURYL | 154-156 | — |
| 47 | —CH₃ | —CH₃ | -2-THIENYL | 157-158 | — |
| 48 | —CH₃ | —CH₃ | -3-THIENYL | 178-179 | — |
| 49 | —C₂H₅ | —C₂H₅ | -2-PYRIDYL | 92.2-93.8 | — |
| 50 | —CH₃ | —CH₃ | 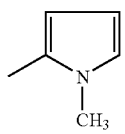 | 175-177 | — |
| 51 | —CH₃ | —CH₃ | 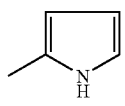 | 152-153 | — |
| 52 | —CH₃ | —CH₃ | 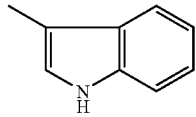 | 176-177 | — |
| 53 | —CH₃ | —CH₃ | 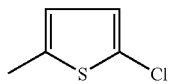 | 197-199 | — |
| 54 | —CH₃ | —CH₃ | 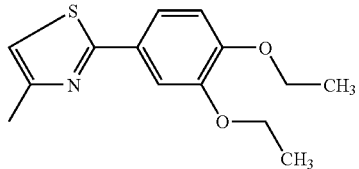 | 146-147 | — |
| 55 | —C₂H₅ | —C₂H₅ |  | 116-117 | — |

TABLE 4-continued

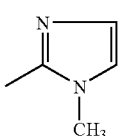

| Examples | Ra | Rb | Rh | Melting point (° C.) | Salt |
|---|---|---|---|---|---|
| 56 | —CH₃ | —CH₃ | 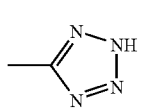 | 147-149 | dihydrochloride |
| 57 | —CH₃ | —CH₃ | | 222-224 (degraded) | — |

Example 58

Production of methyl 2-[2-(3,4-diethoxyphenyl)thiazole-4-ylmethyl]-3-(3-ethoxypyridine-2-yl)-3-oxopropionate Sodium hydride (239 mg, 6.0 mmol) and a drop of methanol were added to a solution (10 ml) of methyl 3-[2-(3,4-diethoxyphenyl)thiazole-4-yl]propionate (1.0 g, 3.0 mmol) and methyl 3-ethoxypyridine-2-carboxylate (702 mg, 3.9 mmol) in dimethoxyethane, followed by heating under reflux for 2 hours. After cooling to room temperature, a saturated aqueous ammonium chloride solution was added to the reaction mixture, and the resulting mixture was subjected to extraction with ethyl acetate. The organic layer was washed with a saturated salt solution, and dried over anhydrous magnesium sulfate. The solvent was distilled off under reduced pressure, and the residue was purified by silica gel column chromatography (eluent: ethyl acetate/n-hexane=2/3). The solvent was distilled off under reduced pressure, to thereby obtain 740 mg (yield: 51%) of methyl 2-[2-(3,4-diethoxyphenyl)thiazole-4-ylmethyl]-3-(3-ethoxypyridine-2-yl)-3-oxopropionate as a yellow oil.

HNMR δ ppm (CDCl3); 8.22 (1H, dd, J=1.3 Hz, 4.3 Hz), 7.44 (1H, d, J=2.1 Hz), 7.4-7.2 (3H, m), 6.92 (1H, s), 6.85 (1H, d, J=8.4 Hz), 5.29 (1H, t, J=7.4 Hz), 4.2-4.0 (6H, m), 3.65 (3H, s), 3.6-3.4 (2H, m), 1.5-1.4 (9H, m)

Example 59

Production of ethyl 2-[2-(3,4-diethoxyphenyl)thiazole-4-ylmethyl]-3-oxo-3-phenylpropionate 3,4-diethoxythiobenzamide (0.63 g, 2.8 mmol) was added to a solution (20 ml) of ethyl 2-benzoyl-5-bromo-4-oxopentanoate (0.90 g, 2.8 mmol) in ethanol, followed by heating under reflux for 1.5 hours. After cooling to room temperature, the solvent was distilled off under reduced pressure, and the residue was subjected to extraction with ethyl acetate. The organic layer was washed with a saturated aqueous sodium hydrogencarbonate solution and a saturated salt solution, and dried over anhydrous sodium sulfate. The solvent was distilled off under reduced pressure, to thereby obtain 1.43 g (yield: 65%) of ethyl 2-[2-(3,4-diethoxyphenyl)thiazole-4-ylmethyl]-3-oxo-3-phenylpropionate as a yellow oil.

NMR δ ppm (CDCl3); 8.06-8.05 (2H, m), 7.58-7.55 (1H, m), 7.47-7.44 (2H, m), 7.40 (1H, d, J=2.0 Hz), 7.36 (1H, dd, J=2.0 Hz, 8.4 Hz), 6.90 (1H, s), 6.86 (1H, d, J=8.4 Hz), 5.06-5.03 (1H, m), 4.17-4.07 (6H, m), 3.50-3.49 (2H, m), 1.47 (6H, t, J=7.0 Hz), 1.15 (3H, t, J=7.2 Hz)

Examples 60 to 66

According to the production process of Example 58, the following compounds of Examples 60 to 66 were produced (Table 5). Table 5 also shows physicochemical characteristics of these compounds.

TABLE 5

| Examples | Ra | Rb | Rc | Rd | Re | Rf | Rg | Ri | NMR δ ppm(CDCl₃) |
|---|---|---|---|---|---|---|---|---|---|
| 60 | —C₂H₅ | —C₂H₅ | —H | —H | —Cl | —H | —OCH₃ | —CH₃ | 7.71(1 H, d, J = 8.3 Hz), 7.41(1 H, d, J = 2.0 Hz), 7.35(1 H, dd, J = 2.0 Hz, 8.3 Hz), 6.98(1 H, dd, J = 1.8 Hz, 8.4 Hz), 6.92(1 H, d, J = 1.8 Hz), 6.9-6.8(2 H, m), 4.95(1 H, dd, J = 6.5 Hz, 7.8 Hz), 4.2-4.0(4 H, m), 3.85(3 H, s), 3.69(3 H, s), 3.6-3.3(2 H, m), 1.5-1.4(6 H, m) |
| 61 | —C₂H₅ | —C₂H₅ | —H | —H | —H | —Cl | —OCH₃ | —CH₃ | 7.5-7.3(4 H, m), 7.04(1 H, t, J = 7.9 Hz), 6.89(1 H, s), 6.85(1 H, d, J = 8.4 Hz), 5.09(1 H, dd, J = 6.6 Hz, 8.0 Hz), 4.2-4.0(4 H, m), 3.84(3 H, s), 3.70(3 H, s), 3.5-3.4(2 H, m), 1.5-1.4(6 H, m) |
| 62 | —C₂H₅ | —C₂H₅ | —H | —H | —H | —H | —OC₂H₅ | —C₂H₅ | 7.68(1 H, dd, J = 1.8 Hz, 7.7 Hz), 7.5-7.3(3 H, m), 7.0-6.8(4 H, m), 5.14(1 H, t, J = 7.3 Hz), 4.2-4.0(8 H, m), 3.6-3.3(2 H, m), 1.5-1.3(9 H, m), 1.13(3 H, t, J = 7.1 Hz) |
| 63 | —C₂H₅ | —C₂H₅ | —H | —H | —H | —H | —N(CH₃)₂ | —C(CH₃)₃ | 7.49(1 H, d, J = 1.9 Hz), 7.43-7.2(3 H, m), 7.0-6.8(4 H, m), 5.28(1 H, t, J = 7.1 Hz), 4.2-4.1(4 H, m), 3.36(2 H, dd, J = 2.2 Hz, 7.1 Hz), 2.69(6 H, s), 1.5-1.4(6 H, m), 1.27(9 H, s) |
| 64 | —C₂H₅ | —C₂H₅ | —H | —H | —H | —H | —OCH₂OCH₃ | —CH₃ | 7.69(1 H, dd, J = 7.8 Hz), 7.5-7.3(3 H, m), 7.19(1 H, d, J = 8.4 Hz), 7.1-7.0(1 H, m), 6.88(1 H, s), 6.85(1 H, d, J = 8.4 Hz), 5.22(2 H, s), 5.1-5.0(1 H, m), 4.2-4.0(4 H, m), 3.68(3 H, s), 3.6-3.3(5 H, m), 1.5-1.4(6 H, m) |
| 65 | —C₂H₅ | —C₂H₅ | —H | —H | —H | —H | —OC₆H₅ | —CH₃ | 7.80(1 H, dd, J = 1.8 Hz, 7.8 Hz), 7.4-7.2(5 H, m), 7.2-6.9(4 H, m), 6.9-6.8(3 H, m), 5.13(1 H, dd, J = 6.2 Hz, 8.3 Hz), 4.2-4.0(4 H, m), 3.7-3.3(5 H, m), 1.5-1.4(6 H, m) |
| 66 | —C₂H₅ | —C₂H₅ | —H | —H | —H | —H | —OCH₃ | —CH₃ | 7.74(1 H, dd, J = 1.8 Hz, 7.7 Hz), 7.5-7.4(2 H, m), 7.36(1 H, dd, J = 2.1 Hz, 8.3 Hz), 7.1-6.8(4 H, m), 4.97(1 H, t, J = 7.2 Hz), 4.2-4.0(4 H, m), 3.85(3 H, s), 3.69(3 H, s), 3.6-3.3(2 H, m), 1.5-1.4(6 H, m) |

Examples 67 to 71

According to the production process of Example 58, the following compounds of Examples 67 to 71 were produced (Table 6). Table 6 also shows physicochemical characteristics of these compounds.

TABLE 6

| Examples | Ra | Rb | Rc | Rd | Re | Rf | Rg | Ri | MS(M + 1) |
|---|---|---|---|---|---|---|---|---|---|
| 67 | —C₂H₅ | —C₂H₅ | —H | —H | —H | —H | —CN | —CH₃ | 465 |
| 68 | —C₂H₅ | —C₂H₅ | —H | —H | —H | —H | —OC₂H₅ | —CH₃ | 484 |
| 69 | —C₂H₅ | —C₂H₅ | —H | —H | —H | —H | —Cl | —CH₃ | 474 |

TABLE 6-continued

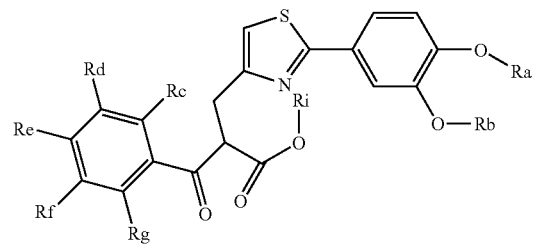

| Examples | Ra | Rb | Rc | Rd | Re | Rf | Rg | Ri | MS(M + 1) |
|---|---|---|---|---|---|---|---|---|---|
| 70 | —C$_2$H$_5$ | —C$_2$H$_5$ | —H | —Cl | —H | —H | —OCH$_3$ | —CH$_3$ | 504 |
| 71 | —C$_2$H$_5$ | —C$_2$H$_5$ | —H | —H | —H | —H | —CH$_3$ | —CH$_3$ | 454 |

Examples 72 to 75

According to the production process of Example 58, the following compounds of Examples 72 to 75 were produced (Table 7). Table 7 also shows physicochemical characteristics of these compounds.

TABLE 7

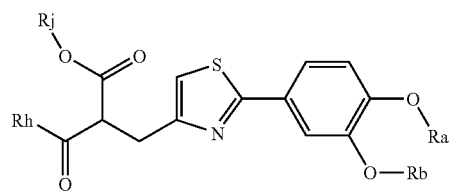

| Examples | Ra | Rb | Rh | Rj | MS (M + 1) |
|---|---|---|---|---|---|
| 72 | —C$_2$H$_5$ | —C$_2$H$_5$ | -2-PYRIDYL | —CH$_3$ | 441 |
| 73 | —C$_2$H$_5$ | —C$_2$H$_5$ | -3-PYRIDYL | —CH$_3$ | 441 |
| 74 | —C$_2$H$_5$ | —C$_2$H$_5$ | ![pyrrole with N-CH3 and 2-methyl] | —CH$_3$ | 443 |

TABLE 7-continued

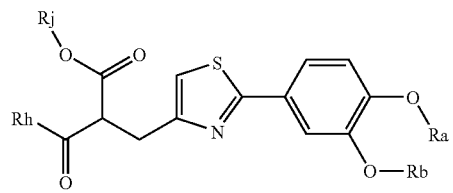

| Examples | Ra | Rb | Rh | Rj | MS (M + 1) |
|---|---|---|---|---|---|
| 75 | —C$_2$H$_5$ | —C$_2$H$_5$ | ![3-methyl-2-methylpyridyl] | —CH$_3$ | 455 |

Examples 76 to 82

According to the production process of Example 58, the following compounds of Examples 76 to 82 were produced (Table 8). Table 8 also shows physicochemical characteristics of these compound.

TABLE 8

| Examples | Ra | Rb | Rh | Rj | NMR δ ppm (CDCl$_3$) |
|---|---|---|---|---|---|
| 76 | —C$_2$H$_5$ | —C$_2$H$_5$ | -2-FURYL | —CH$_3$ | 7.60 (1H, d, J = 1.6 Hz), 7.43 (1H, d, J = 2.0 Hz), 7.4-7.3 (2H, m), 6.89 (1H, s), 6.86 (1H, d, J = 8.4 Hz), 6.52 (1H, dd, J = 1.7 Hz, 3.6 Hz), 4.81 (1H, t, J = 7.4 Hz), 4.2-4.0 (4H, m), 3.71 (3H, s), 3.48 (2H, d, J = 7.4 Hz), 1.5-1.4 (6H, m) |
| 77 | —C$_2$H$_5$ | —C$_2$H$_5$ | -4-PYRIDYL | —CH$_3$ | 8.8-8.7 (2H, m), 7.9-7.8 (2H, m), 7.32 (1H, d, J = 1.9 Hz), 7.3-7.2 (1H, m), 6.90 (1H, s), 6.83 (1H, d, J = 8.3 Hz), 5.05 (1H, dd, J = 6.6 Hz, 8.0 Hz), 4.2-4.0 (4H, m), 3.70 (3H, s), 3.6-3.4 (2H, m). 1.5-1.4 (6H, m) |

TABLE 8-continued

Structure: Rj-O-C(=O)-C(CH2-[thiazole-2-yl-(3,4-di-O-substituted-phenyl)])-C(=O)-Rh, with Ra on 4-O and Rb on 3-O of the phenyl.

| Examples | Ra | Rb | Rh | Rj | NMR δ ppm (CDCl₃) |
|---|---|---|---|---|---|
| 78 | —C₂H₅ | —C₂H₅ | 3-methoxy-2-methylpyridin-(yl) (H₃C—O on pyridine with 2-methyl) | —CH₃ | 8.23 (1H, dd, J = 1.2 Hz, 4.4 Hz), 7.5-7.3 (4H, m), 6.92 (1H, s), 6.85 (1H, d, J = 8.4 Hz), 5.30 (1H, dd, J = 6.9 Hz, 7.8 Hz), 4.2-4.0 (4H, m), 3.89 (3H, s), 3.65 (3H, s), 3.6-3.4 (2H, m), 1.5-1.4 (6H, m) |
| 79 | —C₂H₅ | —C₂H₅ | 3-(isopropoxy)-2-methylpyridin-(yl) | —CH₃ | 8.21 (1H, dd, J = 1.7 Hz, 4.0Hz), 7.45 (1H, d, J = 1.9 Hz), 7.4-7.2 (3H, m), 6.92 (1H, s), 6.85 (1H, d, J = 8.4 Hz), 5.28 (1H, t, J = 7.3 Hz), 4.6-4.5 (1H, m), 4.2-4.0 (4H, m), 3.65 (3H, s), 3.6-3.4 (2H, m), 1.5-1.4 (6H, m), 1.37 (3H, s), 1.35 (3H, s) |
| 80 | —C₂H₅ | —C₂H₅ | 1-methyl-2-benzimidazolyl | —CH₃ | 7.89 (1H, d, J = 8.1 Hz), 7.5-7.3 (4H, m), 7.19 (1H, dd, J = 2.1 Hz, 8.4 Hz), 6.95 (1H, s), 6.74 (1H, d, J = 8.4 Hz), 5.59 (1H, dd, J = 6.0 Hz, 8.9 Hz), 4.2-3.9 (7H, m), 3.71 (3H, s), 3.7-3.4 (2H, m), 1.5-1.3 (6H, m) |
| 81 | —C₂H₅ | —C₂H₅ | 2-methylpyrazinyl | —CH₃ | 9.27 (1H, d, J = 1.5 Hz), 8.73 (1H, d, J = 2.5 Hz), 8.62 (1H, dd, J = 1.5 Hz, 2.4 Hz), 7.31 (1H, d, J = 2.1 Hz), 7.3-7.2 (1H, m), 6.91 (1H, s), 6.81 (1H, d, J = 8.4 Hz), 5.38 (1H, dd, J = 5.8 Hz, 8.9 Hz), 4.2-4.0 (4H, m), 3.67 (3H, s), 3.6-3.4 (2H, m), 1.5-1.4 (6H, m) |
| 82 | —C₂H₅ | —C₂H₅ | 2-methylquinolinyl | —CH₃ | 8.27 (1H, d, J = 8.5 Hz), 8.2-8.1 (2H, m), 7.9-7.6 (3H, m), 7.37 (1H, d, J = 2.0 Hz), 7.29 (1H, dd, J = 2.1 Hz, 8.4 Hz), 6.93 (1H, s), 6.80 (1H, d, J = 8.3 Hz), 5.60 (1H, dd, J = 6.3 Hz, 8.3 Hz), 4.2-4.0 (4H, m), 3.7-3.5 (5H, m), 1.5-1.3 (6H, m) |

Examples 83 to 86

According to the production process of Example 58, the following compounds of Examples 83 to 86 were produced (Table 9). Table 9 also shows physicochemical characteristics of these compounds.

TABLE 9

Structure: Rj-O-C(=O)-CH(CH2-[thiazole-2-yl-(3,4-di-O-substituted-phenyl)])-C(=O)-Rh, with Ra on 4-O and Rb on 3-O of the phenyl.

| Examples | Ra | Rb | Rh | Rj | NMR δ ppm (CDCl₃) |
|---|---|---|---|---|---|
| 83 | —C₂H₅ | —C₂H₅ | 3-methyl-2-methylpyridin-(yl) (H₃C on pyridine ring with 2-methyl) | —CH₃ | 8.5-8.4 (1H, m), 7.56 (1H, d, J = 7.8 Hz), 7.41 (1H, d, J = 2.0 Hz), 7.4-7.2 (2H, m), 6.91 (1H, s), 6.84 (1H, d, J = 8.4 Hz), 5.35 (1H, dd, J = 6.6 Hz, 8.1 Hz), 4.2-4.0 (4H, m), 3.66 (3H, s), 3.6-3.3 (2H, m), 2.56 (3H, s), 1.5-1.4 (6H, m) |

TABLE 9-continued

[Structure: Rj-O-C(=O)-CH(-C(=O)-Rh)-CH2-[thiazole]-[phenyl with OMe groups Ra, Rb]]

| Examples | Ra | Rb | Rh | Rj | NMR δ ppm (CDCl₃) |
|---|---|---|---|---|---|
| 84 | —C₂H₅ | —C₂H₅ | [3-(benzyloxy)-2-methylpyridin-yl] | —CH₃ | 8.3-8.2 (1H, m), 7.5-7.3 (9H, m), 6.91 (1H, s), 6.82 (1H, d, J = 8.4 Hz), 5.32 (1H, t, J = 7.4 Hz), 5.17 (2H, s), 4.2-4.0 (4H, m), 3.65 (3H, s), 3.6-3.4 (2H, m), 1.5-1.4 (6H, m) |
| 85 | —C₂H₅ | —C₂H₅ | [3,4-dimethylpyridin-yl] | —CH₃ | 9.02 (1H, s), 8.51 (1H, d, J = 5.0 Hz), 7.4-7.3 (2H, m), 7.15 (1H, d, J = 5.0 Hz), 6.91 (1H, s), 6.85 (1H, d, J = 8.3 Hz), 5.1-5.0 (1H, m), 4.2-4.0 (4H, m), 3.70 (3H, s), 3.6-3.4 (2H, m), 2.43 (3H, s), 1.5-1.4 (6H, m) |
| 86 | —C₂H₅ | —C₂H₅ | [1,5-dimethyl-1H-pyrrol-2-yl] | —C(CH₃)₃ | 7.48 (1H, d, J = 2.1 Hz), 7.40 (1H, dd, J = 2.1 Hz, 8.3 Hz), 7.14 (1H, dd, J = 1.7 Hz, 4.2 Hz), 6.9-6.8 (3H, m), 6.11 (1H, dd, J = 2.5 Hz, 4.2 Hz), 4.64 (1H, t, J = 7.3 Hz), 4.2-4.1 (4H, m), 3.92 (3H, s), 3.41 (2H, d, J = 7.4 Hz), 1.5-1.4 (6H, m), 1.37 (9H, s) |

Example 87

Production of 3-[2-(3,4-diethoxyphenyl)thiazole-4-yl]-1-(3-ethoxypyridine-2-yl)-1-propanone Methyl 2-[2-(3,4-diethoxyphenyl)thiazole-4-ylmethyl]-3-(3-ethoxypyridine-2-yl)-3-oxopropionate (730 mg, 1.5 mmol) was added to a mixture of acetic acid (4.5 ml) and hydrochloric acid (1.5 ml), followed by heating with stirring at 100 to 110° C. for 6 hours. After cooling to room temperature, the reaction mixture was added to an aqueous solution of sodium carbonate (5.3 g, 0.05 mol), and the resulting mixture was subjected to extraction with ethyl acetate. The organic layer was washed with a saturated salt solution, and dried over anhydrous magnesium sulfate. The solvent was distilled off under reduced pressure, and the residue was purified by silica gel column chromatography (eluent: ethyl acetate/n-hexane=3/4). The solvent was distilled off under reduced pressure, and the residue was recrystallized from ethanol, to thereby obtain 475 g (yield: 74%) of 3-[2-(3,4-diethoxyphenyl)thiazole-4-yl]-1-(3-ethoxypyridine-2-yl)-1-propenone as colorless needles.

Melting point: 66.7-68.2° C.

Example 88

Production of 3-[2-(3,4-diethoxyphenyl)thiazole-4-yl]-1-(3-methoxypyridine-2-yl)-1-propanone Triethylamine (0.19 ml, 1.36 mmol) and sulfur trioxide pyridine complex (0.11 g, 0.68 mmol) were added to a solution (5 ml) of 3-[2-(3,4-diethoxyphenyl)thiazole-4-yl]-1-(3-methoxypyridine-2-yl)-1-propane-1-ol (0.14 g, 0.34 mmol) in DMSO, and the resulting mixture was stirred at room temperature for 1 hour. Water was added to the reaction mixture, and extraction with diethyl ether was carried out three times. The organic layer was dried over anhydrous sodium sulfate. The solvent was distilled off under reduced pressure, and the residue was purified by preparative thin-layer silica gel column chromatography (eluent: dichloromethane/methanol=10/1). The solvent was distilled off under reduced pressure, to give 120 mg (yield: 86%) of 3-[2-(3,4-diethoxyphenyl)thiazole-4-yl]-1-(3-methoxypyridine-2-yl)-1-propanone as a colorless oil. The oil was recrystallized from hydrous ethanol, to thereby obtain 3-[2-(3,4-diethoxyphenyl)thiazole-4-yl]-1-(3-methoxypyridine-2-yl)-1-propanone as yellow needles.

Melting point: 79.2-79.7° C.

Example 89

Production of 3-[2-(3,4-diethoxyphenyl)thiazole-4-yl]-1-(2-methoxyphenyl)-1-propanone (E)-3-[2-(3,4-diethoxyphenyl)thiazole-4-yl]-1-(2-methoxyphenyl)propenone (1.62 g, 4.0 mmol) was dissolved in a mixed solvent of ethyl acetate (40 ml), methanol (10 ml) and DMF (10 ml), and 400 mg of 10% palladium/carbon was added to perform catalytic reduction in a hydrogen atmosphere at room temperature and atmospheric pressure for 4 hours. The reaction mixture was filtered, the solvent was distilled off under reduced pressure, and the residue was purified by silica gel column chromatography (eluent: ethyl acetate/n-hexane=3/2 to 1/1). The solvent was distilled off under reduced pressure, and the residue was recrystallized from diethyl ether, to thereby obtain 750 mg (yield: 46%) of 3-[2-(3,4-diethoxyphenyl)thiazole-4-yl]-1-(2-methoxyphenyl)-1-propanone as colorless prisms.

Melting point: 68.9-69.3° C.

Example 90

Production of 3-[2-(3,4-diethoxyphenyl)thiazole-4-yl]-1-thiazole-2-yl-1-propanone A solution (2 ml) of thiazole (129 mg, 1.5 mmol) in THF was cooled to −70° C., and n-butyllithium (a 2.44M hexane solution) (0.62 ml, 1.5 mmol) was added, and the resulting mixture was stirred at −70° C. for 30 minutes. A solution (4 ml) of 3-[2-(3,4-diethoxyphenyl)thiazole-4-yl]-N-methoxy-N-methylpropionamide (500 mg, 1.4 mmol) in THF was added to the reaction mixture, followed by stirring at −70° C. for 3 hours. After heating to room temperature, a saturated aqueous ammonium chloride solution was added to the reaction mixture, followed by extraction with ethyl acetate. The organic layer was washed with a saturated salt solution, and dried over anhydrous magnesium sulfate. The solvent was distilled off under reduced pressure, and the residue was purified by silica gel column chromatography (eluent: ethyl acetate/n-hexane=1/5). The solvent was distilled off under reduced pressure, and the residue was recrystallized from ethanol, to thereby obtain 350 mg (yield: 66%) of 3-[2-(3,4-diethoxyphenyl)thiazole-4-yl]-1-thiazole-2-yl-1-propanone as colorless needles.

Melting point: 93.1-94.4° C.

Examples 91 to 108

According to the production process of Example 87, the following compounds of Examples 91 to 108 were produced (Table 10). Table 10 also shows physicochemical characteristics of these compounds.

TABLE 10

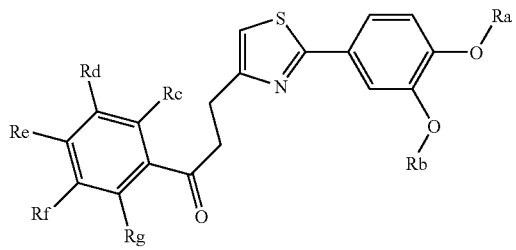

| Examples | Ra | Rb | Rc | Rd | Re | Rf | Rg | Melting point (° C.) | Salt |
|---|---|---|---|---|---|---|---|---|---|
| 91 | —C$_2$H$_5$ | —C$_2$H$_5$ | —H | —H | —H | —H | —H | 113.3-113.6 | — |
| 92 | —C$_2$H$_5$ | —C$_2$H$_5$ | —H | —H | —OH | —OH | —H | 153.2-153.8 | hydrochloride |
| 93 | —CH$_3$ | —CH$_3$ | —H | —H | —OC$_2$H$_5$ | —OC$_2$H$_5$ | —H | 141.3-142.4 | — |
| 94 | —CH$_3$ | —CH$_3$ | —H | —H | —OCOCH$_3$ | —OCOCH$_3$ | —H | 128-128.5 | — |
| 95 | —C$_2$H$_5$ | —C$_2$H$_5$ | —OCH$_3$ | —H | —H | —OCH$_3$ | —H | 97.8-98.5 | — |
| 96 | —C$_2$H$_5$ | —C$_2$H$_5$ | —H | —H | —H | —H | —OCH$_3$ | 68.9-69.3 | — |
| 97 | —C$_2$H$_5$ | —C$_2$H$_5$ | —H | —H | —H | —H | —OC$_6$H$_5$ | 118.2-119 | — |
| 98 | —C$_2$H$_5$ | —C$_2$H$_5$ | —OH | —H | —H | —H | —H | 113.7-114.9 | — |
| 99 | —C$_2$H$_5$ | —C$_2$H$_5$ | —CF$_3$ | —H | —H | —H | —H | 91.7-93 | — |
| 100 | —C$_2$H$_5$ | —C$_2$H$_5$ | —OC$_2$H$_5$ | —H | —H | —H | —H | 84.3-86.1 | — |
| 101 | —C$_2$H$_5$ | —C$_2$H$_5$ | —F | —H | —H | —H | —H | 82.5-83.5 | — |
| 102 | —C$_2$H$_5$ | —C$_2$H$_5$ | —CN | —H | —H | —H | —H | 113.7-114.8 | — |
| 103 | —C$_2$H$_5$ | —C$_2$H$_5$ | —Br | —H | —H | —H | —H | 66.1-67.9 | — |
| 104 | —C$_2$H$_5$ | —C$_2$H$_5$ | —Cl | —H | —H | —H | —H | 64.4-65.1 | — |
| 105 | —C$_2$H$_5$ | —C$_2$H$_5$ | —H | —H | —H | —H | —CO$_2$CH$_3$ | 91.7-92.9 | — |
| 106 | —C$_2$H$_5$ | —C$_2$H$_5$ | —OCH$_3$ | —H | —Cl | —H | —H | 102.8-104.2 | — |
| 107 | —C$_2$H$_5$ | —C$_2$H$_5$ | —CH$_3$ | —H | —H | —H | —H | 107.1-107.4 | — |
| 108 | —C$_2$H$_5$ | —C$_2$H$_5$ | —OCH$_3$ | —H | —H | —Cl | —H | 90.2-92 | — |

Examples 109 to 114

According to the production process of Example 87, the following compounds of Examples 109 to 114 were produced (Table 11). Table 11 also shows physicochemical characteristics of these compounds.

TABLE 11

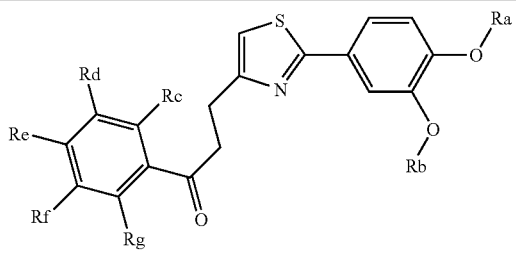

| Examples | Ra | Rb | Rc | Rd | Re | Rf | Rg | NMR δ ppm (CDCl$_3$) |
|---|---|---|---|---|---|---|---|---|
| 109 | —C$_2$H$_5$ | —C$_2$H$_5$ | —OCH$_3$ | —Cl | —H | —H | —H | 7.6-7.3 (4H, m), 7.10 (1H, t, J = 7.8 Hz), 6.9-6.8 (2H, m), 4.2-4.0 (4H, m), 3.87 (3H, s), 3.46 (2H, t, J = 7.1 Hz), 3.21 (2H, t, J = 7.1 Hz), 1.5-1.4 (6H, m) |
| 110 | —C$_2$H$_5$ | —C$_2$H$_5$ | —N(CH$_3$)$_2$ | —H | —H | —H | —H | 7.49 (1H, d, J = 2.0 Hz), 7.43-7.3 (3H, m), 7.0-6.8 (4H, m), 4.2-4.1 (4H, m), 3.48 (2H, t, J = 7.3 Hz), 3.18 (2H, t, J = 7.3 Hz), 2.73 (6H, s), 1.5-1.4 (6H, m) |
| 111 | —C$_2$H$_5$ | —C$_2$H$_5$ | —H | —H | —H | —H | —CON(CH$_3$)$_2$ | 7.88 (1H, d, J = 7.4 Hz), 7.6-7.3 (4H, m), 7.3-7.2 (1H, m), 6.9-6.8 (2H, m), 4.2-4.1 (4H, m), 3.45 (2H, t, J = 7.3 Hz), 3.20 (2H, t, J = 7.2 Hz), 3.14 (3H, s), 2.76 (3H, s), 1.5-1.4 (6H, m) |
| 112 | —C$_2$H$_5$ | —C$_2$H$_5$ | —H | —H | —H | —H | —CO$_2$H | 10.08 (1H, br), 7.87 (1H, d, J = 7.1 Hz), 7.7-7.3 (5H, m), 6.92 (1H, s), 6.89 (1H, d, J = 8.31-Iz), 4.2-4.0 (4H, m), 3.6-3.4 (1H, m), 3.1-3.0 (1H, m), 2.6-2.2 (2H, m), 1.5-1.4 (6H, m) |
| 113 | —C$_2$H$_5$ | —C$_2$H$_5$ | —H | —H | —H | —H | —C$_6$H$_5$ | 7.5-7.3 (11H, m), 6.87 (1H, d, J = 8.4 Hz), 6.63 (1H, s), 4.2-4.0 (4H, m), 3.0-2.9 (2H, m), 2.8-2.7 (2H, m), 1.5-1.4 (6H, m) |
| 114 | —C$_2$H$_5$ | —C$_2$H$_5$ | —OCH$_2$OCH$_3$ | —H | —H | —H | —H | 7.69 (1H, dd, J = 7.8 Hz), 7.5-7.3 (3H, m), 7.19 (1H, d, J = 8.4 Hz), 7.1-7.0 (1H, m), 6.88 (1H, s), 6.85 (1H, d, J = 8.4 Hz), 5.22 (2H, s), 5.1-5.0 (1H, m), 4.2-4.0 (4H, m), 3.68 (3H, s), 3.6-3.3 (5H, m), 1.5-1.4 (6H, m) |

Examples 115 to 147

According to the production process of Example 87, the following compounds of Examples 115 to 147 were produced (Table 12). Table 12 also shows physicochemical characteristics of these compounds.

TABLE 12

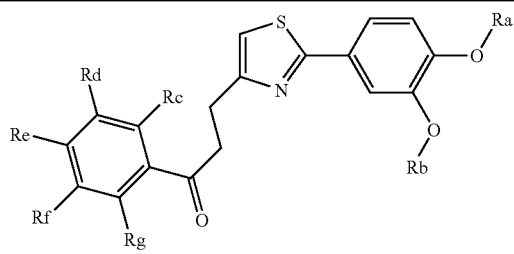

| Examples | Ra | Rb | Rc | Rd | Re | Rf | Rg | MS (M + 1) |
|---|---|---|---|---|---|---|---|---|
| 115 | —C$_2$H$_5$ | —C$_2$H$_5$ | —Cl | —H | —Cl | —SO$_2$NH$_2$ | —H | 529 |
| 116 | —C$_2$H$_5$ | —C$_2$H$_5$ | —OCH$_3$ | —H | —H | —SO$_2$NH$_2$ | —H | 491 |
| 117 | —C$_2$H$_5$ | —C$_2$H$_5$ | —H | —H | —CN | —H | —H | 407 |
| 118 | —C$_2$H$_5$ | —C$_2$H$_5$ | —H | —OCH$_3$ | —H | —OCH$_3$ | —H | 442 |
| 119 | —C$_2$H$_5$ | —C$_2$H$_5$ | —H | —H | —H | —CH$_3$ | —H | 396 |
| 120 | —C$_2$H$_5$ | —C$_2$H$_5$ | —H | —H | —CH$_3$ | —H | —H | 396 |
| 121 | —C$_2$H$_5$ | —C$_2$H$_5$ | —H | —H | —N(CH$_3$)$_2$ | —H | —H | 425 |
| 122 | —C$_2$H$_5$ | —C$_2$H$_5$ | —H | —H | —H | —N(CH$_3$)$_2$ | —H | 425 |

TABLE 12-continued

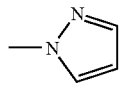

| Examples | Ra | Rb | Rc | Rd | Re | Rf | Rg | MS (M + 1) |
|---|---|---|---|---|---|---|---|---|
| 123 | —$C_2H_5$ | —$C_2H_5$ | —H | —H | —H | —Br | —H | 460 |
| 124 | —$C_2H_5$ | —$C_2H_5$ | —H | —H | —F | —H | —H | 400 |
| 125 | —$C_2H_5$ | —$C_2H_5$ | —H | —H | —$OCH_3$ | —CN | —H | 437 |
| 126 | —$C_2H_5$ | —$C_2H_5$ | —H | —H | —$CH_3$ | —$OCH_3$ | —H | 426 |
| 127 | —$C_2H_5$ | —$C_2H_5$ | —H | —H | —H | —H | —$OCF_3$ | 466 |
| 128 | —$C_2H_5$ | —$C_2H_5$ | —H | —H | —H | —Cl | —H | 416 |
| 129 | —$C_2H_5$ | —$C_2H_5$ | —H | —H | —Cl | —H | —H | 416 |
| 130 | —$C_2H_5$ | —$C_2H_5$ | —H | —H | —$OCH_3$ | —$OCH_3$ | —H | 442 |
| 131 | —$C_2H_5$ | —$C_2H_5$ | —H | —H | —$OCH_3$ | —H | —H | 412 |
| 132 | —$C_2H_5$ | —$C_2H_5$ | —H | —H | —H | —$CF_3$ | —H | 450 |
| 133 | —$C_2H_5$ | —$C_2H_5$ | —H | —H | —H | —Cl | —Cl | 450 |
| 134 | —$C_2H_5$ | —$C_2H_5$ | —H | —H | —H | —H | —$SCH_3$ | 428 |
| 135 | —$C_2H_5$ | —$C_2H_5$ | —H | —H | —$OC_4H_9$ | —H | —H | 454 |
| 136 | —$C_2H_5$ | —$C_2H_5$ | —H | —H | —H | —F | —H | 400 |
| 137 | —$C_2H_5$ | —$C_2H_5$ | —H | —Cl | —H | —H | —Cl | 450 |
| 138 | —$C_2H_5$ | —$C_2H_5$ | —H | —H | —H | —$OCH_3$ | —H | 412 |
| 139 | —$C_2H_5$ | —$C_2H_5$ | —H | —H | —$C_6H_5$ | —H | —H | 458 |
| 140 | —$C_2H_5$ | —$C_2H_5$ | —H | —H | —H | —$OC_2H_5$ | —H | 426 |
| 141 | —$C_2H_5$ | —$C_2H_5$ | —H | —H | —$OC_2H_5$ | —H | —H | 426 |
| 142 | —$C_2H_5$ | —$C_2H_5$ | —H | —H | —$OCH_2C_6H_5$ | —H | —H | 488 |
| 143 | —$C_2H_5$ | —$C_2H_5$ | —H | —H | —H | —$OCF_3$ | —H | 466 |
| 144 | —$C_2H_5$ | —$C_2H_5$ | —H | —H | —$CF_3$ | —H | —H | 450 |
| 145 | —$C_2H_5$ | —$C_2H_5$ | —H | —H | —$C_4H_9$ | —H | —H | 438 |
| 146 | —$C_2H_5$ | —$C_2H_5$ | —H | —H | —H | —H | —$OCH_2C_6H_5$ | 488 |
| 147 | —$C_2H_5$ | —$C_2H_5$ | —H | —H | —OH | —H | —H | 398 |

Examples 148 to 152

According to the production process of Example 87, the following compounds of Examples 148 to 152 were produced (Table 13). Table 13 also shows physicochemical characteristics of these compounds.

TABLE 13

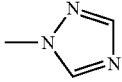

| Examples | Ra | Rb | Rc | Rd | Re | Rf | Rg | MS (M + 1) |
|---|---|---|---|---|---|---|---|---|
| 148 | —$C_2H_5$ | —$C_2H_5$ | —H | —H | (1-pyrazolyl) | —H | —H | 448 |
| 149 | —$C_2H_5$ | —$C_2H_5$ | —H | —H | (1-(1,2,4-triazolyl)) | —H | —H | 449 |

TABLE 13-continued

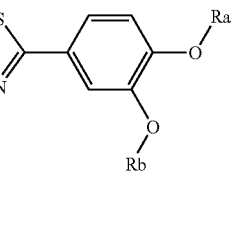

| Examples | Ra | Rb | Rc | Rd | Re | Rf | Rg | MS (M + 1) |
|---|---|---|---|---|---|---|---|---|
| 150 | —C$_2$H$_5$ | —C$_2$H$_5$ | —H | —H | 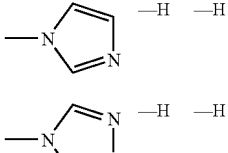 | —H | —H | 448 |
| 151 | —C$_2$H$_5$ | —C$_2$H$_5$ | —H | —H | 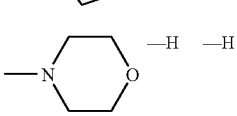 | —H | —H | 449 |
| 152 | —C$_2$H$_5$ | —C$_2$H$_5$ | —H | —H | 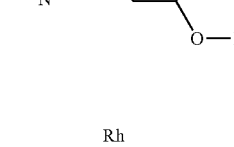 | —H | —H | 467 |

Examples 153 to 157

According to the production process of Example 87, the following compounds of Examples 153 to 157 were produced (Table 14). Table 14 also shows physicochemical characteristics of these compounds.

TABLE 14

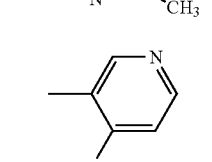

| Examples | Ra | Rb | Rh | Melting point (° C.) |
|---|---|---|---|---|
| 153 | —C$_2$H$_5$ | —C$_2$H$_5$ | -2-PYRIDYL | 92.9-93 |
| 154 | —C$_2$H$_5$ | —C$_2$H$_5$ | -2-FURYL | 110.8-112.5 |
| 155 | —C$_2$H$_5$ | —C$_2$H$_5$ | -2-THIENYL | 106.5-107.4 |
| 156 | —C$_2$H$_5$ | —C$_2$H$_5$ | -4-PYRIDYL | 90.6 -91.1 |
| 157 | —C$_2$H$_5$ | —C$_2$H$_5$ | -3-PYRIDYL | 107.5-108.0 |

Examples 158 to 167

According to the production process of Example 87, the following compounds of Examples 158 to 167 were produced (Table 15). Table 15 also shows physicochemical characteristics of these compounds.

TABLE 15

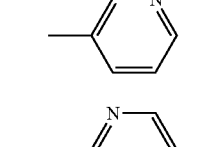

| Examples | Ra | Rb | Rh | Melting point (° C.) |
|---|---|---|---|---|
| 158 | —C$_2$H$_5$ | —C$_2$H$_5$ | 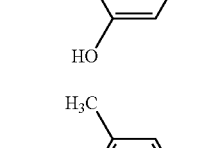 | 59.5-60.5 |
| 159 | —C$_2$H$_5$ | —C$_2$H$_5$ | 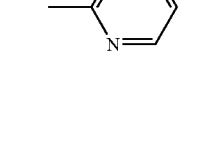 | 118.7-119.6 |
| 160 | —C$_2$H$_5$ | —C$_2$H$_5$ | | 109.1-110.5 |
| 161 | —C$_2$H$_5$ | —C$_2$H$_5$ | | 81.7-83.1 |
| 162 | —C$_2$H$_5$ | —C$_2$H$_5$ | | 87.0 -87.6 |

TABLE 15-continued

[Structure: Rh-C(=O)-CH2-CH2-thiazole-phenyl(-O-Ra)(-O-Rb)]

| Examples | Ra | Rb | Rh | Melting point (° C.) |
|---|---|---|---|---|
| 163 | —C₂H₅ | —C₂H₅ | 2-methylquinolin-yl | 92.1-93.1 |
| 164 | —C₂H₅ | —C₂H₅ | methylpyrazinyl | 117.9-119.2 |
| 165 | —C₂H₅ | —C₂H₅ | 1,2-dimethylimidazol-yl | 80.3-81.9 |
| 166 | —C₂H₅ | —C₂H₅ | 1-methyl-2-methylbenzimidazol-yl | 107.7-108.5 |
| 167 | —C₂H₅ | —C₂H₅ | 1,2-dimethylpyrrol-yl | 92.8-94.2 |

Example 168

According to the production process of Example 87, the following compound of Example 168 was produced (Table 16). Table 16 also shows physicochemical characteristics of the compound.

TABLE 16

[Structure: Rh-C(=O)-CH2-CH2-thiazole-phenyl(-O-Ra)(-O-Rb)]

| Example | Ra | Rb | Rh | NMR δ ppm (DMSO-d6) | Salt |
|---|---|---|---|---|---|
| 168 | —C₂H₅ | —C₂H₅ | 3-(1-methoxyethoxy)-2-methylpyridin-yl | 8.31-8.29 (1H, m), 8.00 (1H, d, J = 8.7 Hz), 7.8-7.7 (1H, m), 7.53 (1H, d, J = 2.1 Hz), 7.44 (1H, dd, J = 2.1 Hz, 8.4 Hz), 7.36 (1H, s), 7.03 (1H, d, J = 8.5 Hz), 4.9-4.7 (1H, m), 4.1-4.0 (4H, m), 3.50 (2H, t, J = 7.2 Hz), 3.11 (2H, t, J = 7.2 Hz), 1.4-1.2 (12H, m) | hydrochloride |

Examples 169 to 178

According to the production process of Example 87, the following compounds of Examples 169 to 178 were produced (Table 17). Table 17 also shows physicochemical characteristics of these compounds.

TABLE 17

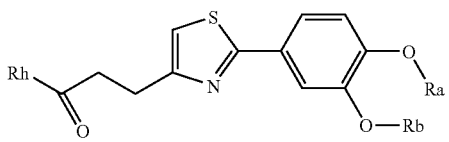

| Examples | Ra | Rb | Rh | MS (M + 1) |
|---|---|---|---|---|
| 169 | —C₂H₅ | —C₂H₅ | 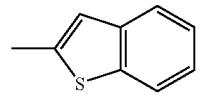 | 451 |
| 170 | —C₂H₅ | —C₂H₅ | | 451 |
| 171 | —C₂H₅ | —C₂H₅ | | 422 |
| 172 | —C₂H₅ | —C₂H₅ | | 386 |
| 173 | —C₂H₅ | —C₂H₅ | | 397 |
| 174 | —C₂H₅ | —C₂H₅ | | 418 |
| 175 | —C₂H₅ | —C₂H₅ | | 386 |
| 176 | —C₂H₅ | —C₂H₅ | | 413 |

TABLE 17-continued

| Examples | Ra | Rb | Rh | MS (M + 1) |
|---|---|---|---|---|
| 177 | —C₂H₅ | —C₂H₅ | | 432 |
| 178 | —C₂H₅ | —C₂H₅ | | 387 |

Examples 179 to 185

According to the production process of Example 87, the following compounds Examples 179 to 185 were produced (Table 18). Table 18 also shows physicochemical characteristics of these compounds.

TABLE 18

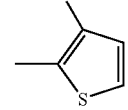

| Examples | Ra | Rb | Rh | MS (M + 1) |
|---|---|---|---|---|
| 179 | —C₂H₅ | —C₂H₅ | | 438 |
| 180 | —C₂H₅ | —C₂H₅ | | 418 |
| 181 | —C₂H₅ | —C₂H₅ | | 444 |
| 182 | —C₂H₅ | —C₂H₅ | | 432 |
| 183 | —C₂H₅ | —C₂H₅ | | 426 |

TABLE 18-continued

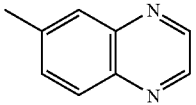

| Examples | Ra | Rb | Rh | MS (M + 1) |
|---|---|---|---|---|
| 184 | —C$_2$H$_5$ | —C$_2$H$_5$ | (6-methylquinoxalin-2-yl) | 434 |
| 185 | —C$_2$H$_5$ | —C$_2$H$_5$ | (6-methylquinolin-2-yl) | 433 |

Example 186

Production of 3-[2-(3,4-diethoxyphenyl)thiazole-4-yl]-1-(2-methoxyphenyl)-1-propanol Sodium borohydride (20 mg, 0.53 mmol) was added to a mixed solution of 3-[2-(3,4-diethoxyphenyl)thiazole-4-yl]-1-(2-methoxyphenyl)-1-propanone (458 mg, 1.11 mmol) in THF (10 ml) and methanol (10 ml) at room temperature, and the resulting mixture was stirred at the same temperature for 1 hour. A saturated aqueous ammonium chloride solution was added to the reaction mixture, followed by extraction with ethyl acetate. The organic layer was dried over anhydrous sodium sulfate. The solvent was distilled off under reduced pressure, and the residue was purified by silica gel column chromatography (eluent: ethyl acetate/n-hexane=2/1). The solvent was distilled off under reduced pressure, and the residue was recrystallized from a diethyl ether/n-hexane mixed solvent, to thereby obtain 336 mg (yield: 73%) of 3-[2-(3,4-diethoxyphenyl)thiazole-4-yl]-1-(2-methoxyphenyl)-1-propanol as a white powder.

Melting point: 78.2-79° C.

Example 187

Production of 3-[2-(3,4-diethoxyphenyl)thiazole-4-yl]-1-(3-methoxypyridine-2-yl)-1-propanol dihydrochloride According to the production process of Example 186, 3-[2-(3,4-diethoxyphenyl)thiazole-4-yl]-1-(3-methoxypyridine-2-yl)-1-propanol dihydrochloride was produced.

Melting point: 161.0-161.5° C.

Example 188

Production of 3-[2-(3,4-diethoxyphenyl)thiazole-4-yl]-1-(3-methoxypyridine-2-yl)-1-propanol A solution of 2-bromo-3-methoxypyridine (1.65 g, 8.78 mmol) in THF was cooled to −78° C., and 5.23 ml (8.16 mmol) of a 1.57 N solution of n-butyllithium in n-hexane was added dropwise. The resulting mixture was stirred at the same temperature for 45 minutes, and a solution (15 ml) of 3-[2-(3,4-diethoxyphenyl)thiazole-4-yl]propionaldehyde (1.34 g, 4.39 mmol) in THF was added dropwise. After stirring at the same temperature for 30 minutes, the temperature of the mixture was raised to −30° C. over a period of 30 minutes. A saturated aqueous ammonium chloride solution was added to the reaction mixture, followed by extraction with ethyl acetate. The organic layer was washed with a saturated salt solution, and dried over anhydrous sodium sulfate. The solvent was distilled off under reduced pressure, and the residue was purified by silica gel column chromatography (eluent: ethyl acetate/n-hexane=1/1). The solvent was distilled off under reduced pressure, and the residue was purified by preparative thin-layer silica gel column chromatography (eluent: ethyl acetate/n-hexane=1/2). The solvent was distilled off under reduced pressure, to thereby obtain 470 mg (yield: 26%) of 3-[2-(3,4-diethoxyphenyl)thiazole-4-yl]-1-(3-methoxypyridine-2-yl)-1-propanol as a yellow oil.

Examples 189 to 208

According to the production process of Example 186, the following compounds of Examples 189 to 208 were produced (Table 19). Table 19 also shows physicochemical characteristics of these compounds.

TABLE 19

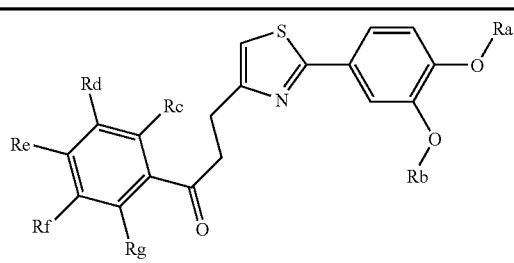

| Examples | Ra | Rb | Rc | Rd | Re | Rf | Rg | MS (M + 1) |
|---|---|---|---|---|---|---|---|---|
| 189 | —C$_2$H$_5$ | —C$_2$H$_5$ | —H | —H | —H | —H | —H | 384 |
| 190 | —C$_2$H$_5$ | —C$_2$H$_5$ | —H | —H | —CN | —H | —H | 409 |
| 191 | —C$_2$H$_5$ | —C$_2$H$_5$ | —H | —OCH$_3$ | —H | —OCH$_3$ | —H | 444 |
| 192 | —C$_2$H$_5$ | —C$_2$H$_5$ | —H | —H | —H | —CH$_3$ | —H | 398 |
| 193 | —C$_2$H$_5$ | —C$_2$H$_5$ | —H | —H | —CH$_3$ | —H | —H | 398 |
| 194 | —C$_2$H$_5$ | —C$_2$H$_5$ | —H | —H | —N(CH$_3$)$_2$ | —H | —H | 426 (M+) |
| 195 | —C$_2$H$_5$ | —C$_2$H$_5$ | —H | —H | —H | —N(CH$_3$)$_2$ | —H | 427 |
| 196 | —C$_2$H$_5$ | —C$_2$H$_5$ | —H | —H | —H | —H | —Br | 462 |

TABLE 19-continued

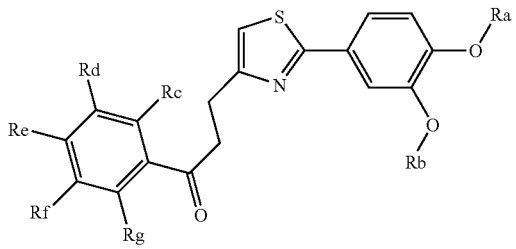

| Examples | Ra | Rb | Rc | Rd | Re | Rf | Rg | MS (M + 1) |
|---|---|---|---|---|---|---|---|---|
| 197 | —C₂H₅ | —C₂H₅ | —H | —H | —H | —H | —OC₂H₅ | 428 |
| 198 | —C₂H₅ | —C₂H₅ | —H | —H | —H | —Br | —H | 462 |
| 199 | —C₂H₅ | —C₂H₅ | —H | —H | —F | —H | —H | 402 |
| 200 | —C₂H₅ | —C₂H₅ | —H | —H | —OCH₃ | —CN | —H | 439 |
| 201 | —C₂H₅ | —C₂H₅ | —H | —H | —CH₃ | —OCH₃ | —H | 428 |
| 202 | —C₂H₅ | —C₂H₅ | —H | —H | —H | —H | —OCF₃ | 468 |
| 203 | —C₂H₅ | —C₂H₅ | —H | —H | —H | —H | —OCH₃ | 414 |
| 204 | —C₂H₅ | —C₂H₅ | —H | —H | —Cl | —H | —H | 418 |
| 205 | —C₂H₅ | —C₂H₅ | —H | —H | —H | —H | —Cl | 418 |
| 206 | —C₂H₅ | —C₂H₅ | —H | —Cl | —H | —H | —OCH₃ | 448 |
| 207 | —C₂H₅ | —C₂H₅ | —H | —H | —H | —CF₃ | —H | 452 |
| 208 | —C₂H₅ | —C₂H₅ | —H | —OCH₃ | —H | —H | —OCH₃ | 444 |

Examples 209 to 225

According to the production process of Example 186, the following compounds of Examples 209 to 225 were produced (Table 20). Table 20 also shows physicochemical characteristics of these compounds.

TABLE 20

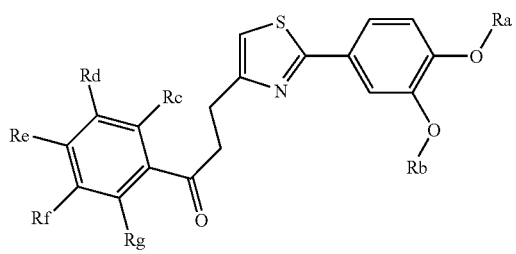

| Examples | Ra | Rb | Rc | Rd | Re | Rf | Rg | MS (M + 1) |
|---|---|---|---|---|---|---|---|---|
| 209 | —C₂H₅ | —C₂H₅ | —H | —H | —H | —Cl | —Cl | 452 |
| 210 | —C₂H₅ | —C₂H₅ | —H | —H | —H | —H | —SCH₃ | 430 |
| 211 | —C₂H₅ | —C₂H₅ | —H | —H | —H | —F | —H | 402 |
| 212 | —C₂H₅ | —C₂H₅ | —H | —Cl | —H | —H | —Cl | 452 |
| 213 | —C₂H₅ | —C₂H₅ | —H | —H | —H | —OCH₃ | —H | 414 |
| 214 | —C₂H₅ | —C₂H₅ | —H | —H | —C₆H₅ | —H | —H | 460 |
| 215 | —C₂H₅ | —C₂H₅ | —H | —H | —OC₂H₅ | —H | —H | 428 |
| 216 | —C₂H₅ | —C₂H₅ | —H | —H | —H | —H | —F | 402 |
| 217 | —C₂H₅ | —C₂H₅ | —H | —H | —H | —OCF₃ | —H | 468 |
| 218 | —C₂H₅ | —C₂H₅ | —H | —H | —CF₃ | —H | —H | 452 |
| 219 | —C₂H₅ | —C₂H₅ | —H | —H | —H | —H | —CF₃ | 452 |
| 220 | —C₂H₅ | —C₂H₅ | —H | —H | —C₄H₉ | —H | —H | 440 |
| 221 | —C₂H₅ | —C₂H₅ | —H | —H | —H | —H | —CN | 409 |
| 222 | —C₂H₅ | —C₂H₅ | —H | —H | —OCH₃ | —OCH₃ | —H | 444 |
| 223 | —C₂H₅ | —C₂H₅ | —H | —H | —OCH₃ | —H | —H | 414 |
| 224 | —C₂H₅ | —C₂H₅ | —H | —H | —OC₄H₉ | —H | —H | 456 |
| 225 | —C₂H₅ | —C₂H₅ | —H | —H | —OC₂H₅ | —H | —H | 428 |

Examples 226 to 237

According to the production process of Example 186, the following compounds of Examples 226 to 237 were produced (Table 21). Table 21 also shows physicochemical characteristics of these compounds.

TABLE 21

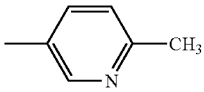

| Examples | Ra | Rb | Rh | MS (M + 1) |
|---|---|---|---|---|
| 226 | —C$_2$H$_5$ | —C$_2$H$_5$ | -2-FURYL | 374 |
| 227 | —C$_2$H$_5$ | —C$_2$H$_5$ | -3-PYRIDYL | 385 |
| 228 | —C$_2$H$_5$ | —C$_2$H$_5$ | -4-PYRIDYL | 385 |
| 229 | —C$_2$H$_5$ | —C$_2$H$_5$ | -2-THIENYL | 390 |
| 230 | —C$_2$H$_5$ | —C$_2$H$_5$ | 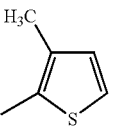 | 388 |
| 231 | —C$_2$H$_5$ | —C$_2$H$_5$ | 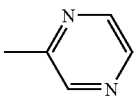 | 399 |
| 232 | —C$_2$H$_5$ | —C$_2$H$_5$ | 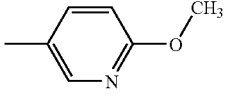 | 404 |
| 233 | —C$_2$H$_5$ | —C$_2$H$_5$ | 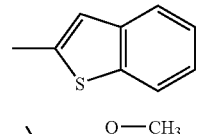 | 386 |
| 234 | —C$_2$H$_5$ | —C$_2$H$_5$ | 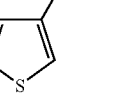 | 415 |
| 235 | —C$_2$H$_5$ | —C$_2$H$_5$ | 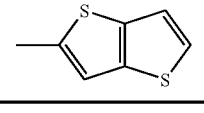 | 440 |
| 236 | —C$_2$H$_5$ | —C$_2$H$_5$ |  | 420 |
| 237 | —C$_2$H$_5$ | —C$_2$H$_5$ |  | 446 |

Example 238

Production of 2-{3-[2-(3,4-diethoxyphenyl)thiazole-4-yl]propyl}-3-methoxypyridine dihydrochloride Hydrazine hydrate (0.18 ml, 3.6 mmol) and potassium hydroxide (136 mg, 2.4 mmol) were added to a solution (5 ml) of 3-[2-(3,4-diethoxyphenyl)thiazole-4-yl]-1-(3-methoxy-pyridine-2-yl)-1-propanone (500 mg, 1.2 mmol) in diethylene glycol, and the resulting mixture was heated to 150° C. and stirred for 1 hour. After cooling to room temperature, water was added to the reaction mixture, followed by extraction with ethyl acetate. The organic layer was washed with a saturated salt solution, and dried over anhydrous magnesium sulfate. The solvent was distilled off under reduced pressure, and the residue was purified by silica gel column chromatography (eluent: ethyl acetate/n-hexane=3/4). The solvent was distilled off under reduced pressure, and the residue was dissolved in 4 ml of ethanol. A 1N hydrogen chloride ethanol solution (1.6 ml) was added, the solvent was distilled off under reduced pressure, and the residue was recrystallized from an ethanol/ethyl acetate mixed solvent, to thereby obtain 320 mg (yield: 73%) of 2-{3-[2-(3,4-diethoxyphenyl)thiazole-4-yl]propyl}-3-methoxypyridine dihydrochloride as a white powder.

Melting point: 169.4-171.2° C.

Example 239

Production of 2-{3-[2-(3,4-diethoxyphenyl)thiazole-4-yl]propionyl}benzonitrile

Zinc (II) cyanide (purity of 60%) (140 mg, 0.7 mmol) and tetrakis(triphenylphosphine)palladium (19 mg, 0.016 mmol) were added to a solution (1 ml) of 1-(2-bromophenyl)-3-[2-(3,4-diethoxyphenyl)thiazole-4-yl]propane-1-one (150 mg, 0.33 mmol) in DMF, and the mixture was stirred with heating in an argon atmosphere at 100° C. for 2 hours. After cooling to room temperature, water and ethyl acetate was added to the reaction mixture, the resulting mixture was filtered through Celite, and the filtrate was separated into layers. The organic layer was washed with a saturated salt solution and dried over anhydrous magnesium sulfate. The solvent was distilled off under reduced pressure, and the residue was purified by silica gel column chromatography (eluent: ethyl acetate/n-hexane=3/4). The solvent was distilled off under reduced pressure, and the residue was recrystallized from ethanol, to thereby obtain 70 mg (yield: 53%) of 2-{3-[2-(3,4-diethoxyphenyl)thiazole-4-yl]propionyl}benzonitrile as colorless needles.

Melting point: 113.7-114.8° C.

Example 240

Production of methyl 2-{3-[2-(3,4-diethoxyphenyl)thiazole-4-yl]propionyl}benzoate Sodium hydrogencarbonate (79 mg, 0.94 mmol) and methyl iodide (0.04 ml, 0.56 mmol) were added to a solution (4 ml) of 2-{3-[2-(3,4-diethoxyphenyl)thiazole-4-yl]propionyl}benzoic acid (200 mg, 0.47 mmol) in DMF, followed by stirring at room temperature overnight. Water was added to the reaction mixture, and extraction with ethyl acetate was performed. The organic layer was washed with a saturated salt solution, and dried over anhydrous magnesium sulfate. The solvent was distilled off under reduced pressure, and the residue was purified by silica gel column chromatography (eluent: ethyl acetate/n-hexane=1/3). The solvent was distilled off under reduced pressure, and the residue was recrystallized from ethanol, to thereby obtain 190 mg (yield: 92%) of methyl 2-{3-[2-(3,4-diethoxyphenyl)thiazole-4-yl]propionyl}benzoate as colorless needles.

Melting point: 91.7-92.9° C.

Example 241

Production of 2-{3-[2-(3,4-diethoxyphenyl)thiazole-4-yl]propionyl}-N,N-dimethylbenzamide 1-(3-dimethylaminopropyl)-3-ethylcarbodiimide (WSC) (54 mg, 0.29 mmol), 1-hydroxybenzotriazol (HOBT) (43 mg, 0.29 mmol), and a 50% aqueous dimethylamine solution (0.025 ml, 0.29 mmol) were added at room temperature to a solution (2 ml) of 2-{3-[2-(3,4-diethoxyphenyl)thiazole-4-yl]propionyl}benzoic acid (100 mg, 0.24 mmol) in DMF, followed by stirring at the same temperature for 2 hours. Water was added to the reaction mixture, and extraction with ethyl acetate was performed. The organic layer was washed with a saturated aqueous sodium hydrogencarbonate solution, water and a saturated salt solution in this order, and dried over anhydrous sodium sulfate. The solvent was distilled off under reduced pressure, and the residue was purified by silica gel column chromatography (eluent: ethyl acetate/n-hexane=1/3). The solvent was distilled off under reduced pressure, to thereby obtain 65 mg (yield: 61%) of 2-{3-[2-(3,4-diethoxyphenyl)thiazole-4-yl]propionyl}-N,N-dimethylbenzamide as a colorless oil.

NMR δ ppm (CDCl3); 7.88 (1H, d, J=7.4 Hz), 7.6-7.3 (4H, m), 7.3-7.2 (1H, m), 6.9-6.8 (2H, m), 4.2-4.1 (4H, m), 3.45 (2H, t, J=7.3 Hz), 3.20 (2H, t, J=7.2 Hz), 3.14 (3H, s), 2.76 (3H, s), 1.5-1.4 (6H, m)

Example 242

Production of 3-[2-(3,4-dimethoxyphenyl)thiazole-4-yl]-1-(3,4-diacetoxyphenyl)propanone Acetic anhydride (2 ml, 20 mmol) was added dropwise at room temperature to a solution (4 ml) of 3-[2-(3,4-dimethoxyphenyl)thiazole-4-yl]-1-(3,4-dihydroxyphenyl)propanone (320 mg, 0.78 mmol) in pyridine at room temperature, followed by stirring at the same temperature for 1 hour. Methanol (10 ml) was added to the reaction mixture, stirring was carried out at room temperature for 1 hour, and the solvent was distilled off under reduced pressure. Subsequently, water was added, and extraction with ethyl acetate was performed. The residue was purified by silica gel column chromatography (eluent: ethyl acetate). The solvent was distilled off under reduced pressure, and the residue was recrystallized from an ethyl acetate/n-hexane mixed solvent, to thereby obtain 195 mg (yield: 54%) of 3-[2-(3,4-dimethoxyphenyl)thiazole-4-yl]-1-(3,4-diacetoxyphenyl)propanone as colorless needles.

Melting point: 128-128.5° C.

Example 243

Production of 3-[2-(3,4-dimethoxyphenyl)thiazole-4-yl]-1-(3,4-diethoxyphenyl)propanone Ethyl iodide (0.48 ml, 6.0 mmol) and potassium carbonate (0.62 g, 4.5 mmol) were added at room temperature to a solution (7 ml) of 3-[2-(3,4-dimethoxyphenyl)thiazole-4-yl]-1-(3,4-dihydroxyphenyl)propanone (0.58 g, 1.5 mmol) in DMF, followed by stirring at 60° C. for 1 hour. After cooling to room temperature, ethyl acetate was added to the reaction mixture, the resulting mixture was filtered, and the solvent was distilled off under reduced pressure. The residue was purified by silica gel column chromatography (eluent: ethyl acetate/n-hexane=1/2). The solvent was distilled off under reduced pressure, and the residue was recrystallized from an ethyl acetate/n-hexane mixed solvent, to thereby obtain 290 mg (yield: 44%) of 3-[2-(3,4-dimethoxyphenyl)thiazole-4-yl]-1-(3,4-diethoxyphenyl)propanone as a white powder.

Melting point: 141.3-142.4° C.

Examples 244 to 247

According to the production process of Example 186, the following compounds of Examples 244 to 247 were produced (Table 22).

TABLE 22

| Ex. | Compound | MS (M + 1) |
|---|---|---|
| 244 | 3-[2-(3,4-diethoxyphenyl)thiazole-4-yl]-1-naphthalene-1-yl-1-propanol | 434 |
| 245 | 3-[2-(3,4-diethoxyphenyl)thiazole-4-yl]-1-naphthalene-2-yl-1-propanol | 434 |
| 246 | 3-[2-(3,4-diethoxyphenyl)thiazole-4-yl]-1-quinoxaline-6-yl-1-propanol | 436 |
| 247 | 1-benzo[1,3]dioxol-5-yl-3-[2-(3,4-diethoxyphenyl)thiazol-4-yl]-1-propanol | 428 |

Example 248

According to the production process of Example 58, the following compound was produced.

Methyl 2-[2-(3,4-diethoxyphenyl)thiazole-4-ylmethyl]-2-(3-ethoxypyridine-2-yl)-3-oxobutyrate NMR δ ppm (CDCl3); 8.22 (1H, dd, J=1.4 Hz, 4.3 Hz), 7.5-7.3 (4H, m), 6.9-6.8 (2H, m), 4.8-4.6 (1H, m), 4.2-4.0 (4H, m), 3.90 (3H, s), 3.65 (3H, s), 3.0-2.8 (2H, m), 2.6-2.3 (2H, m), 1.5-1.4 (6H, m)

Example 249

According to the production process of Example 87, the following compound was produced.

3-[2-(3,4-diethoxyphenyl)thiazole-4-yl]-1-(3-ethoxypyridine-2-yl)-1-butanone

NMR δ ppm (CDCl3); 8.30-8.20 (1H, m), 7.51 (1H, d, J=1.8 Hz), 7.5-7.3 (3H, m), 6.9-6.8 (2H, m), 4.3-4.1 (4H, m), 3.89 (3H, s), 3.20 (2H, t, J=7.3 Hz), 2.91 (2H, t, J=7.5 Hz), 2.2-2.1 (2H, m), 1.5-1.4 (6H, m)

Example 250

According to the production process of Example 90, the following compound was produced.

2-[2-(3,4-diethoxyphenyl)thiazole-4-yl]-1-(2-methoxyphenyl)ethanone

NMR δ ppm (CDCl3); 7.79 (1H, dd, 1.8, 7.7 Hz), 7.49 (1H, d, J=2.1 Hz), 7.49-7.46 (1H, m), 7.42 (1H, dd, J=2.1, 8.4 Hz), 7.06 (1H, s), 7.03-7.00 (1H, m), 6.98 (1H, d, J=8.4 Hz), 6.88 (1H, d, J=8.4 Hz), 4.55 (2H, s), 4.18 (2H, q, J=7.0 Hz), 4.14 (2H, q, J=7.0 Hz), 3.92 (3H, s), 1.48 (3H, t, J=7.0 Hz), 1.47 (3H, t, J=7.0 Hz)

Test Example 1

Confirmatory Test for Phosphodiesterase (PDE) 4 Inhibitory Activity

Using the compounds of Examples 1, 78, 87, 88, 99, 100, 106, 107, 158, 162, 165, 167, 174, 175, 187, 227, 238 and 239 as test substances, the following test was conducted to evaluate their phosphodiesterase (PDE) 4 inhibitory activity.

(1) Mass Preparation of Plasmids

Plasmids containing genes coding for human PDE4D (HPDE4D) (stored in Otsuka America Pharmaceutical, Inc., Maryland Research Laboratories) were transformed into *Escherichia coli*, and mass cultured. The plasmids were then purified using EndoFree™ Plasmid Mix Kit (Qiagen).

(2) Mass expression and purification of PDE4D

African green monkey kidney-derived COS-7 cells (RCB 0539) were subcultured in a DMEM medium containing 100 units/ml penicillin, 100 μm/ml streptomycin and 10% FBS. The plasmids prepared in (1) were transfected into the cells, using LipofectAMINE™ 2000 Reagent (hereinafter referred to as "LF2000", a product of Invitroge), according to the attached protocol. For comparison, pcDNA3.1 was transfected as a control vector. The COS-7 cells were inoculated into 10 cm diameter petri dishes on the day before transfection, so that the cells reached 90% confluence on the day of transfection. Twelve micrograms of the plasmids diluted with 0.9 ml of OPTI-MEM I (Invitrogen) (a plasmid solution; Solution A) and 30 μl of LF2000 diluted with 0.9 ml of OPTI-MEM I (a LF2000 solution; Solution B) were prepared per petri dish, and allowed to stand at room temperature for 5 minutes. Solutions A and B were then mixed together and allowed to stand at room temperature for 20 minutes. The mixture was added to the cultured cells, and incubation was performed overnight at 37° C. in an atmosphere of 5% $CO_2$. The culture medium was changed on the following day, incubation was continued overnight, and the cells were collected by the following procedure. First, the cells were washed once with PBS (Sigma), and 2 ml of Trypsin-EDTA solution (Sigma) was added per petri dish, spread over the dish and removed. The cells were then allowed to stand at 37° C. for 2 to 3 minutes, separated from the petri dish and suspended in a medium. The suspension was placed in a centrifuge tube, and centrifuged at 200×g and 4° C. for 5 minutes. The supernatant was then removed. The cells were further washed with PBS and stored at −80° C. A KHEM buffer (50 mM Hepes, 50 mM KCl, 10 mM EGTA, 1.92 mM $MgCl_2$, pH 7.2) containing 1 mM DTT, 40 μg/ml PMST, 156 μg/ml benzamidine, 1 μg/ml apotinin, 1 μg/ml leupeptin, 1 μg/ml pepstatin A, and 1 μg/ml antipain was added to the cells that had been stored, and the resulting mixture was placed in a glass homogenizer and homogenized on ice. The cell suspension was centrifuged at 100×g and 4° C. for 5 minutes, and the supernatant was further centrifuged at 100,000×g for 1 hour. Thereafter, the supernatant was dispensed into new tubes as a PDE4D enzyme solution, and stored in an ultra-low-temperature freezer. The protein concentration of the PDE4D enzyme solution was then measured.

(3) Determination of Dilution Factor of PDE4D Enzyme Solution

The PDE4D enzyme solution prepared in (2) was diluted 10-, 25-, 50-, 100-, 200-, 400- and 800-fold with 20 mM Tris-HCl (pH 7.4), and the PDE4D activities of the diluted enzyme solutions were measured by the method described in (4) to determine the optimum dilution factor to obtain a PDE4D enzyme solution in which degraded cAMP constituted 10 to 30% of the total cAMP.

(4) Measurement of PDE4D Inhibitory Activity

The necessary amount of each test substance was weighed out and dissolved in 100% DMSO to a concentration of 10 mM. The resulting solutions were stored in a freezer as test substance stock solutions. Before the inhibitory activity measurement, the stock solutions were melted, diluted 2-fold with 100% DMSO to a concentration of 5 mM, and further diluted with 100% DMSO to obtain test substance solutions with 10 graded concentrations. Each test substance solution was added to a 1.2 ml tube containing 23 μl of 20 mM Tris-HCl (pH 7.4). Twenty five microliters of the PDE4D enzyme solution at the optimum dilution factor determined in (3) was added under ice cooling, and 50 μl of a substrate solution, which contained 2 μM [$^3$H]cAMP obtained by dilution with 20 mM Tris-HCl (pH 7.4) containing 10 mM $MgCl_2$, was added. The final DMSO concentration in the reaction mixture was 2%. After stirring, the mixture was incubated at 30° C. for 10 minutes. After completion of the incubation, the tubes were placed in a boiling water bath for 3 minutes to terminate the reaction. The tubes were cooled in ice, and 25 μl of 0.2 μg/ml snake venom solution was added. After stirring, incubation was carried out at 30° C. for 10 minutes. After completion of incubation, 0.4 ml of a Dowex 1×8 resin solution prepared using a $EtOH:H_2O$ (1:1) mixture was added. After stirring, the mixture was allowed to stand at room temperature for at least 1 hour. Fifty microliters of each of the supernatants in the tubes was placed in a well of a Topcount plate, and the plate was dried overnight. The radioactivity (cpm) of [$^3$H] was measured using a Topcount. Specifying the radioactivity of [$^3$H] as X cpm, the radioactivity of the total [$^3$H]cAMP added in the reaction system as T cpm, and the protein concentration of the reaction mixture as Y mg/ml, the PDE4D activity in the reaction mixture was found from the following equation.

$$PDE4D \text{ activity (pmol/min/mg)} = \frac{391.67}{50} \times \frac{X}{T} \times \frac{10^{-11}}{10} \times 10^{12} \times \frac{1}{0.1} \times \frac{1}{Y}$$

To find the PDE4D inhibitory activities of the test substances, cpm in the absence of the test substances, from which cpm in the absence of the enzyme had been subtracted, was set as 100%, and the rates of inhibition by the test substances were expressed as percentages of control. Thereafter, the $IC_{50}$ value (the concentration that inhibits the PDE4 activity by 50%) of each test substance was calculated.

Table 23 shows the results. The results demonstrate that the compounds represented by Formula (1) have excellent PDE4 inhibitory activity.

TABLE 23

| Test substance | $IC_{50}$ value (μM) |
|---|---|
| Compound of Example 1 | 0.0236 |
| Compound of Example 78 | 0.0100 |
| Compound of Example 87 | 0.0002 |
| Compound of Example 88 | 0.0004 |
| Compound of Example 99 | 0.0290 |
| Compound of Example 100 | 0.0023 |
| Compound of Example 106 | 0.0057 |
| Compound of Example 107 | 0.0058 |
| Compound of Example 158 | 0.0057 |
| Compound of Example 162 | 0.0016 |
| Compound of Example 165 | 0.0150 |
| Compound of Example 167 | 0.0100 |
| Compound of Example 174 | 0.0100 |
| Compound of Example 175 | 0.0330 |
| Compound of Example 187 | 0.0066 |
| Compound of Example 227 | 0.0290 |
| Compound of Example 238 | 0.0072 |
| Compound of Example 239 | 0.0097 |

Test Example 2

Measurement of TNF-α Production Inhibitory Activity

The following tests were performed to evaluate TNF-α production inhibitory activity.

(1) Separation of Human Peripheral Blood Mononuclear Cells

A peripheral blood sample was obtained from a healthy adult donor who had signed a written informed consent. Thirty milliliters of the blood sample, which had been heparinized, was dispensed into a Leucosep tube (Greiner) containing 16 ml of a lymphocyte separation solution (Nakarai Chemical, Ltd.) under the filter barrier, and centrifuged at 1000×g for 15 minutes.

The intermediate layer corresponding to a mononuclear cell fraction was collected in a 50 ml centrifuge tube, and washed twice with a RPMI 1640 medium. After trypan blue staining, the viable count was determined and adjusted to $2 \times 10^6$ cells/ml with RPMI 1640 medium.

(2) Induction of TNF-α Production

E. coli (Serotype 055:B5)-derived LPS, which had been dissolved in a RPMI 1640 medium to a concentration of 5 mg/ml, sterilized by filtration and stored in a freezer, was melted and diluted with a RPMI 1640 medium to 10 μg/ml. The test substances were dissolved in DMSO to obtain solutions with a concentration of 50 times the final use concentration. One microliter of each of the graded concentration test substance solutions, 149 μl of RPMI 1640 medium, 50 μl of LPS solution (final concentration: 1 μg/ml), 50 μl of fetal bovine serum, and 50 ml of the peripheral blood mononuclear cell suspension were dispensed to each well of a 48-well plate and incubated at 37° C. for 24 hours.

(3) Measurement of TNF-α Concentration

After completion of the incubation, the culture supernatant was collected from each well, and the TNF-α concentration in the supernatant was measured by ELISA method (Human TNF-α Eli-pair, Diaclone). The TNF-α concentration caused by LPS stimulation in the absence of test substances was set as 100%, and the rates of inhibition by the test substances were expressed as percentages of the control, and the $IC_{50}$ value (the concentration that inhibits TNF-α production by 50%) of each test substance was calculated.

Table 24 shows the results. The results demonstrate that the compounds represented by Formula (1) have TNF-α production inhibitory activity.

TABLE 24

| Test Substance | $IC_{50}$ value (μM) |
|---|---|
| Compound of Ex. 1 | 0.008 |
| Compound of Ex. 48 | 0.25 |
| Compound of Ex. 51 | 0.8 |
| Compound of Ex. 52 | 0.13 |
| Compound of Ex. 56 | 0.16 |
| Compound of Ex. 89 | 0.007 |
| Compound of Ex. 91 | 0.543 |
| Compound of Ex. 153 | 0.183 |

Test Example 3

Measurement of IL-4 Production Inhibitory Activity

The following tests were performed to evaluate IL-4 production inhibitory activity.

(1) Separation of Mouse Spleen Cells

The abdomens of six- to ten-week-old male BALB/c mice were incised under ether anesthesia, and the spleens were excised. The spleens were separated into pieces by forcing them through a mesh using a glass pestle, and the spleen cells were suspended in RPMI 1640 medium. The suspension was filtered through a Cell Strainer and centrifuged at 100×g for 10 minutes. The cell pellets were suspended in a red blood cell solution (0.75% ammonium chloride, 17 mM tris-hydrochloric acid buffer) and centrifuged. Thereafter, a RPMI 1640 medium was added to the cell pellets to resuspend the cells. After centrifugation, the cells were washed twice, and the viable count was determined by trypan blue staining and adjusted to $2 \times 10^6$ cells/ml with RPMI 1640 medium.

(2) Induction of IL-4 Production

ConA, which had been dissolved in a cell culture solution (a RPMI 1640 medium containing 10% fetal bovine serum) to a concentration of 5 mg/ml, sterilized by filtration and stored in a freezer, was melted and diluted with a cell culture solution to 50 μg/ml. The test substances were dissolved in DMSO, diluted with a cell culture solution to a concentration of 10 times the final use concentration. Fifty microliters of each of the graded concentration test substance solutions, 150 μl of cell culture solution, 50 μl of ConA solution (final concentration: 5 μl/ml) and 20 μl of mouse spleen cell suspension were dispensed to each well of a 48-well plate and incubated at 37° C. for 48 hours.

(3) Measurement of IL-4 Concentration

After completion of the incubation, the culture supernatant was collected from each well, and the IL-4 concentration of the supernatant was measured by the ELISA method (mouse IL-4 EIA kit, BD Pharmingen). The IL-4 concentration caused by ConA stimulation in the absence of test substances was set as 100%, the rates of inhibition by the test substances were expressed as percentages of the control, and the $IC_{50}$ value of each test substance was calculated as the test substance concentration that inhibits IL-4 production by 50%.

Formulation Example 1

Ointment

One gram of the compound of the present invention was dispersed in 10 g of liquid paraffin to obtain a dispersion. A base was prepared by heating and mixing 3 g of paraffin, 5 g of white beeswax and 81 g of white petrolatum, and cooled, and when it had cooled to about 60° C., the above dispersion was added. After mixing, the mixture was cooled to obtain an ointment.

Formulation Example 2

Cream

One gram of the compound of the present invention was dispersed in an aqueous solution containing 10 g of purified water and 1 g of polyoxyethylene hydrogenated castor oil 60, to obtain a dispersion. An emulsion base, comprising 25 g of white petrolatum, 20 g of stearyl alcohol, 12 g of propylene glycol, 3 g of polyoxyethylene hydrogenated castor oil 60, 1 g of glyceryl monostearate, 0.1 g of methyl paraoxybenzoate, 0.1 g of propyl paraoxybenzoate and 26.8 g of purified water, was prepared with heating. The obtained emulsion base was cooled, and when it had cooled to 60° C., the above dispersion was added. After mixing, the mixture was cooled to obtain a cream.

The compound of the present invention exhibits specific inhibitory activity against PDE4, and thus is useful as an active ingredient of a PDE4 inhibitor.

Further, the compound of the present invention, based on its specific inhibitory activity against PDE4, is useful as a preventive or therapeutic agent for atopic dermatitis and various other diseases.

The invention claimed is:

1. A compound represented by Formula (1), an optical isomer thereof, or a pharmaceutically acceptable salt thereof:

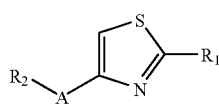

(1)

wherein
R1 is a di-$C_{1-6}$ alkoxyphenyl group;
R2 is any one of the following groups (a) to (t):
(a) a phenyl group in which the phenyl ring may be substituted with one or more members selected from the group consisting of (a-1) hydroxy groups, (a-2) halogen atoms, (a-3) unsubstituted or halogen-substituted $C_{1-6}$ alkyl groups, (a-4) unsubstituted or halogen-substituted $C_{1-6}$ alkoxy groups, (a-5) $C_{1-6}$ alkoxy-$C_{1-6}$ alkoxy groups, (a-6) amino-$C_{1-6}$ alkoxy groups which may be substituted with a $C_{1-6}$ alkyl group or groups, (a-7) methylenedioxy groups, (a-8) carboxy groups, (a-9) phenoxy groups, (a-10) $C_{1-6}$ alkoxycarbonyl groups, (a-11) $C_{1-6}$ alkanoyloxy groups, (a-12) $C_{1-6}$ alkanoyl groups, (a-13) cyano groups, (a-14) nitro groups, (a-15) $C_{1-6}$ alkylcarbamoyl groups, (a-16) aminosulfonyl groups, (a-17) amino groups which may be substituted with a $C_{1-6}$ alkyl group or groups, (a-18) $C_{1-6}$ alkanoylamino groups, (a-19) $C_{1-6}$ alkylthio groups, (a-20) phenyl groups, (a-21) pyrazolyl groups, (a-22) imidazolyl groups, (a-23) triazolyl groups, (a-24) morpholino groups, (a-25) pyrrolidinyl groups, (a-26) piperazinylcarbonyl groups which may be substituted with a $C_{1-6}$ alkyl group or groups, and (a-27) phenyl-$C_{1-5}$ alkoxy groups;
(b) a naphthyl group;
(c) a pyridyl group in which the pyridine ring may be substituted with one or more members selected from the group consisting of (c-1) hydroxy groups, (c-2) $C_{1-6}$ alkyl groups, (c-3) $C_{1-6}$ alkoxy groups, (c-4) phenyl-$C_{1-6}$ alkoxy groups, and (c-5) $C_{1-6}$ alkoxycarbonyl groups;
(d) a furyl group in which the furan ring may be substituted with a $C_{1-6}$ alkyl group or groups;
(e) a thienyl group in which the thiophene ring may be substituted with one or more members selected from the group consisting of (e-1) halogen atoms, (e-2) $C_{1-6}$ alkyl groups, and (e-3) $C_{1-6}$ alkoxy groups;
(f) an isoxazolyl group in which the isoxazolyl ring may be substituted with a $C_{1-6}$ alkyl group or groups;
(g) a thiazolyl group in which the thiazole ring may be substituted with one or more members selected from the group consisting of (g-1) $C_{1-6}$ alkyl groups, and
(g-2) phenyl groups which may be substituted with a $C_{1-6}$ alkoxy group or groups;
(h) a pyrrolyl group in which the pyrrole ring may be substituted with a $C_{1-6}$ alkyl group or groups;
(i) an imidazolyl group in which the imidazole ring may be substituted with a $C_{1-6}$ alkyl group or groups;
(j) a tetrazolyl group;
(k) a pyrazinyl group;
(l) a thienothienyl group;
(m) a benzothienyl group;
(n) an indolyl group in which the indole ring may be substituted with a $C_{1-6}$ alkoxy group or groups;
(o) a benzimidazolyl group in which the benzimidazole ring may be substituted with a $C_{1-6}$ alkyl group or groups;
(p) an indazolyl group;
(q) a quinolyl group;
(r) a 1,2,3,4-tetrahydroquinolyl group in which the 1,2,3,4-tetrahydroquinoline ring may be substituted with an oxo group or groups;
(s) a quinoxalinyl group; and
(t) a 1,3-benzodioxolyl group; and
A is any one of the following groups (i) to (iii):
(i) —CH(OH)—B— wherein B is a $C_{1-6}$ alkylene group;
(ii) —COCH(COOR3)-Bb- wherein R3 is a $C_{1-6}$ alkyl group and Bb is a $C_{1-6}$ alkylene group; and
(iii) -Bc- wherein Bc is a $C_{2-6}$ alkylene group.

2. A compound according to claim 1, wherein, in Formula (1), R1 is a 3,4-di-$C_{1-6}$ alkoxyphenyl group; an optical isomer thereof; or a pharmaceutically acceptable salt thereof.

3. A compound according to claim 1, wherein, in Formula (1), R2 is
(a) a phenyl group in which the phenyl ring may be substituted with one or more members selected from the group consisting of (a-1) hydroxy groups, (a-2) halogen atoms, (a-3) unsubstituted or halogen-substituted $C_{1-6}$ alkyl groups, (a-4) unsubstituted or halogen-substituted $C_{1-6}$ alkoxy groups, (a-5) $C_{1-6}$ alkoxy-$C_{1-6}$ alkoxy groups, (a-6) amino-$C_{1-6}$ alkoxy groups which may be substituted with a $C_{1-6}$ alkyl group or groups, (a-7) methylenedioxy groups, (a-8) carboxy groups, (a-9) phenoxy groups, (a-10) $C_{1-6}$ alkoxycarbonyl groups, (a-11) $C_{1-6}$ alkanoyloxy groups, (a-12) alkanoyl groups, (a-13) cyano groups, (a-14) nitro groups, (a-15) $C_{1-6}$ alkylcarbamoyl groups, (a-16) aminosulfonyl groups, (a-17) amino groups which may be substituted with a $C_{1-6}$ alkyl group or groups, (a-18) $C_{1-6}$ alkanoylamino groups, (a-19) $C_{1-6}$ alkylthio groups, (a-20) phenyl groups, (a-21) pyrazolyl groups, (a-22) imidazolyl groups, (a-23) triazolyl groups, (a-24) morpholino groups, (a-25) pyrrolidinyl groups, (a-26) piperazinylcarbonyl groups which may be substituted with a $C_{1-6}$ alkyl group or groups, and (a-27) phenyl-$C_{1-6}$ alkoxy groups;
(c) a pyridyl group in which the pyridine ring may be substituted with one or more members selected from the group consisting of (c-1) hydroxy groups, (c-2) $C_{1-6}$ alkyl groups, (c-3) $C_{1-6}$ alkoxy groups, (c-4) phenyl-$C_{1-6}$ alkoxy groups, and (c-5) $C_{1-6}$ alkoxycarbonyl groups;
(d) a furyl group in which the furan ring may be substituted with a $C_{1-6}$ alkyl group or groups;
(e) a thienyl group in which the thiophene ring may be substituted with one or more members selected from the group consisting of (e-1) halogen atoms, (e-2) $C_{1-6}$ alkyl groups, and (e-3) $C_{1-6}$ alkoxy groups;
(g) a thiazolyl group in which the thiazole ring may be substituted with one or more members selected from the group consisting of (g-1) $C_{1-6}$ alkyl groups, and (g-2) phenyl groups which may be substituted with a $C_{1-6}$ alkoxy group or groups;
(h) a pyrrolyl group in which the pyrrole ring may be substituted with a $C_{1-6}$ alkyl group or groups; or
(i) an imidazolyl group in which the imidazole ring may be substituted with a $C_{1-6}$ alkyl group or groups;

an optical isomer thereof; or a pharmaceutically acceptable salt thereof.

4. A compound according to claim 1, wherein, in Formula (1), A is
(i) —CH(OH)—B— wherein B is a methylene group or an ethylene group;
(ii) —COCH(COOR3)-Bb- wherein R3 is a methyl group, an ethyl group or a tert-butyl group and Bb is a methylene group or an ethylene group; or
(iii) -Bc- wherein Bc is an ethylene group, a trimethylene group or a tetramethylene group;

an optical isomer thereof; or a pharmaceutically table salt thereof.

5. A compound according to claim 1, wherein, in Formula (1),
R1 is a 3,4-di-$C_{1-6}$ alkoxyphenyl group;
R2 is
(a) a phenyl group in which the phenyl ring may be substituted with one or more members selected from the group consisting of (a-1) hydroxy groups, (a-2) halogen atoms, (a-3) unsubstituted or halogen-substituted $C_{1-6}$ alkyl groups, (a-4) unsubstituted or halogen-substituted $C_{1-6}$ alkoxy groups, (a-5) $C_{1-6}$ alkoxy-$C_{1-6}$ alkoxy groups, (a-6) amino-$C_{1-6}$ alkoxy groups which may be substituted with a $C_{1-6}$ alkyl group or groups, (a-7) methylenedioxy groups, (a-8) carboxy groups, (a-9) phenoxy groups, (a-10) $C_{1-6}$ alkoxycarbonyl groups, (a-11) $C_{1-6}$ alkanoyloxy groups, (a-12) $C_{1-6}$ alkanoyl groups, (a-13) cyano groups, (a-14) nitro groups, (a-15) $C_{1-6}$ alkylcarbamoyl groups, (a-16) aminosulfonyl groups, (a-17) amino groups which may be substituted with a $C_{1-6}$ alkyl group or groups, (a-18) $C_{1-6}$ alkanoylamino groups, (a-19) $C_{1-6}$ alkylthio groups, (a-20) phenyl groups, (a-21) pyrazolyl groups, (a-22) imidazolyl groups, (a-23) triazolyl groups, (a-24) morpholino groups, (a-25) pyrrolidinyl groups, (a-26) piperazinylcarbonyl groups which may be substituted with a $C_{1-6}$ alkyl group or groups, and (a-27) phenyl-$C_{1-6}$ alkoxy groups;
(c) a pyridyl group in which the pyridine ring may be substituted with one or more members selected from the group consisting of (c-1) hydroxy groups, (c-2) $C_{1-6}$ alkyl groups, (c-3) $C_{1-6}$ alkoxy groups, (c-4) phenyl-$C_{1-6}$ alkoxy groups, and (c-5) $C_{1-6}$ alkoxycarbonyl groups;
(d) a furyl group in which the furan ring may be substituted with a $C_{1-6}$ alkyl group or groups;
(e) a thienyl group in which the thiophene ring may be substituted with one or more members selected from the group consisting of (e-1) halogen atoms, (e-2) $C_{1-6}$ alkyl groups, and (e-3) $C_{1-6}$ alkoxy groups;
(g) a thiazolyl group in which the thiazole ring may be substituted with one or more members selected from the group consisting of (g-1) $C_{1-6}$ alkyl groups, and (g-2) phenyl groups which may be substituted with a $C_{1-6}$ alkoxy group or groups;
(h) a pyrrolyl group in which the pyrrole ring may be substituted with a $C_{1-6}$ alkyl group or groups; or
(i) an imidazolyl group in which the imidazole ring may be substituted with a $C_{1-6}$ alkyl group or groups; and A is
(i) —CH(OH)—B wherein B is a $C_{1-6}$ alkylene group;
(ii) —COCH(COOR3)-Bb- wherein R3 is a $C_{1-6}$ alkyl group and Bb is a $C_{1-6}$ alkylene group; or
(iii) -Bc- wherein Bc is a $C_{2-6}$ alkylene group;

an optical isomer thereof; or a pharmaceutically acceptable salt thereof.

6. A pharmaceutical composition comprising a compound according to claim 1, an optical isomer thereof, or a pharmaceutically acceptable salt thereof and a pharmaceutically acceptable base and/or carrier.

7. A method of treating a disease responsive to the inhibiting activity of a phosphodiesterase 4 inhibitor comprising administering as an active ingredient, a compound according to claim 1, an optical isomer thereof, or a pharmaceutically acceptable salt thereof, wherein the disease is atopic dermatitis.

* * * * *

UNITED STATES PATENT AND TRADEMARK OFFICE
CERTIFICATE OF CORRECTION

PATENT NO. : 8,450,352 B2
APPLICATION NO. : 12/638143
DATED : May 28, 2013
INVENTOR(S) : Isao Takemura et al.

It is certified that error appears in the above-identified patent and that said Letters Patent is hereby corrected as shown below:

In the Claims

Claim 4, col. 75, line 19, "pharmaceutically table salt" should read --pharmaceutically acceptable salt--.

Signed and Sealed this
Thirtieth Day of July, 2013

Teresa Stanek Rea
*Acting Director of the United States Patent and Trademark Office*